United States Patent
Reed et al.

(10) Patent No.: US 9,415,368 B2
(45) Date of Patent: *Aug. 16, 2016

(54) DEVICES AND SYSTEMS FOR CREATION OF DNA CLUSTER ARRAYS

(71) Applicant: ILLUMINA, INC., San Diego, CA (US)

(72) Inventors: Mark T. Reed, Menlo Park, CA (US); Andrea Sabot, Essex (GB)

(73) Assignee: Illumina, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/551,232

(22) Filed: Nov. 24, 2014

(65) Prior Publication Data
US 2015/0298088 A1 Oct. 22, 2015

Related U.S. Application Data

(63) Continuation of application No. 12/305,347, filed as application No. PCT/US2007/014649 on Jun. 22, 2007, now Pat. No. 8,921,073.

(60) Provisional application No. 60/816,283, filed on Jun. 23, 2006.

(51) Int. Cl.
*C12M 1/34* (2006.01)
*C12M 3/00* (2006.01)
(Continued)

(52) U.S. Cl.
CPC ........... *B01J 19/0046* (2013.01); *C12Q 1/6837* (2013.01); *B01J 2219/0061* (2013.01); *B01J 2219/00286* (2013.01); *B01J 2219/00333* (2013.01); *B01J 2219/00353* (2013.01); *B01J 2219/00355* (2013.01); *B01J 2219/00391* (2013.01); *B01J 2219/00418* (2013.01); *B01J 2219/00495* (2013.01);
(Continued)

(58) Field of Classification Search
CPC .... C12Q 1/681; C12Q 1/6883; C12Q 1/6827; C12Q 1/6816; C12Q 2600/156; C12Q 1/6869; C12Q 1/6879; C12N 15/1037; C12N 15/1027; C12N 9/2468; C12N 15/85; C12N 9/6459; C12N 2830/85; C12N 2840/20; C40B 40/02; C12M 35/00; B01L 7/52; G06F 19/18
See application file for complete search history.

(56) References Cited

U.S. PATENT DOCUMENTS

| 5,872,244 A | 2/1999 | Hiatt et al. |
| 6,306,597 B1 | 10/2001 | Macevicz |

(Continued)

FOREIGN PATENT DOCUMENTS

| WO | 9844151 | 10/1998 |
| WO | 0018957 | 4/2000 |

(Continued)

OTHER PUBLICATIONS

International Search Report, PCT/US2007/014649, 3pgs, Nov. 13, 2013.

(Continued)

*Primary Examiner* — Michael Hobbs
(74) *Attorney, Agent, or Firm* — The Small Patent Law Group, LLC; Dean D. Small; Jason P. Gross

(57) ABSTRACT

The present invention comprises systems and devices for isothermal amplification of polynucleotide sequences to produce DNA cluster arrays.

21 Claims, 42 Drawing Sheets

(51) Int. Cl.
    *B01J 19/00*     (2006.01)
    *C12Q 1/68*     (2006.01)

(52) U.S. Cl.
    CPC .................. *B01J 2219/00529* (2013.01); *B01J 2219/00596* (2013.01); *B01J 2219/00608* (2013.01); *B01J 2219/00612* (2013.01); *B01J 2219/00626* (2013.01); *B01J 2219/00637* (2013.01); *B01J 2219/00659* (2013.01); *B01J 2219/00689* (2013.01); *B01J 2219/00695* (2013.01); *B01J 2219/00722* (2013.01)

(56) References Cited

U.S. PATENT DOCUMENTS

| | | | |
|---|---|---|---|
| 8,921,073 | B2 * | 12/2014 | Reed .................... B01J 19/0046 435/287.2 |
| 2004/0086872 | A1 | 5/2004 | Childers et al. |
| 2004/0089057 | A1 | 5/2004 | Hobbs et al. |
| 2004/0189311 | A1 | 9/2004 | Glezer |
| 2005/0013732 | A1 | 1/2005 | Battrell et al. |
| 2005/0247701 | A1 | 11/2005 | Deka et al. |
| 2006/0024702 | A1 | 2/2006 | Connolly et al. |
| 2008/0009420 | A1 | 1/2008 | Schroth et al. |

FOREIGN PATENT DOCUMENTS

| | | |
|---|---|---|
| WO | 0246456 | 6/2002 |
| WO | 2004018493 | 3/2004 |
| WO | 2004018497 | 6/2006 |
| WO | 2006064199 | 6/2006 |
| WO | 2007010251 | 1/2007 |
| WO | 2007123744 | 11/2007 |

OTHER PUBLICATIONS

Written Opinion of the International Searching Authority, PCT/US2007-014649, date of mailing Jun. 16, 2008, 3pgs.

Extended European Search Report, dated Nov. 21, 2013, in European Application No. 07796392.4.

Fedurco et al, "BTA, a novel reagent for DNA attachment on glass and efficient generation of solid-phase amplified DNA colonies", Nucleic Acids Research, 2006, vol. 34, No. 3, 13 pages.

* cited by examiner

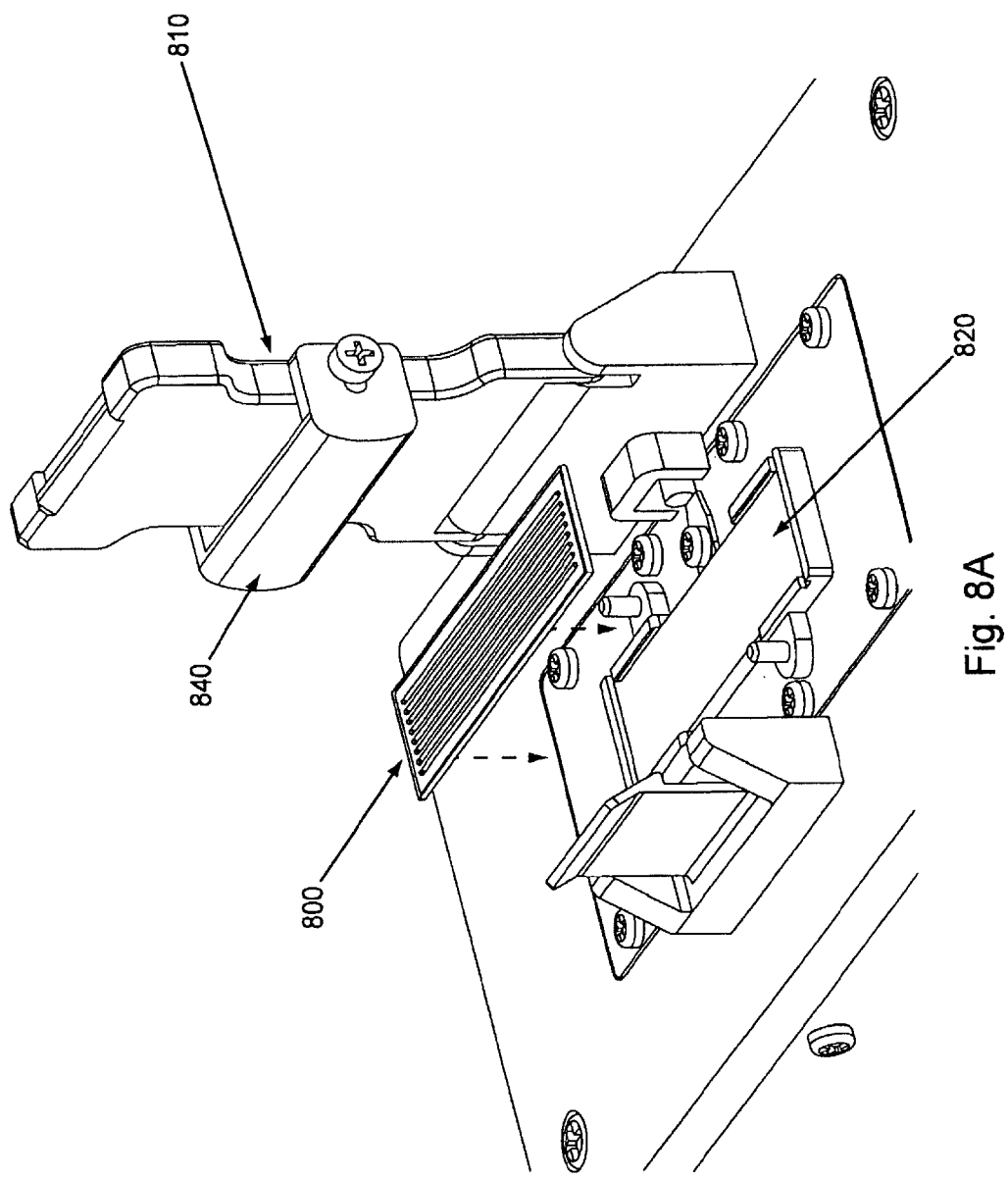

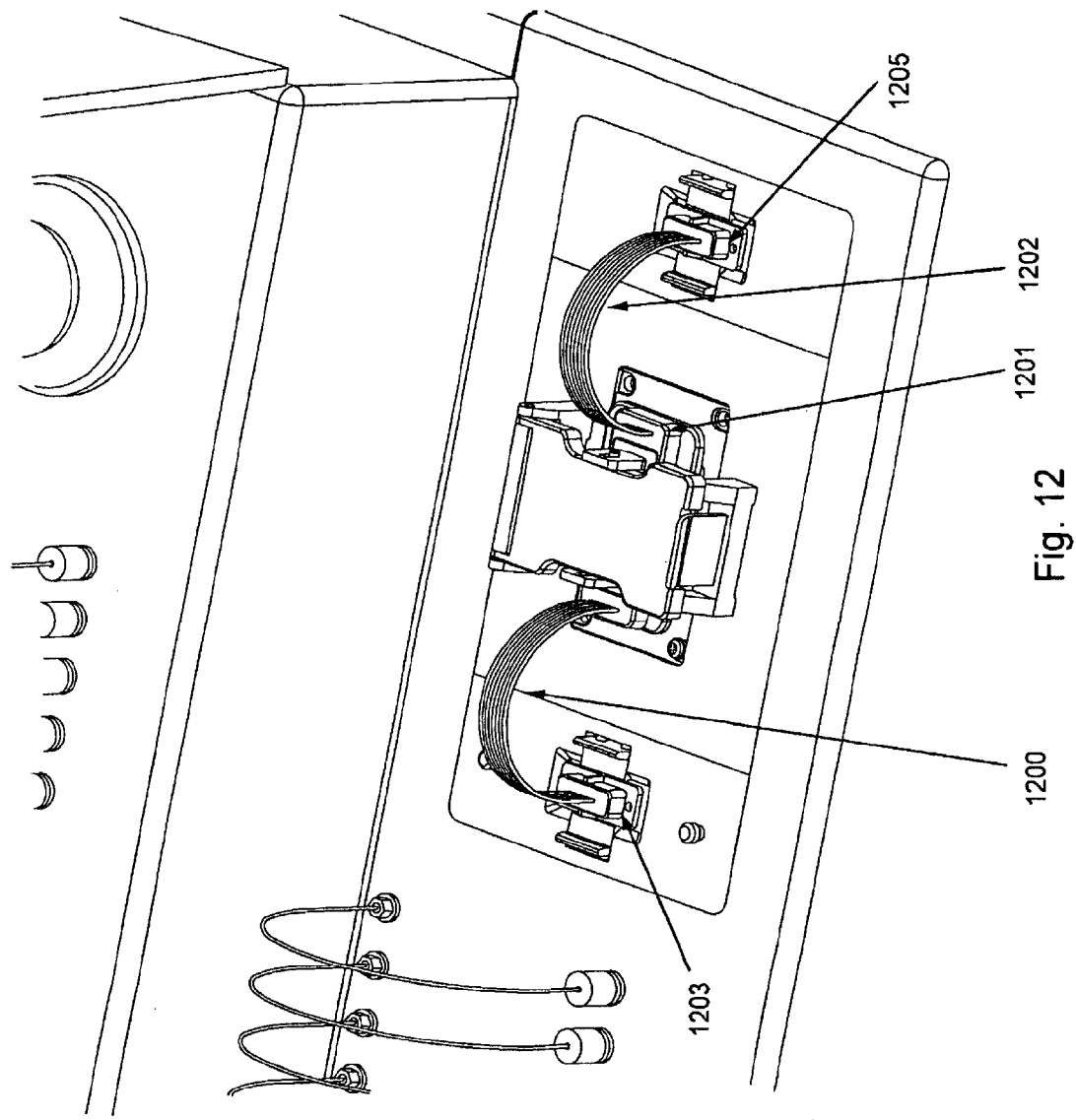

|   | 1 | 2 | 3 | 4 |   |
|---|---|---|---|---|---|
| P7 primer | | Insert | Seq primer | | P5 primer |

1    CAAGCAGAAG ACGGCATACG AGCATAGAGA CCGAGAGAAA TCGGAAGAGC GTCGTGTAGG GAAAGAGTGT GAGATCTTTT ATCATCTCCA TAAAACAAAA
     GTTCGTCTTC TGCCGTATGC TCGTATCTCT GGCTCTCTTT AGCCTTCTCG CAGCACATCC CTTTCTCACA CTCTAGAAAA TAGTAGAGGT ATTTTGTTTT
                                                 └──────────────── 3 ────────────────┘
101  CCCGCGTAG CGAGTTCAGA TAAATAAAT CCCCGCGAGT GCGAGGATTG TTATGTAATA TTGGGTTTAA TCATCTATAT GTTTTGTACA GAGAGGGCAA
     GGGCGGCATC GCTCAAGTCT ATTTTATTTA GGGGCGCTCA CGCTCCTAAC AATACATTAT AACCCAAATT AGTAGATATA CAAAACATGT CTCTCCCGTT

201  GTATCGTTTC CACCGTACTC GTGATAATAA TTTTGCACGG TATCAGTCAT TTCTCGCACA TTGCAGAATG GGGATTTGTC TTCATTAGAC TTATAAACCT
     CATAGCAAAG GTGGCATGAG CACTATTATT AAAACGTGCC ATAGTCAGTA AGAGAGCGTGT AACGTCTTAC CCCTAAACAG AAGTAATCTG AATATTTGGA

301  TCATGGAATA TTTGTATGCC GACTCTATAT CTATACCTTC ATCTCGGTGG TCGCCGTATC ATT
     AGTACCTTAT AAACATACGG CTGAGATATA GATATGGAAG TAGACCCACC AGCCGGCATAG TAA
                                                            └──────── 4 ────────┘

Seq primer for insert: 5' ACACTCTTTCCCTACACGACGCTCTTCCGATC 3'

Fig. 23

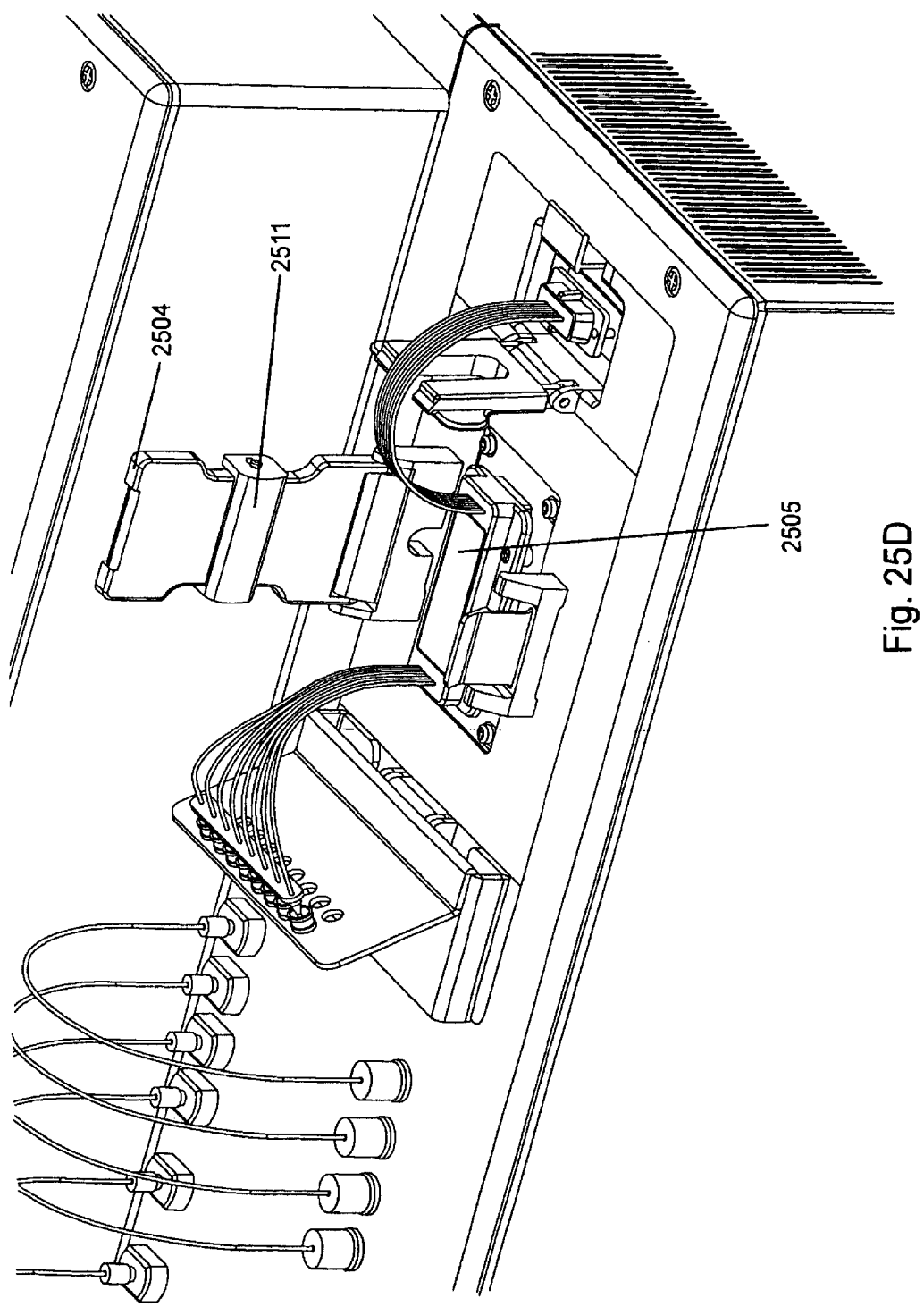

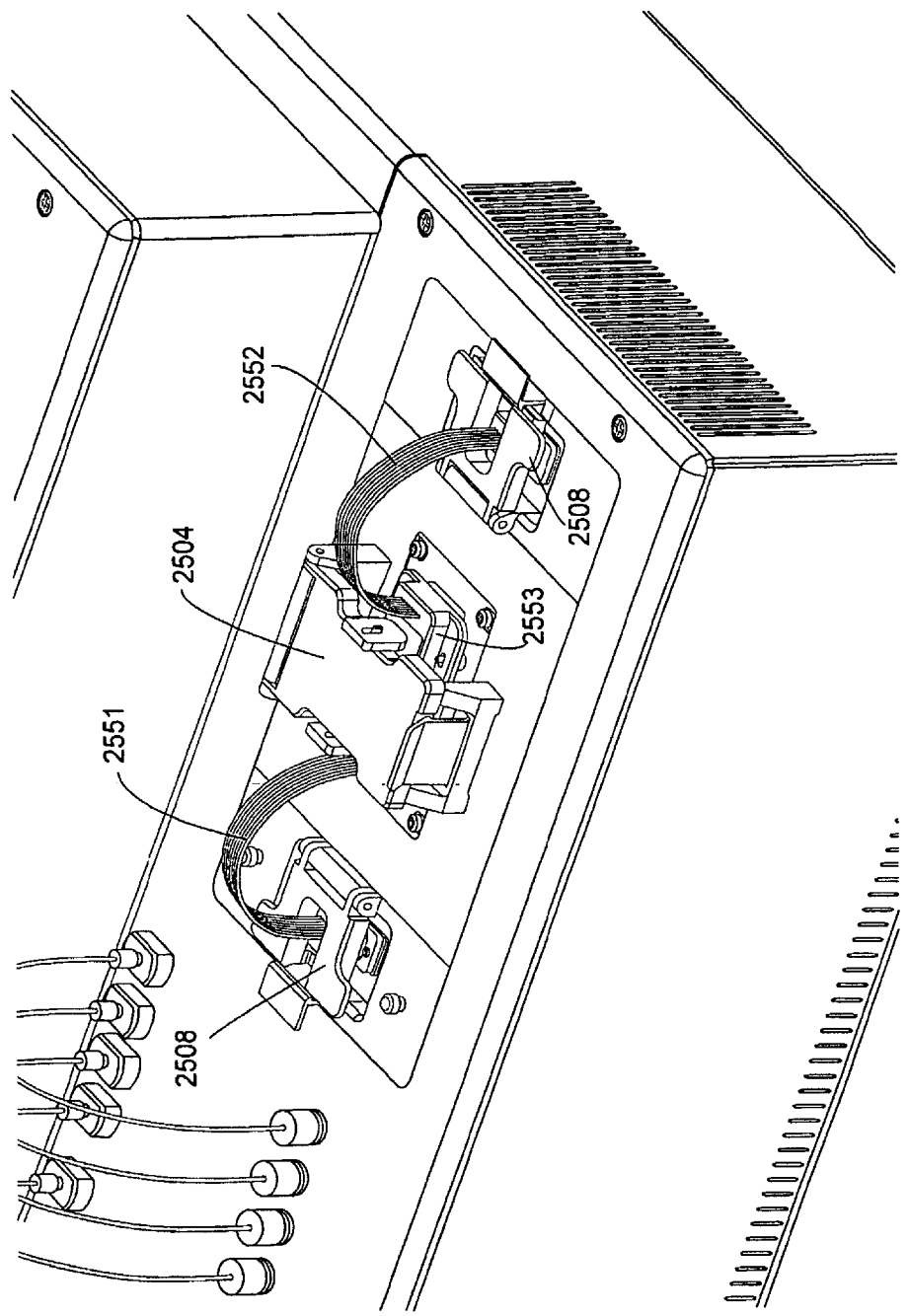

DEVICES AND SYSTEMS FOR CREATION OF DNA CLUSTER ARRAYS

CROSS-REFERENCE TO RELATED APPLICATIONS

The present application is a continuation application of U.S. application Ser. No. 12/305,347, filed on Dec. 17, 2008, and which issued as U.S. Pat. No. 8,921,073 and is hereinafter referred to as "the '347 Application." The '347 Application is a National Stage Entry of International Application No. PCT/US2007/014649, filed on Jun. 22, 2007, which claims the benefit of U.S. Provisional Application No. 60/816,283, filed Jun. 23, 2006. The '347 Application is incorporated herein by reference in its entirety.

FIELD OF THE INVENTION

The current invention relates to the field of nucleic acid amplification. More specifically, the present invention provides systems and devices for the isothermal amplification of polynucleotide sequences to produce DNA cluster arrays on a solid support.

BACKGROUND OF THE INVENTION

Numerous recent advances in the study of biology have benefited from improved methods of analysis and sequencing of nucleic acids. For example, the Human Genome Project has determined the entire sequence of the human genome, which is hoped to lead to further discoveries in fields ranging from treatment of disease to advances in basic science. While the "human genome" has been sequenced there are still vast amounts of genomic material to analyze, e.g., genetic variation between different individuals and tissues, additional species, etc.

However, along with nucleic acid sequencing is the need for amplification of nucleic acids, thereby allowing small amounts of nucleic acid to be easily detected and sequenced. Many methods such as Polymerase Chain Reaction (PCR) and the like currently exist to amplify nucleic acid. PCR (see, e.g., Saiki et al. 1985, *Science* 230: 1350) has become a standard molecular biology technique for amplification of nucleic acid molecules. This in vitro method can be a powerful tool for the detection and analysis of small quantities of nucleic acids, however, PCR can have disadvantages in particular applications.

Briefly, the PCR reaction (typically requiring a target nucleic acid molecule, a molar excess of a forward and reverse primers complementary to the target, deoxynbonucleoside triphosphates (dATP, dTTP, dCTP and dGTP) and a polymerase enzyme) is a DNA synthesis reaction that depends on the extension of forward and reverse primers annealed to opposite strands of a double stranded DNA template that has been denatured (melted apart) at high temperature (90° C. to 100° C.). Copies of the original template DNA are generated through repeated melting, annealing and extension steps, carried out at differing temperatures.

Although there have been many improvements and modifications to the original PCR procedure, PCR continues typically to rely on thermocycling of a reaction mixture, with melting, annealing and extension performed at different temperatures. One major disadvantage of thermocycling reactions relates to the long "lag" times during which the temperature of the reaction mixture is increased or decreased to the correct level. These lag times increase considerably the length of time required to perform an amplification reaction. Additionally, the elevated temperatures required with PCR are not ideal for certain applications, especially where nucleic acid molecules are surface bound.

Moreover, as a result of the high temperatures used during PCR, the reaction mixtures are subject to evaporation. Consequently, PCR reactions are carried out in sealed reaction vessels. However, the use of such sealed reaction vessels has further disadvantages since use of a sealed reaction vessel makes it difficult to alter or add further reaction components. For example, as amplification progresses, depletion of dNTPs can become limiting, thereby, lowering the efficiency of the reaction. Repeated high temperature cycling can also lead to a reduction in the efficiency of the polymerase enzyme; the half life of Taq polymerase may be as low as 40 minutes at 94° C. and 5 minutes at 97° C. (see Wu et al. 1991, *DNA and Cell Biology* 10, 233-238; Landegren U. 1993, *Trends Genet* 9, 199-204; and Saiki et al. 1988, *Science*, 239, 487-491). Again, since the reaction vessels are sealed in PCR, addition of fresh dNTPs or Taq is problematic.

To overcome these technical disadvantages there is a continuing need for better, more economical devices and systems for fast reliable nucleic acid amplification where the amplification method does not rely on temperature cycling. The current invention provides these devices (and methods of their use) as well as other benefits which will be apparent upon examination of the current specification, claims, and figures.

SUMMARY OF THE INVENTION

In various aspects herein, the invention comprises a system or device (i.e., a cluster station system/device) for creation of nucleic acid cluster arrays through isothermal nucleic acid amplification. In some embodiments, such systems/devices comprise a body chassis; a manifold (often 3 manifolds, e.g., sample manifold, common reagent manifold, and wash connection); a fluidic valve (or optionally several multi-port fluidic valves) to direct fluid flow between reservoirs and flow cells, etc.; a fluidic pump (or optionally at least two pumps including a priming pump); a reagent reservoir (typically a plurality of such including reservoirs which can optionally be temperature controlled); at least one temperature control component and optionally one or more such components (e.g., one to create isothermal conditions within the flow cell and optionally one or more to control temperature of particular reagents); and, a computer control component. In such embodiments, the reservoirs, valves, pumps, manifolds, temperature control component, and computer component are functionally connected to one another and the reservoirs, valves, pumps, and manifolds, are directly or indirectly fluidly connected to one another. Also in such embodiments one or more fluids are capable of flow under control of the computer from the reagent reservoirs onto a surface (e.g., of a flow cell), thus, allowing nucleic acid amplification and creation of nucleic acid cluster arrays upon the surface. In such embodiments, the system or device can further comprise at least one flow cell, which is directly or indirectly fluidly connected to the reservoirs, valves, pumps, and manifolds. The fluids flow through such flow cell (thus encountering the channel surfaces and allowing nucleic acid amplification and creation of the nucleic acid cluster arrays on the surface of channels within the flow cell). Also in such embodiments, the nucleic acid clusters are immobilized on the surface of the flow cell and can substantially comprise a plurality of single strand nucleic acid molecules wherein substantially all members of the plurality comprise a 20-40 base nucleic acid primer hybridized to the nucleic acid molecule. In such embodiments, the clusters are amenable to cycles of sequencing using labeled nucleotides. In some embodiments having a number of reagent or waste reservoirs, one or more, or all, of them are optionally not structurally connected to the body chassis, but are fluidly connected to the valve, pump, manifold, and/or flow cell. In the various embodiments, the heating component can hold the flow cell at a substantially isothermal temperature for a determinable period of time.

In yet other aspects, the invention comprises a method of creating nucleic acid cluster arrays through isothermal nucleic acid amplification, by providing a cluster station system or device comprising a body chassis; manifolds (as described herein); fluidic valves (as described herein); fluidic pumps (as described above); reagent and/or waste storage reservoirs; at least one temperature control component (as described herein); and, at least one computer control component. In such methods, the reservoirs, valves, pumps, manifolds, temperature components, and computer component are functionally connected to one another, while the reservoirs, valves, pumps, and manifolds, are directly or indirectly fluidly connected to one another. Also in such methods one or more fluids are capable of flow under control of the computer from the reagent reservoir(s) onto a surface of a flow cell. Such methods also comprise providing amplification reagents, nucleotides, and template nucleic acid and specifically flowing the amplification reagents, and nucleotides under control of the cluster station device through the flow cell (which comprises the nucleic acid template and which is kept under substantially isothermal conditions by the cluster station system or device during the cluster creation process). Thus, in such methods, the nucleic acid template is amplified within the flow cell to create nucleic acid cluster arrays.

In other aspects, the invention comprises kits for creation of nucleic acid cluster arrays. In some embodiments, such kits can comprise nucleic acid cluster formation devices/systems as described herein, as well as optionally include additional assay components (e.g., pre-treated flow cells, buffers, reagents, enzymes, sample materials, control materials, etc.) for using the devices/systems herein to create nucleic acid cluster arrays. Kits of the invention can also comprise appropriate instructions (e.g., printed, recorded on CD and/or DVD, or internet accessible) detailing proper use and optimization of the systems/devices herein to create nucleic acid cluster arrays.

These and other features of the invention will become more fully apparent when the following detailed description is read in conjunction with the accompanying figures and claims.

BRIEF DESCRIPTION OF THE DRAWINGS

FIG. 8A illustrates an exemplary flow cell and flow cell holder.

FIG. 12 displays an optional configuration of an exemplary reagent manifold, flow cell, flow cell holder, and manifold attachment areas.

FIG. 23 displays exemplary DNA monotemplate sequences used for isothermal cluster growth in an exemplary embodiment of the invention.

FIG. 25D illustrates the flow cell holder in an open position with respect to the manifold.

FIG. 25F illustrates the manifold and the two side clamps in closed positions.

DETAILED DESCRIPTION

The present invention comprises systems and devices to create nucleic acid cluster arrays through isothermal solid phase amplification of nucleic acid sequences in flow cells. Such nucleic acid cluster arrays can then be used, inter alia, for sequencing analysis. The nucleic acid clusters produced by the systems/devices herein can optionally be useful in, e.g., sequencing for comparative genomics (such as for genotyping, SNP discovery, BAC-end sequencing, chromosome breakpoint mapping, and whole genome sequence assembly), tracking gene expression, epigenomics (e.g., with methylation mapping DNAseI hypersensitive site mapping or chromatin immunoprecipitation), and aptamer and phage display library characterization.

Those of skill in the art will readily appreciate that while the nucleic acid clusters created by the systems/devices of the invention are amenable to sequencing using a variety of different technologies, they are especially useful for sequencing by synthesis (SBS). SBS relies on using modified 3'-blocked nucleotides nucleosides as described in WO/04018497 and U.S. Pat. No. 5,872,244 to ensure that each cluster is extended by a single base on each sequencing cycle. However, alternative sequencing technologies such as sequencing by ligation, as described in U.S. Pat. No. 6,306,597, Massively Parallel Signature Sequencing (see, e.g., *Nat Biotechnol.* 2000, 6:630-6344), or cycles of extension and quantitation using cycles of exposure to a single unblocked dNTP can also be performed on amplified clusters produced with the current instrumentation.

The systems/devices described herein comprise various combinations of mechanical, fluidic, thermal, electrical, and computing components/aspects that are described more fully below. Thus, even though in certain embodiments the invention is directed towards particular configurations and/or combinations, those of skill in the art will appreciate that not all embodiments necessarily comprise all aspects or particular configurations (unless specifically stated to do so).

Again, in brief, the current invention comprises systems/devices for isothermal amplification of nucleic acids. The nucleic acid clusters produced by use of the invention herein can be utilized in the various procedures and protocols for nucleic acid sequencing. A fluorescent microscope for sequencing clustered arrays of the detailed invention is described elsewhere. See, e.g., U.S. Ser. No. 60/788,248, filed Mar. 31, 2006 and International Application PCT/US2007/007991, filed Mar. 30, 2007, both entitled "Systems and Devices for Sequence by Synthesis Analysis."

Figure 1:
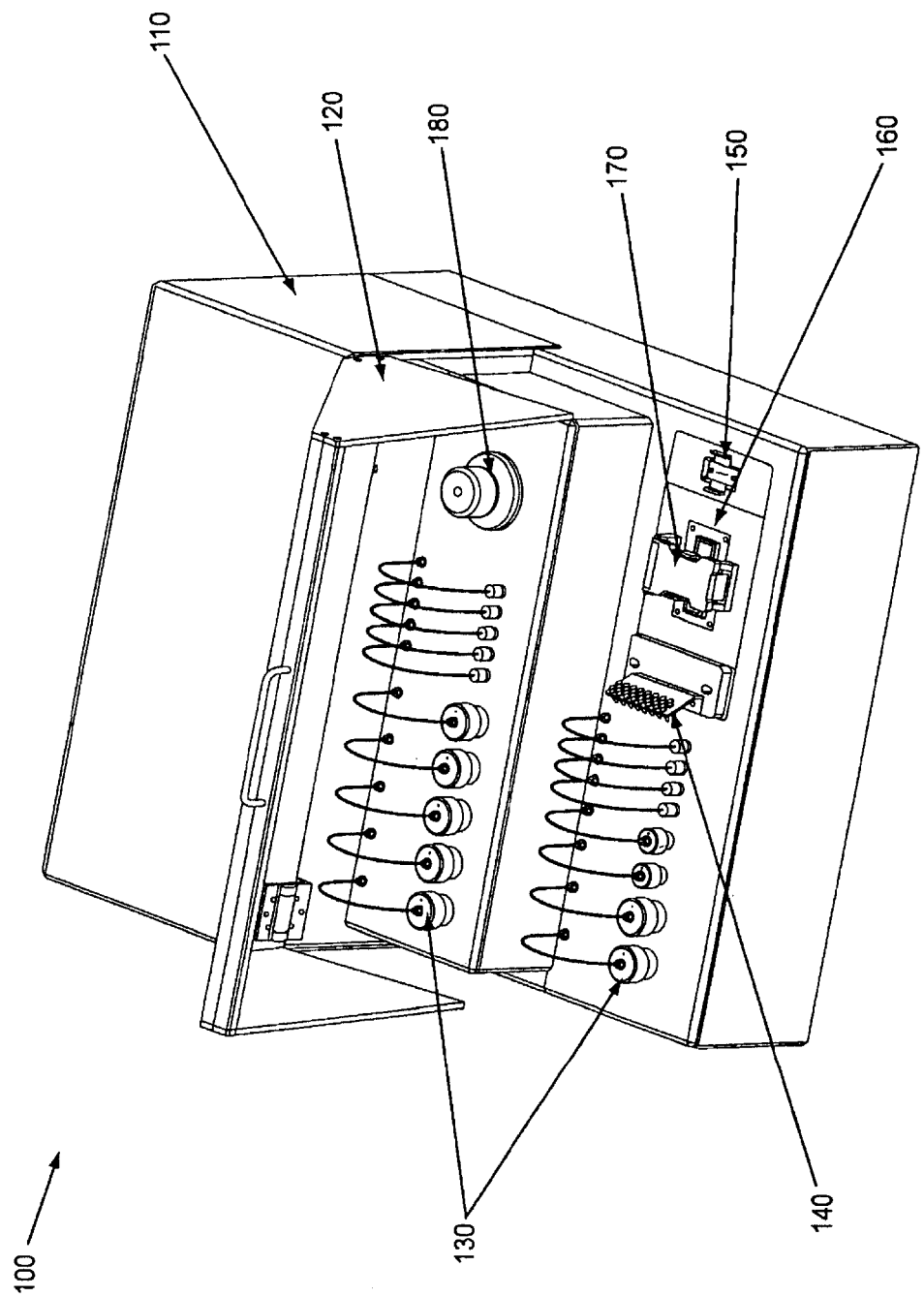
FIG. 1 displays an overview of the major exterior components of an exemplary embodiment of the invention.

The general exterior components of an exemplary embodiment of the current invention are outlined in FIG. 1. As can be seen in FIG. 1, Nucleic Acid Cluster Station (or "Station") 100 comprises body/chassis 110, with access door 120. Arranged within the body of the Station is a plurality of reagent storage reservoirs 130 (optionally divided between reagents stored at ambient or room temperature, e.g., upper level, and reagents stored below room temperature, e.g., lower level). The reagent storage containers, as explained further below, are optionally temperature regulated, can comprise a variable number, and are fluidly connected to a flow cell and eventually to a waste storage reservoir (see below). Also shown in FIG. 1, sample holder 140 which can hold nucleic acid samples (e.g., within tubes) can be fluidly connected to a flow cell via a manifold. A flow cell (not shown in FIG. 1) is typically placed within flow cell placement area (or flow cell station area) 160, and held in proper orientation by flow cell holder 170. Manifold attachment area 150 (distal) allows a manifold to be fluidly connected to, inter alia, the flow cell. While not shown in FIG. 1, but as described below, a second manifold attachment area (proximal) is present underneath sample holder 140 in FIG. 1. Waste reservoir 180 (which is fluidly coupled to the manifold, flow cell, and reagent storage) is also shown in the Figure.

Figure 2:
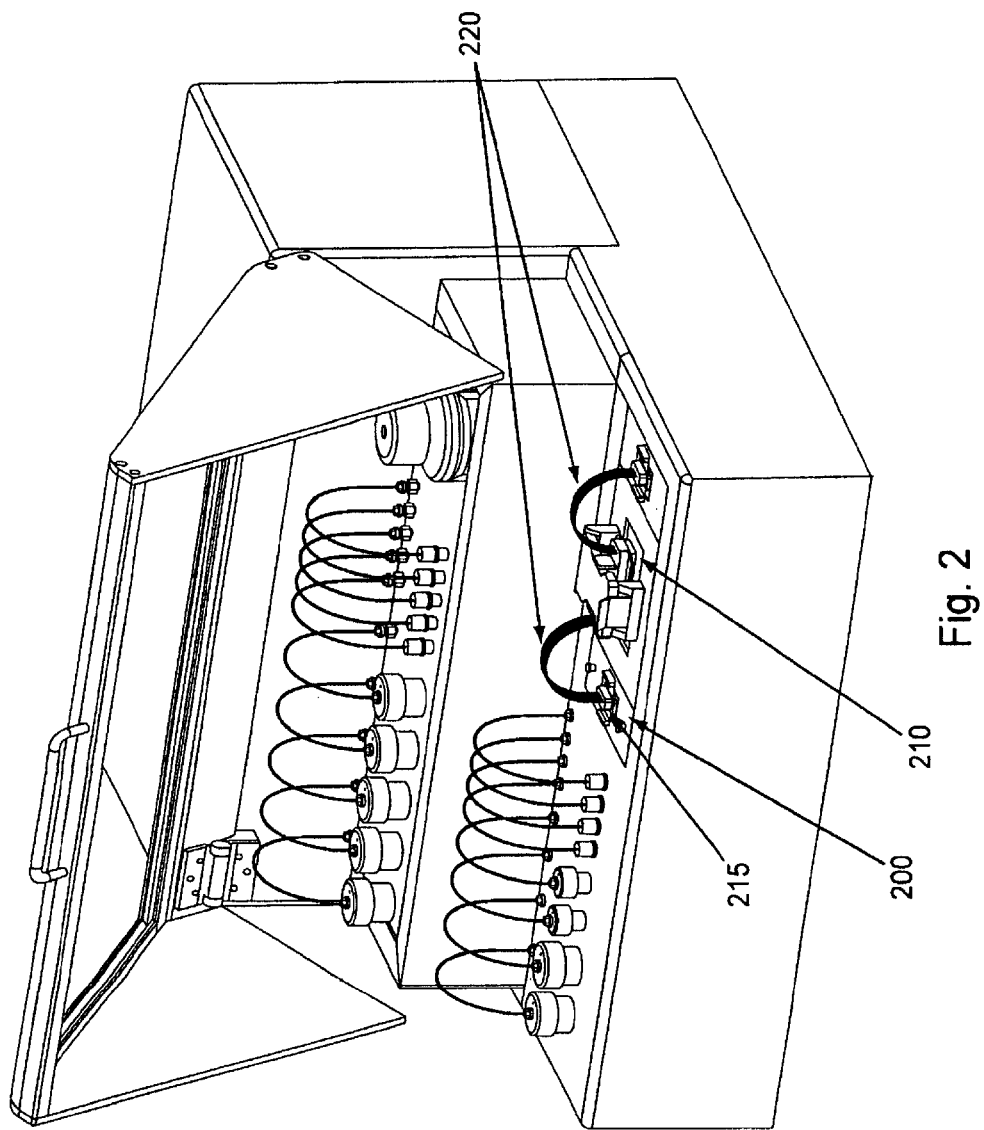
FIG. 2 displays an alternate overview of the major exterior components of an exemplary embodiment of the invention.

FIG. 2 shows an alternate exterior view of an exemplary embodiment of the invention. The embodiment shown in FIG. 2 comprises flow cell 210, and manifold 220. As can be seen by comparison between FIGS. 1 and 2, FIG. 2 does not have a sample holder component present. Thus, the interaction of proximal manifold attachment area 200 and manifold plug 215 can be seen. As explained in more detail below, in many embodiments, the sample holder component is removed during the process as the device/system is used to create nucleic acid clusters.

Figure 3:
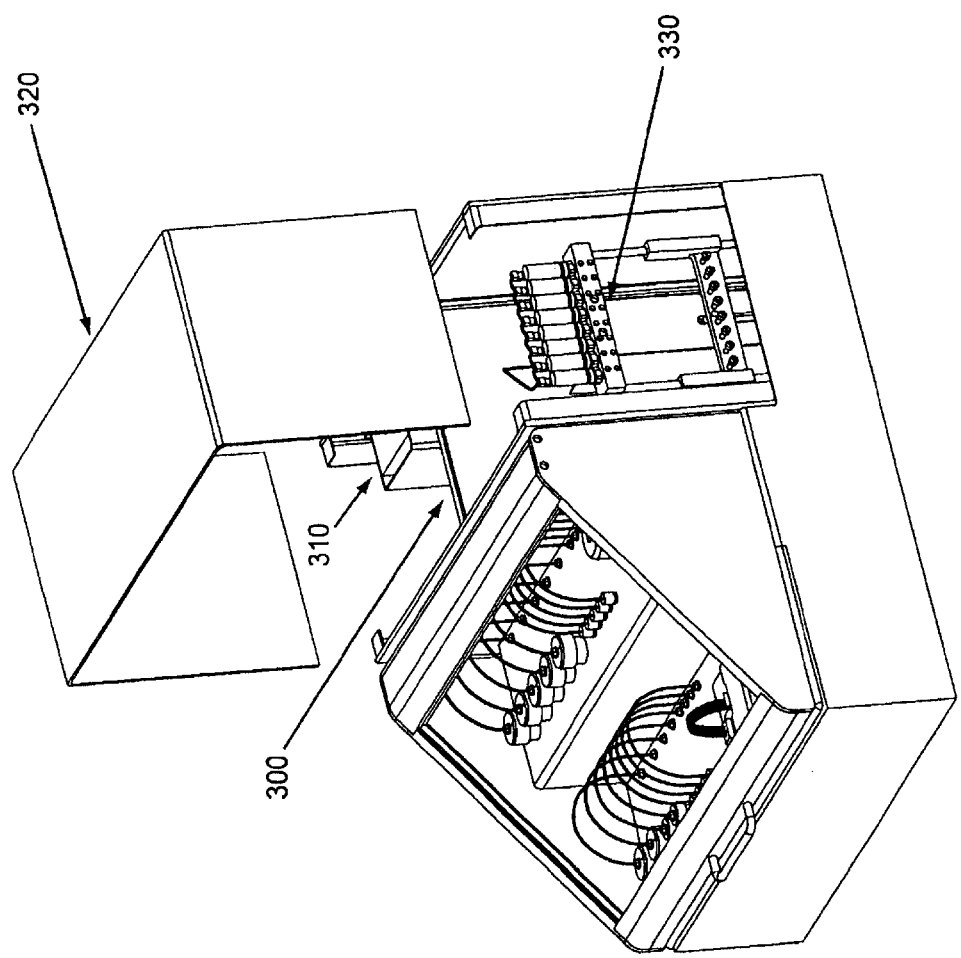
FIG. 3 displays an overview of the major exterior components and a partial overview of the major interior components of an exemplary embodiment of the invention.
Figure 4:
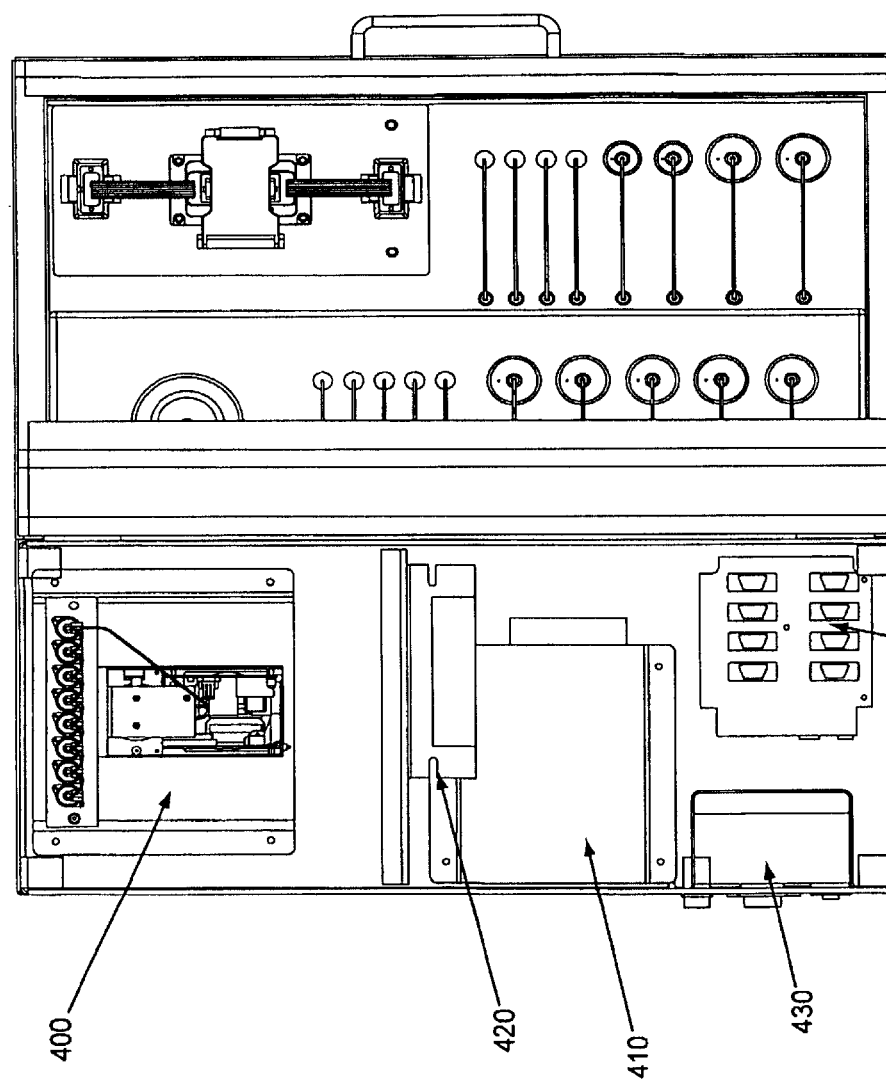
FIG. 4 displays a partial cut away view (top) of an exemplary embodiment of the invention.
Figure 5:
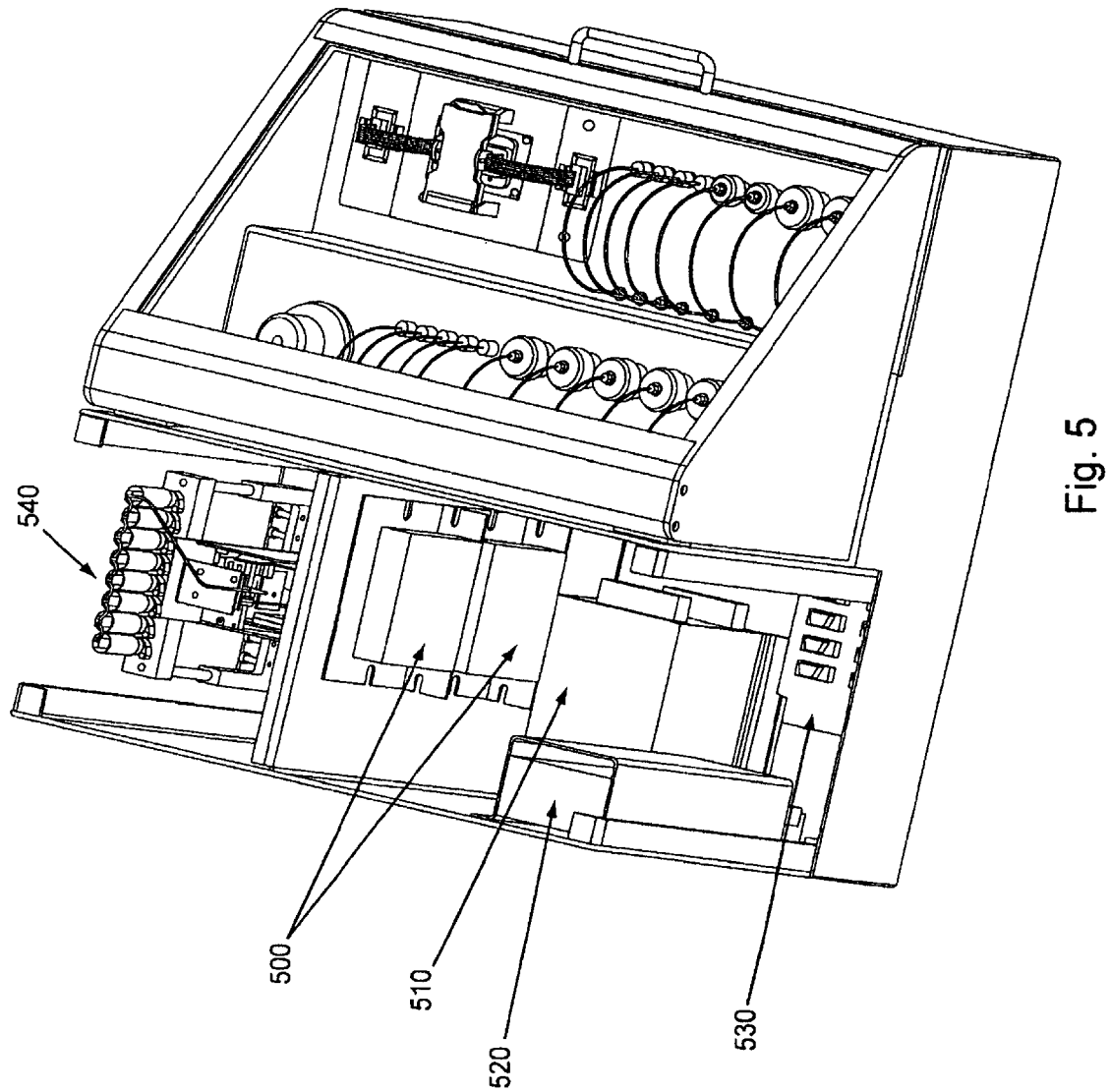
FIG. 5 displays a partial cut away view of an exemplary embodiment of the invention.
Figure 6:
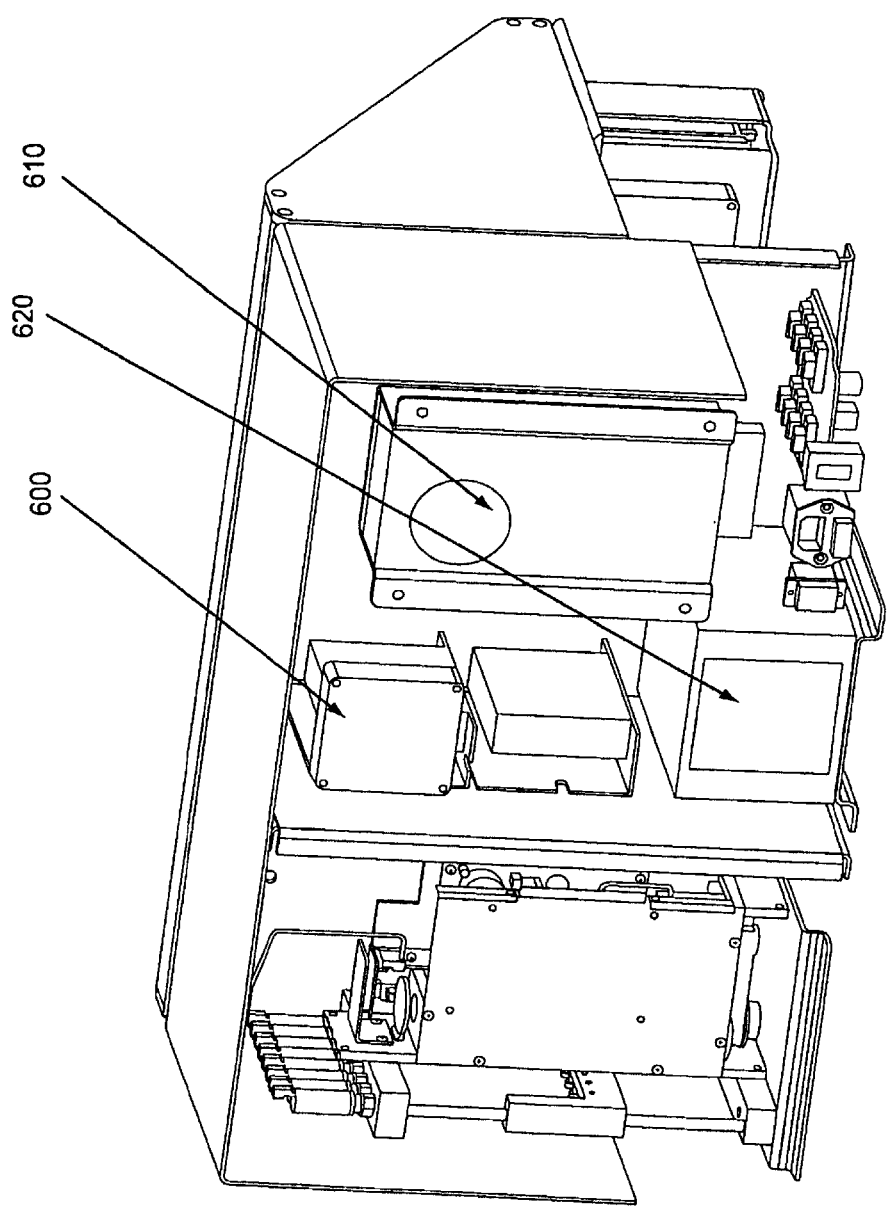
FIG. 6 displays a partial cut away rear view of an exemplary embodiment of the invention.
Figure 7:
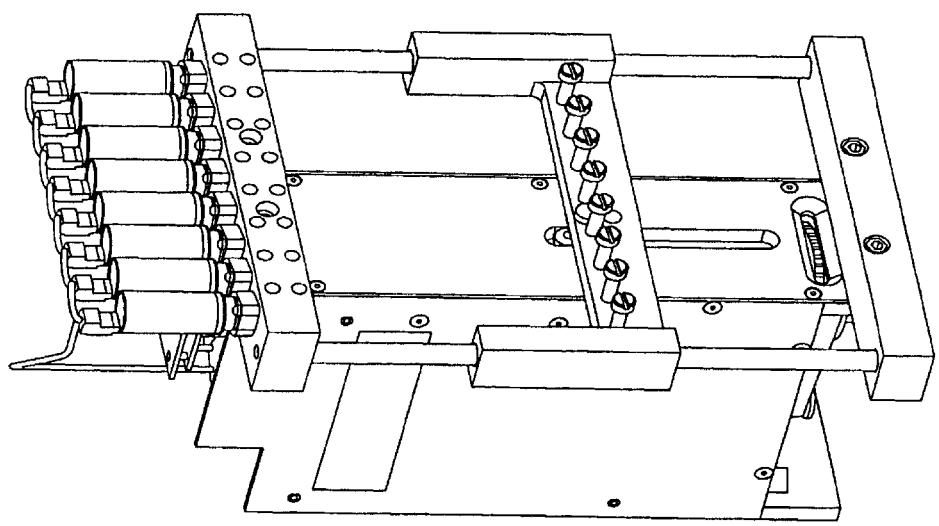
FIG. 7 displays an exemplary pump component of the invention shown in isolation without attached syringes, tubing, or other fluidic connections.

Overviews of the interior and of various interior components of an exemplary embodiment of the invention are shown in FIGS. 3 through 7. In FIG. 3, as can be seen once chassis cover 320 is removed, optional bulkhead 300 divides the interior of the device into separate areas, e.g., for fluidic and electronic components. Pump (here syringe pump) 330 can also be seen in FIG. 3, as well as part of power supply 310. FIG. 4 shows an interior top view of an exemplary embodiment of the invention showing: pump 400, power supplies 410 and 430 (illustrating that particular embodiments can comprise single or multiple power supplies, e.g., different power supplies for different components within the device), thermal controller 420, and USB to serial adaptor 440. FIG. 5 shows a top view of the same embodiment as shown in FIG. 4, with thermal controller 500, power supplies 510 and 520, USB to serial adapter 530, and pump 540. FIG. 6 shows a back interior view of the same embodiment as shown in FIGS. 4 and 5. As can be seen in FIG. 6, cooling fan 600 and power supply exhaust fans 610 and 620 act- to dissipate unwanted heat from the system/device (e.g., by expelling warm air, by pulling cool air across various heat sinks, etc.). FIG. 7 shows an isolated view (without. the fluidic connections, etc.) of an exemplary pump component that can be used in the current system/device. FIG. 24, Panels A and B, below give more detailed exemplary fluidic arrangements.

Individual components and the interaction of the various components of the invention are presented in more detail below.

Definitions

Before describing the present invention in detail, it is to be understood that the invention herein is not limited to use with particular nucleic acids or biological systems, which can, of course, vary. It is also to be understood that the terminology used herein is for the purpose of describing particular embodiments only, and is not necessarily intended to be limiting. As used in this specification and the appended claims, the singular forms "a," "an," and "the" include plural referents unless the context clearly dictates otherwise. Thus, for example, reference to "a manifold" optionally includes two or more manifolds, and the like. Other terms are defined throughout the specification.

The term "isothermal" as used herein refers to processes in which the temperature of a system or device remains constant, i.e., wherein ΔT=0. This optionally occurs when a system/device is in contact with an outside thermal reservoir (for example, a heater, a heat bath, thermoelectric controller (TEC), or the like), and actions or changes occur within the system/device at a rate that allows the system/device to continually adjust to the temperature of the reservoir through heat exchange.

The term "substantially isothermal" as used herein is therefore intended to mean that a system is maintained at essentially a constant or near constant temperature. The term also captures minor deviations in temperature that can occur, e.g., as the system/device equilibrates, for example, when components such as reaction reagents that are of lower or higher temperature than a flow cell are added to the flow cell. Thus it is intended that "substantially isothermal" includes minor deviations from the temperature initially selected for the system/device. The device of the invention typically acts to maintain a substantially constant temperature (substantially isothermal) during, e.g., the amplification reaction. In description throughout, the systems/devices of the invention and the methods of their use are often described as "isothermal" as a shorthand for "isothermal or substantially isothermal."

The term "amplifying" or "amplification" herein is intended to mean the process of increasing the number of a template polynucleotide sequence by producing copies of the template. The amplification process can be either exponential or linear, but is typically exponential. In exponential amplification, the number of copies made of the template polynucleotide sequence increases at an exponential rate. For example, in an ideal amplification reaction of 30 rounds, one copy of template DNA will yield $2^{30}$ or 1,073,741,824 copies. However, bridging amplification as described herein does not typically occur under ideal conditions, and a 30 cycle "exponential" reaction may only yield a few hundred to a few thousand copies of the original template, mainly due to the limited localized concentration of surface bound primers and the competition with template rehybridization. In linear amplification the number of copies made of the template polynucleotide sequences increases at a linear rate. For example, in an ideal 4-hour linear amplification reaction with a copying rate of 2000 copies per minute, each copy of template DNA will yield 480,000 copies.

As used herein, the terms "polynucleotide" or "nucleic acid" refer to deoxyribonucleic acid (DNA), however where appropriate, the skilled artisan will recognize that the systems and devices herein can also be utilized with ribonucleic acid (RNA). The terms should be understood to include, as equivalents, analogs of either DNA or RNA made from nucleotide analogs. The terms as used herein also encompass cDNA, that is complementary, or copy, DNA produced from an RNA template, for example by the action of reverse transcriptase.

The polynucleotide molecules to be amplified by the systems and devices herein can have originated in single-stranded form, as DNA or RNA or have originated in double-stranded DNA (dsDNA) form (e.g. genomic DNA fragments, PCR and amplification products and the like). Thus, a single stranded polynucleotide may be the sense or antisense strand of a polynucleotide duplex. Methods of preparation of single stranded polynucleotide molecules suitable for use in the systems/devices of the invention using standard techniques are well known in the art, for example heating or treatment with hydroxide followed by dilution. The precise sequence of the primary polynucleotide molecules is generally not material to the invention, and may be known or unknown. The single stranded polynucleotide molecules can represent genomic DNA molecules (e.g., human genomic DNA) including both intron and exon sequence (coding sequence), as well as non-coding regulatory sequences such as promoter and enhancer sequences.

In typical embodiments, the nucleic acid to be amplified through use of the current invention is immobilized upon a substrate (e.g., the surface of a channel within a flow cell). The term "immobilized" as used herein is intended to encompass direct or indirect, covalent or non-covalent attachment, unless indicated otherwise, either explicitly or by context. In certain embodiments of the invention, covalent attachment is preferred, but generally all that is required is that the molecules (e.g. nucleic acids) remain immobilized or attached to the support under conditions in which it is intended to use the support, for example in applications for amplification. The immobilized nucleic acid molecule for amplification can be obtained either by direct attachment of a suitably modified nucleic acid molecule (either single or double stranded) to a suitably reactive surface, or by hybridization to a surface immobilized primer, followed by a cycle of extension with a polymerase and dNTPs to copy the hybridized strand. The extended strand, or the chemically attached duplex, can then be subject to denaturing conditions to produce the desired immobilized, single stranded nucleic acid molecule that can then be subjected to cycles of isothermal amplification by the instrumentation described herein. The initial step of hybridizing the DNA from solution onto the flow cell can be performed at a higher temperature than the subsequent amplification reactions, which then take place at a substantially isothermal temperature. Thus the devices described herein can optionally have the capacity to heat to a higher temperature than the temperature used for the amplification process. In particular embodiments, the device does not actively cool the sample (e.g., the nucleic acids within the flow cell), so the initial hybridization step can be performed with passive cooling. The hybridization step may also be carried out at the amplification temperature, provided the input nucleic acids strands are supplied to the surface in a single stranded form.

The term "solid support" (or "substrate" in certain usages) as used herein refers to any inert substrate or matrix to which nucleic acids can be attached, such as for example glass, quartz, mica or fused silica surfaces, plastic surfaces, latex, dextran, polystyrene surfaces, polypropylene surfaces, polyacrylamide gel or other hydrogel surfaces, gold surfaces, and silicon wafers. In many embodiments, the solid support is a glass surface or plastic surface (e.g., the planar surface of a flow cell channel). In certain embodiments the solid support may comprise an inert substrate or matrix which has been "functionalized," for example by the application of a layer or coating of an intermediate material comprising reactive groups which permit covalent attachment to molecules such as polynucleotides. By way of non-limiting example such supports can include polyacrylamide hydrogels supported on an inert substrate such as glass. In such embodiments the molecules (polynucleotides) can be directly covalently attached to the intermediate material (e.g. the hydrogel) but the intermediate material can itself be non-covalently attached to the substrate or matrix (e.g. the glass substrate). Covalent attachment to a solid support is to be interpreted accordingly as encompassing this type of arrangement.

In particular embodiments, the single stranded polynucleotide molecule to be amplified by the invention has two regions of known sequence. Optionally, the regions of known sequence will be at the 5' and 3' termini of the single stranded polynucleotide molecule so that the single stranded polynucleotide molecule will be of the structure: 5' [known sequence I]-[target polynucleotide sequence]-[known sequence II]-3.' Typically "known sequence I" and "known sequence II" will consist of more than 20, or more than 40, or more than 50, or more than 100, or more than 300 consecutive nucleotides. The precise length of the two sequences may or may not be identical. The target sequences may vary between different members of a population of target molecules, whereas the known sequences can be universal to each of the members of the population and allow amplification of each of the different members of the population irrespective of the sequence of the target using the same pair of primers.

"Primer oligonucleotides" or "primers" are polynucleotide sequences that are capable of annealing specifically to the single stranded polynucleotide sequences to be amplified under conditions encountered in the primer annealing step of each cycle of an isothermal amplification reaction. Generally, amplification reactions require at least two amplification primers, often denoted "forward" and "reverse" primers. In certain embodiments the forward and reverse primers can be identical. The primer oligonucleotides can include a "template-specific portion," being a sequence of nucleotides capable of annealing to a primer-binding sequence in the single stranded polynucleotide molecule to be amplified (or the complement thereof when the template is viewed as a single strand) during the annealing step. The primer binding sequences generally will be of known sequence and will therefore particularly be complementary to a sequence within known sequence I and known sequence II of the single stranded polynucleotide molecule. The length of the primer binding sequences need not be the same as those of known sequence I or II, and can be shorter, e.g., 16-50 nucleotides, 16-40 nucleotides, or 20-30 nucleotides in length. The optimum length of the primer oligonucleotides will depend upon a number of factors and it is preferred that the primers are long (complex) enough so that the likelihood of annealing to sequences other than the primer binding sequence is very low.

In certain embodiments, the known sequences of the target nucleic acid comprise nucleic acid adapters that are ligated onto the ends of unknown nucleic acid fragments.

Cluster Stations

The systems/devices of the invention are typically used to isothermally amplify single stranded polynucleotide molecules. Description of methods to isothermally create nucleic acid clusters is found in co-pending applications WO/0246456, and "Isothermal Methods for Creating Clonal Single Molecule Arrays," U.S. Ser. No. 60/783,618, filed Mar. 17, 2006. Related methods of nucleic acid cluster formation that provide background information for use of the current invention, but using thermal amplification techniques, can also be found in WO/9844151 and WO/0018957. It will be appreciated, however, that while the systems/devices of the invention are primarily directed towards creation of nucleic acid cluster arrays that they are amenable to use for other purposes as well. For example, the systems/devices of the invention can also be used for myriad other chemical and biochemical reactions involving surface bound molecules.

Cluster Formation Methods

Briefly, in particular isothermal amplifications as performed by the systems/devices of the invention, double stranded "adapter" sequences are ligated to each end of DNA segments (e.g., randomly fragmented genomic double stranded DNA) that are to be amplified. The DNA-adapter molecules are then flowed into a flow cell where they randomly attach to the surface of the flow cell channels to form an array of single molecules. If the ligated adaptor sequences contain moieties for surface attachment, then the DNA-adaptor sequences can be attached directly to the surface. In such case, the attachment is generally performed with an excess of primers complementary to at least a portion of one of the adaptor sequences at each end of the ligated segment. The array will therefore be a lawn of primers suitable for polymerase extension, with a dispersion of discreet single molecules suitable for amplification. If desired, the primer attachment can be performed after the formation of the disperse array of single molecules for amplification. The DNA-adaptor molecules can be attached either in single or double stranded form, provided that the double stranded form can be treated to give a free single stranded molecule suitable for amplification.

In an alternative embodiment a surface bound lawn of primers is prepared on a flow cell surface for use in the system/device of the invention, followed by hybridization of the DNA-adaptor sequences to the surface immobilized primers, to form a single molecule array of hybridized DNA-adaptors. A cycle of extension with a polymerase and dNTPs to copy the hybridized strand, followed by denaturing of the original DNA-adaptor sequence produces the desired array of attached single DNA molecules in a single stranded form that can then be subjected to cycles of isothermal amplification by the current instrumentation as described.

The surface of the flow cell thus comprises a lawn of single stranded primer sequences, allowing "bridge amplification" to occur. In bridge amplification, when the surface is exposed to conditions suitable for hybridization, the single stranded nucleic acid molecules to be amplified form a bridge so that the adapter sequence on their free end hybridizes with its complementary single stranded primer sequence bound to the surface of the flow cell. Nucleotides and DNA polymerase are then transported into the flow cell to create the complementary strand of the nucleic acid to be amplified. The double stranded sequences created are then denatured by flowing in a denaturing reagent, and the process starts again, thus creating clusters of amplified nucleic acid without changing the temperature of the system during the amplification cycles. In typical embodiments, the majority of the clusters are monoclonal, resulting from the amplification of a single original nucleic acid sequence.

Generally primer oligonucleotides used to create DNA clusters are single stranded polynucleotides. They may also contain a mixture of natural and non-natural bases as well as natural and non-natural backbone linkages, provided that any non-natural modifications do not preclude function as a primer (i.e., the ability to anneal to a template polynucleotide strand during conditions of the amplification reaction and to act as an initiation point for synthesis of a new polynucleotide strand complementary to the template strand). One of the primers may contain a modification allowing the primer to be removed (cleaved) from the surface to allow the formation of single stranded clusters. Such linearized clusters can undergo hybridization with a further primer strand to allow a sequencing reaction to occur.

"Solid-phase amplification" as used herein refers to nucleic acid amplification reactions carried out on, or in association with, a solid support (e.g., the surface of a channel of a flow cell) so that all or a portion of the amplified products are immobilized on the solid support as they are formed.

Although the systems/devices of the invention can be used for solid-phase amplification in which only one amplification primer is immobilized, such requires a template to have the same adaptor sequence on both ends of each fragment. In particular embodiments, it is preferred for the solid support to be provided with the two different forward and reverse primers immobilized on it. The surface is generally treated with an excess of the coupling primers in solution to obtain a lawn of the immobilized primers on the surface since the amplification process requires an excess of primers to sustain amplification.

In use of the system/devices herein to amplify nucleic acid, primers for solid phase amplification are immobilized by covalent attachment to the solid support of the flow cell at or near the 5' end of the primer, leaving the template-specific portion of the primer free for annealing to its cognate template and the 3' hydroxyl group free for primer extension. The chosen attachment chemistry will depend on the nature of the solid support, and any functionalization or derivitization applied to it. The primer itself may include a moiety, which may be a non-nucleotide chemical modification to facilitate attachment. The primer can include a sulphur containing nucleophile such as phosphoriothioate or thiophosphate at the 5' end. In the case of solid supported polyacrylamide hydrogels, this nucleophile can bind to a bromoacetamide group present in the hydrogel. For example, the primers can be attached to the solid support via 5' thiophosphate attachment to a hydrogel comprised of polymerized acrylamide and N-(5-bromoacetamidylpentyl) acrylamide (BRAPA).

The polynucleotides to be amplified by the devices/systems of the invention and the primer oligonucleotides are immobilized in appropriate proportions so that when they are attached to the solid support of the flow cell an appropriate density of attached single stranded polynucleotide molecules and primer oligonucleotides is obtained. In the case of directly immobilized DNA-adaptor sequences, the proportion of primer oligonucleotides in the solution mixture used for the immobilization reaction is higher than the proportion of single stranded polynucleotide molecules. The immobilization reaction can then give a lawn of primers, with discreet single molecules of DNA-adaptor sequences. For the hybridized DNA-adaptor reactions, the density of clusters is controlled by the concentration of the DNA-adaptor sequences used to hybridize to the lawn of primers. The ratio of primer oligonucleotides to single stranded polynucleotide molecules is typically such that when immobilized to the solid support a "lawn" of primer oligonucleotides is formed, comprising a plurality of primer oligonucleotides being located at an approximately uniform density over the whole or a defined area of the flow cell channel with one or more single stranded polynucleotide molecules being immobilized individually at intervals within the lawn of primer oligonucleotides.

The target polynucleotide(s) to be amplified using the systems/devices of the invention may be any polynucleotide. It is possible to start from essentially any double or single-stranded target polynucleotide of known, unknown or partially known sequence, provided that the ends of the sequence are treated to attach a known sequence that can undergo hybridization with surface bound primers.

The distance between the individual primer oligonucleotides and the single stranded polynucleotide molecules (and hence the density of the primer oligonucleotides and single stranded polynucleotide molecules) can be controlled by altering the concentration of primer oligonucleotides and single stranded polynucleotide molecules that are immobilized to the support.

The terms "denature" and "denaturation" are broad terms which refer primarily to the physical separation of the DNA bases that interact within for example, a Watson-Crick DNA-duplex of the single stranded polynucleotide sequence and its complement. The terms also refer to the physical separation of both of these strands. In their broadest sense the terms refer to the process of creating a situation wherein annealing of another primer oligonucleotide or polynucleotide sequence to one or both of the strands of a duplex becomes possible.

Once the primer oligonucleotides and single stranded polynucleotide molecules of the invention have been immobilized on the solid support at the appropriate density, extension products can then be generated by carrying out cycles of isothermal amplification on the covalently bound single stranded polynucleotide molecules so that each colony comprises multiple copies of the original immobilized single stranded polynucleotide molecule (and its complementary sequence). One cycle of amplification consists of the steps of hybridization, extension and denaturation. Such steps are generally comparable in terms of reagent components (e.g., buffers, etc.) with traditional nucleic acid amplification procedures such as PCR. Suitable reagents for amplifying nucleic acids (e.g., hybridization, extension, etc.) are well known in the art. Exemplary reagents are described in more detail below.

Thus a neutralizing/hybridizing buffer can be applied to the single stranded polynucleotide molecules and the plurality of primer oligonucleotides such that the unbound end of a surface bound single stranded polynucleotide molecule hybridizes to a surface bound primer oligonucleotide to form a complex (wherein the primer oligonucleotide hybridizes to and is complementary to a region or template specific portion of the single stranded polynucleotide molecule). This process creates a "bridge" structure. Again, see WO/0246456, U.S. Ser. No. 60/783,618, WO/9844151, and WO/0018957 for further discussion on bridge amplification.

Suitable neutralizing/hybridizing buffers are well known in the art (See Sambrook et al., Molecular Cloning, A Laboratory Manual, 3rd Ed, Cold Spring Harbor Laboratory Press, NY; Current Protocols, eds Ausubel et al.) as well as the illustration section describing amplification below. Suitable buffers may comprise additives such as betaine or organic solvents to normalize the melting temperate of the different template sequences, and detergents. An exemplary hybridization buffer comprises 2 M betaine, 20 mM Tris, 10 mM Ammonium Sulfate, 2 mM Magnesium sulfate, 0.1% Triton, 1.3% DMSO, pH 8.8. See below.

Next, an extension reaction is done by applying an extension solution comprising an enzyme with polymerase activity and dNTPs to the bridge complexes. The primer oligonucleotide of the complex is extended by sequential addition of nucleotides to generate an extension product complimentary to the single stranded polynucleotide molecule. Suitable extension buffers/solutions are well known in the art (See, e.g., Sambrook et al., Molecular Cloning, A Laboratory Manual, $3^{rd}$ Ed, Cold Spring Harbor Laboratory Press, NY; Current Protocols, eds Ausubel et al) and examples below.

Examples of enzymes with polymerase activity that can be used in the systems/devices of the invention include DNA polymerase (Klenow fragment, T4 DNA polymerase) and heat-stable DNA polymerases from a variety of thermostable bacteria (such as Taq, VENT, Pfu, Bst and Tfl DNA polymerases) as well as their genetically modified derivatives (TaqGold, VENT exo, Pfu exo, etc.). It will be appreciated that since the amplification reactions performed by the instrumentation herein are isothermal, that additional and/or alternative DNA polymerases can be used as compared to the polymerases for thermal cycling amplification, and, in preferred embodiments, there is no particular requirement for the polymerase to be thermostable. Also, while enzymes with strand displacing activity such as Bst polymerase show excellent performance in growing effective clusters for sequencing, any DNA polymerase can be used.

The nucleoside triphosphate molecules used to create DNA clusters with the current invention are typically deoxyribonucleotide triphosphates, for example dATP, dTTP, dCTP, dGTP. The nucleoside triphosphate molecules may be naturally or non-naturally occurring.

After the hybridization and extension steps, the support and attached nucleic acids are subjected to denaturation conditions. Suitable denaturing buffers are well known in the art (See, e.g., Sambrook et al., Molecular Cloning, A Laboratory Manual, 3rd Ed, Cold Spring Harbor Laboratory Press, NY; Current Protocols, eds Ausubel et al.). The systems/devices of the current invention produce isothermal nucleic acid amplification, therefore, the nucleic acid strands herein are not denatured through temperature elevation or manipulation, but rather by other means (e.g., chemical, physical, etc.). By way of example it is known that alterations in pH and low ionic strength solutions can denature nucleic acids at substantially isothermal temperatures. Formamide and urea form new hydrogen bonds with the bases of nucleic acids disrupting hydrogen bonds that lead to Watson-Crick base pairing. These result in single stranded nucleic acid molecules. Alternatively the strands can be separated by treatment with a solution of low salt and high pH (>12) or by using a chaotropic salt (e.g. guanidinium hydrochloride). In a particular embodiment, sodium hydroxide (NaOH) solution is used at a concentration of from about 0.25M to about 0.1M. In an alternate embodiment 95% formamide in water, or 100% formamide is used. Such formamide embodiments show additional advantages as the hydroxide treatment can damage the surface and give clusters of lower intensity in some instances. As with the other reagents used, such denaturing reagents are passed through the flow channels by the current invention. See below.

Following denaturation, two immobilized nucleic acids will be present, the first being the initial immobilized single stranded polynucleotide molecule and the second being its complement, extending from one of the immobilized primer oligonucleotides. Both the original immobilized single stranded polynucleotide molecule and the immobilized extended primer oligonucleotide (the complement) formed are then able to initiate further rounds of amplification by subjecting the support to further cycles of hybridization, extension and denaturation. Such further rounds of amplification will result in a nucleic acid colony or "cluster" comprising multiple immobilized copies of the single stranded polynucleotide sequence and its complementary sequence. The initial immobilization of the single stranded polynucleotide molecule means that the single stranded polynucleotide molecule can only hybridize with primer oligonucleotides located at a distance within the total length of the single stranded polynucleotide molecule. Thus the boundary of the nucleic acid colony or cluster formed is limited to a relatively local area in which the initial single stranded polynucleotide molecule was immobilized.

The systems/devices of the current invention can also perform optional washing steps in between each step of the amplification method. For example an extension buffer without polymerase enzyme or dNTPs can be applied to the solid support before being removed and replaced with the full extension buffer.

A feature of the invention is that the hybridization, extension and denaturation steps are all carried out at the same, substantially isothermal temperature by the systems/devices of the invention. Preferably the temperature is from 37° C. to about 75° C., or from 50° C. to 70° C., or from 60° C. to 65° C. In some embodiments, the temperature is approximately 38° C., in other embodiments the temperature is approximately 60° C. which can produce cleaner clusters suitable for sequencing. In a particular embodiment, the substantially isothermal temperature is defined by the optimal working temperature of a particular DNA polymerase, or by the annealing temperature of the oligonucleotide primer(s). The annealing temperature may be about 5° C. below the melting temperature (Tm) of the oligonucleotide primers. Methods of calculating appropriate melting temperatures are well known in the art. For example the formula: Tm=64.9° C.+41° C.×(number of Gs and Cs in the primer-16.4)/N (where N is the length of the primer) can be used to calculate melting points. In yet another particular embodiment the substantially isothermal temperature may be determined empirically as the temperature at which the oligonucleotide displays greatest specificity for the primer binding site while reducing non-specific binding.

Problems of traditional thermal cycling can be overcome by performing solid-phase amplification under substantially isothermal conditions (as with use of the current invention) and not heating the reaction to high temperatures such as 95° C. Changing the solutions in contact with the solid support as is done by the invention, renews the components of the reactions, which may be rate limiting, such as the enzyme or dNTPs and lower temperature of the isothermal application can result in greater stability of the surface and brighter clusters during downstream sequencing.

In sum, the systems/devices of the invention are used to prepare clustered arrays of nucleic acid colonies, analogous to those described in WO/0246456, WO/0018957 and WO/9844151, the contents of each of which are incorporated herein by reference in their entirety, by solid-phase amplification but under substantially isothermal conditions. The terms "cluster" and "colony" are used interchangeably herein to refer to a discrete site on a solid support comprised of a plurality of identical immobilized nucleic acid strands and a plurality of identical immobilized complementary nucleic acid strands. The term "clustered array" or "cluster array" refers to an array formed from such clusters or colonies. In this context the term "array" is not to be understood as requiring an ordered arrangement of clusters.

Component Variation and Interaction

As indicated above, the present invention comprises novel systems and devices for isothermal creation of nucleic acid clusters on solid phase support (e.g., in flow cells). The inventors and coworkers have described various additional aspects regarding nucleic acid cluster formation procedures and methods in, e.g. "Isothermal Methods for Creating Clonal Single Molecule Arrays," U.S. Ser. No. 60/783,618, filed Mar. 17, 2006; WO/0246456, WO/0018957, and "Systems and Devices for Sequence by Synthesis Analysis," U.S. Ser. No. 60/788,248, filed Mar. 31, 2006 and PCT/US2007/007991, filed Mar. 30, 2007. Also, it will be appreciated by those of skill in the art that many reagents for traditional thermal nucleic acid amplification (e.g., PCR, etc.) are also applicable to isothermal amplification using the current invention. For example, typical buffers, nucleotides, and enzymes commonly used in thermal nucleic acid amplification can also be used with isothermal amplification using the current invention. Those of skill in the art will be quite familiar with such buffers, reagents, etc. See, e.g., Sambrook et al., Molecular Cloning, A Laboratory Manual, 3$^{rd}$ Ed, Cold Spring Harbor Laboratory Press, NY; Current Protocols in Molecular Biology, 5$^{th}$ Edition, Ausubel et al., John Wiley & Sons, NY, etc. Exemplary protocols to enable the isothermal preparation of clustered arrays are given in the illustrations below.

The embodiments of the current invention typically comprise a number of different components or component areas. As described earlier, the current invention typically comprises, e.g., a body or chassis, a flow cell and flow cell holder, one or more manifolds that can be fluidly connected to the flow cell, reagent storage and waste storage reservoirs (all or some of which optionally can be temperature controlled and all of which typically can be fluidly connected to the manifold/flow cell), sample storage areas, fluidic distribution systems (e.g., tubing, pumps, directional valves, etc.), temperature control components (e.g., for keeping the flow cell isothermal during cluster creation or for keeping reagents at the proper temperature), power supply, computer, etc.

As mentioned throughout, the current invention can vary between embodiments (e.g., in number and type of components or subsystems as well as in configuration of the various components). As previously stated, the systems/devices described herein comprise various combinations of mechanical, fluidic, thermal, electrical, and computing components/aspects. Thus, even though in certain embodiments described herein the invention is directed towards particular configurations and/or combinations of components, those of skill in the art will appreciate that not all embodiments necessarily comprise all components or particular configurations (unless specifically stated to do so).

Flow Cells and Flow Cell Holders

The systems/devices of the current invention create nucleic acid clusters isothermally upon the substrate surface of channels in flow cells. See, e.g., FIG. 8A.

The flow cells used in the various embodiments herein can comprise millions of individual nucleic acid clusters, e.g., about 2-8 million imageable clusters per channel, where the channel has a dimension of 0.1 mm depth by 1.1 mm width by 6 cm in length. Previous work by the inventor and coworkers has described different types of flow cells and their uses. See, e.g., "Systems and Devices for Sequence by Synthesis Analysis," U.S. Ser. No. 60/788,248, filed Mar. 31, 2006 and PCTIUS2007/007991, filed Mar. 30, 2007, and Fedurco et al; Nucleic Acids Research; 2006; 34(3):e22, for further information on flow cells in creation and use of nucleic acid clusters. While particular flow cell designs and constructions are described and shown herein, such descriptions should not necessarily be taken as limiting; other flow cells can comprise different materials, dimensions and designs than those presented herein.

It will be appreciated that, as described in the above cited sources, flow cells can vary from embodiment to embodiment in terms of construction material, e.g., glass; photosensitive glass(es) such as Foturan® or Fotoform® that can be formed and manipulated as necessary; plastics such as cyclic olefin copolymers (e.g., Topas® or Zeonor®); etc. Additionally, the number of channels in different flow cells is also variable. Thus, particular flow cells can comprise 1 channel, 2 channels, 3 channels, or 4, 8, 10, or 12 channels or more. As explained more fully below, the individual channels of the flow cells herein match up with individual tubes from manifold(s), thus allowing different nucleic acid samples (optionally comprising many different nucleic acid sequences) to be amplified in each channel.

As outlined below, the flow cells in which the nucleic acid clusters are grown are placed within an appropriate flow cell holder area. To perform the amplification cycles, the appropriate buffers, nucleotides, DNA polymerase, denaturing solutions etc., are flowed into/through the flow cell (and the manifold) by the fluid flow system.

Figure 8B:
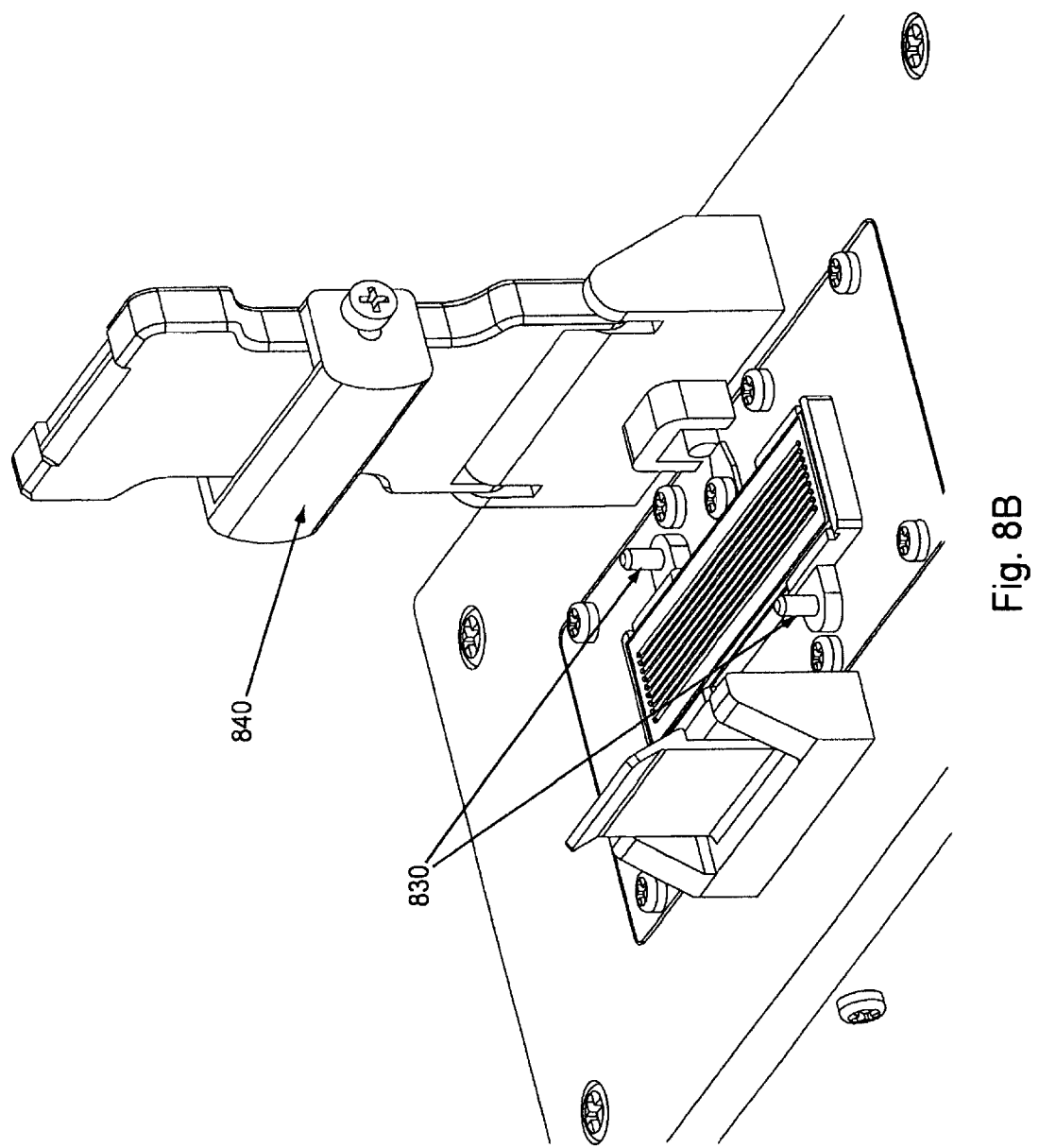
FIG. 8B illustrates a flow cell placed upon a flow cell placement area.

Placement of the flow cell (and thus the nucleic acid clusters to be sequenced) is controlled and secured by a flow cell holder. FIGS. 8A through 8H display diagrams in isolation of an exemplary flow cell and flow cell holder of the current system. Placement of the flow cell and flow cell holder with the other components of an exemplary embodiment of the current invention is shown in FIG. 1. FIG. 8A shows flow cell 800 being placed onto flow cell placement area 820. The flow cell placement area comprises, or is in thermal contact with, one or more temperature control component, e.g., a Peltier, etc. See below. Such temperature control or regulation component keeps the flow cell, and thus, the nucleic acid amplification reactions with the flow cell, at the proper temperature (e.g., isothermal during the cluster creation reaction). Flow cell holder 810 is shown in the "open" position displaying compression bar 840 (which comprises, e.g., a spring force enabled bar) that, when the flow cell holder is closed, pushes down upon the manifold and flow cell to create a tight seal between the fluidic connections of the flow cell and manifold and also which creates maximum surface contact between the flow cell and the temperature control element underneath it.

FIG. 8B shows the flow cell placed upon the flow cell placement area and properly aligned by manifold alignment pins 830 (which can also act to help properly align the manifold when it is placed upon the flow cell).

Figure 8C:
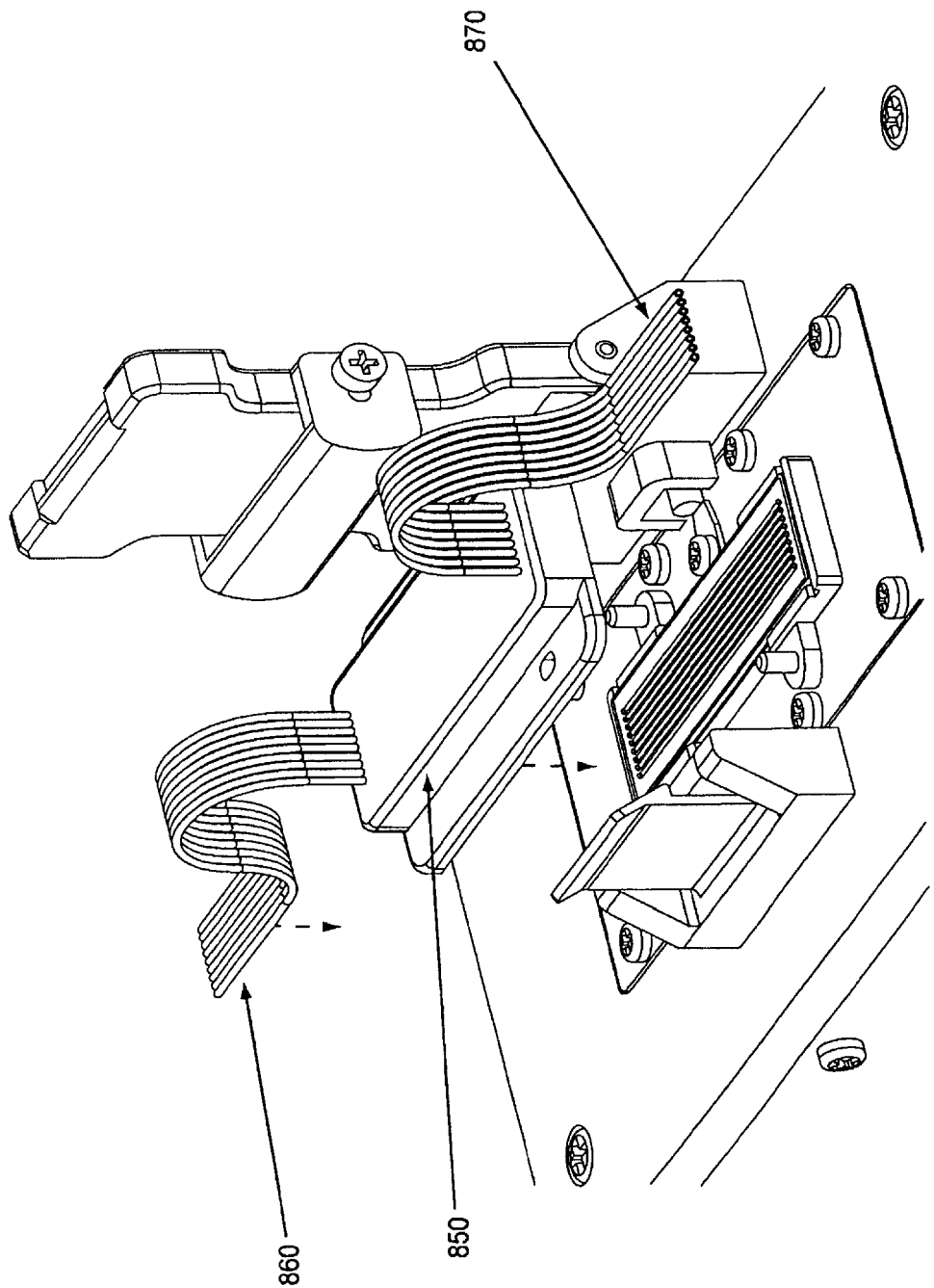
FIG. 8C illustrates an exemplary manifold being placed upon the flow cell in the flow cell holder.

FIG. 8C shows exemplary manifold 850 (here a cut away of a reagent manifold) being placed upon the flow cell in the flow cell holder. Proximal tubing 860 fluidly connects the manifold (and hence the flow cell) with the proper reagent storage reservoirs via a manifold attachment site (see, e.g., FIG. 12). Distal tubing 870 fluidly connects the manifold and flow cell with a waste reservoir. As can be seen from FIG. 8C, the exemplary manifold comprises a main body that snugly fits upon the flow cell. Once the manifold and the flow cell are properly aligned with one another, fluidic connections are formed between individual proximal tubes and individual flow cell channels that allow reagents, nucleotides, etc. to be flowed from their storage reservoirs into different channels of the flow cell and eventually out of the flow cell and into the waste reservoir. As used herein, tubing is described as "proximal" if it transports fluids or reagents prior to their entry into the flow cell. Correspondingly, tubing that transports fluid/reagents away from the flow cell after such fluid has been transported 'through the flow cell is described herein as "distal."

Figure 8D:
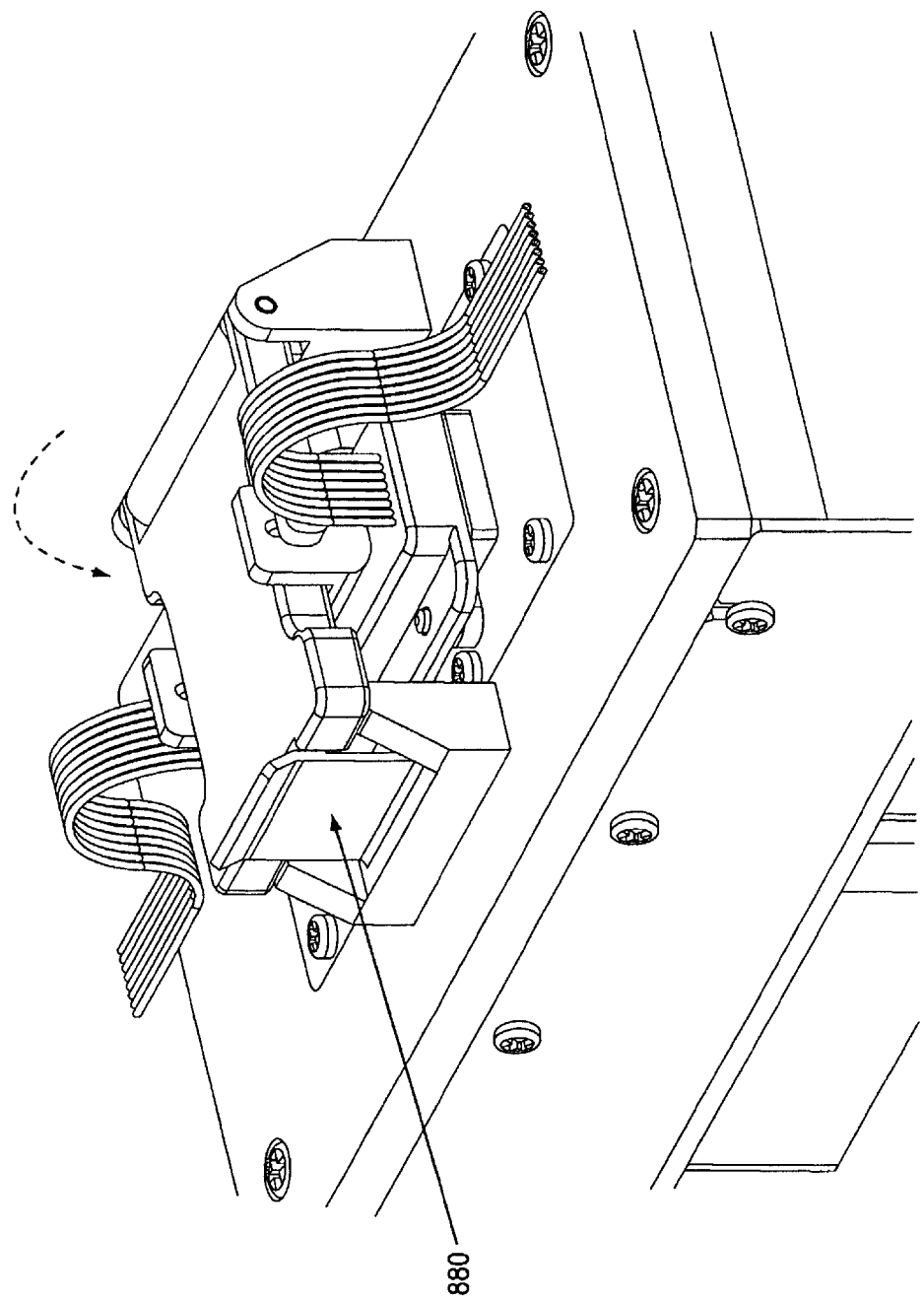
FIG. 8D displays the flow cell holder in a closed position.
Figure 8E:
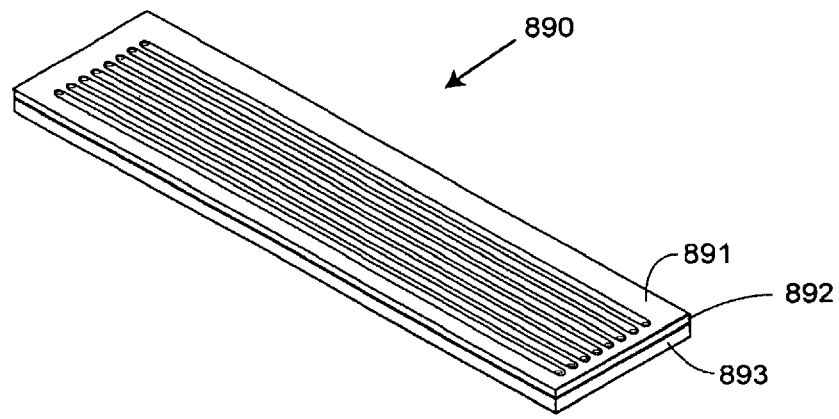
FIG. 8E is a perspective view of an exemplary flow cell.
Figure 8F:
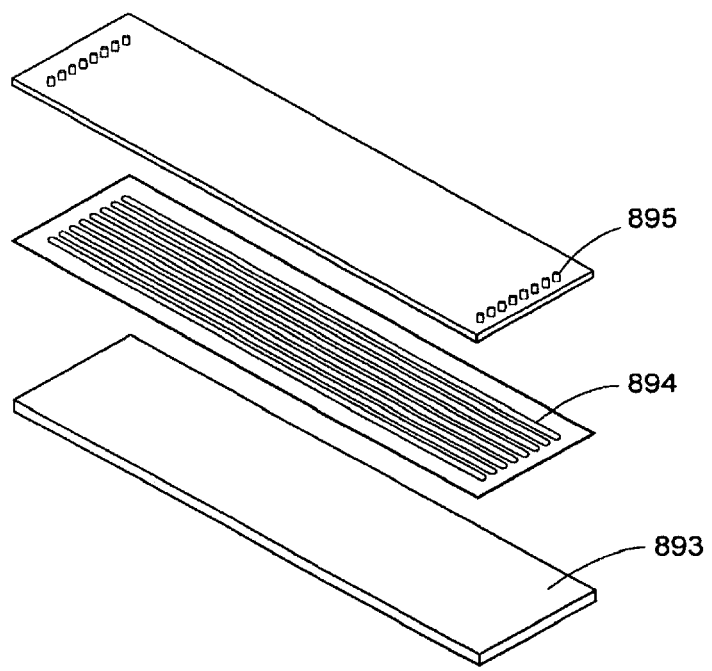
FIG. 8F is an exploded view of the flow cell of FIG. 8E.
Figure 8G:
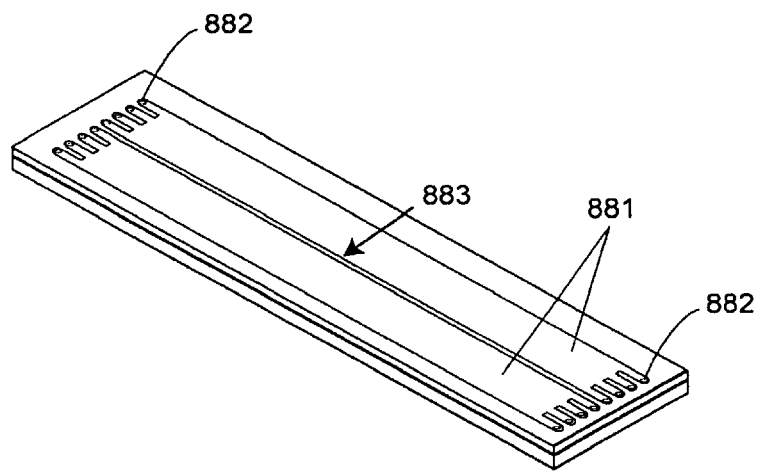
FIG. 8G is a perspective view of an exemplary flow cell.
Figure 8H:
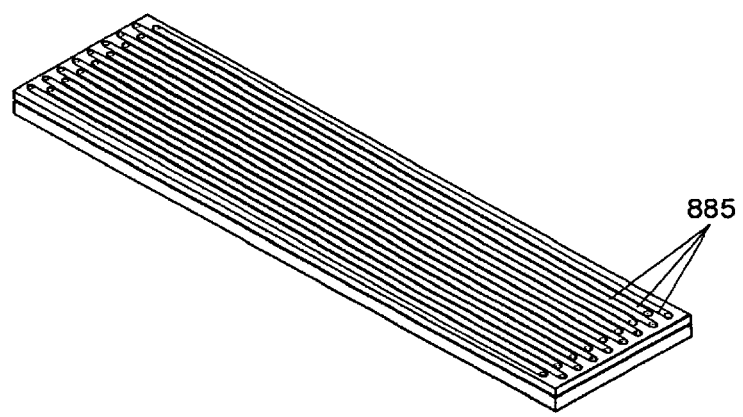
FIG. 8H is a perspective view of an exemplary flow cell.

FIG. 8D displays the flow cell holder in the "closed" position, thus securely holding the flow cell and manifold against the flow cell placement area which is, or which is in thermal communication with, a temperature control device such as a Peltier or other thermoelectric cooler (TEC), heating block, or similar device to produce and maintain the proper temperature conditions (e.g., isothermal conditions during amplification). Also seen in FIG. 8D, clamp handle 880 is shown fastening the flow cell holder down, thus, securing the flow cell holder. It will be appreciated that when closed, the compression bar of the flow cell holder exerts a pressure (e.g., through a spring or the like) that securely nestles the components (flow cell and manifold) together and helps ensure proper orientation, contact, and fluidic connections.

FIGS. 8E through 8H display various exemplary embodiments of flowcells. As can be seen, flowcell 890 comprises base layer 893 (e.g., of borosilicate glass 1000 µm in depth), channel layer 892 (e.g., of etched silicon 100 µm in depth) overlaid upon the base layer, and cover, or top, layer 891 (e.g., 300 µm in depth). When the layers are assembled together, enclosed channels 894 are formed having inlet/outlets holes 895 at either end through the cover.

The channeled layer can optionally be constructed using standard photolithographic methods, with which those of skill in the art will be familiar. One such method which can be used with the current invention, involves exposing a 100 µm layer of silicon and etching away the exposed channel using Deep Reactive Ion Etching or wet etching.

It will be appreciated that while particular flowcell configurations are present herein, such configurations should not necessarily be taken as limiting. Thus, for example, various flowcells herein can comprise different numbers of channels (e.g., 1 channel, 2 or more channels, 4 or more channels, or 6, 8, 10, 16 or more channels, etc. Additionally, various flowcells can comprise channels of different depths and/or widths (different both between channels in different flowcells and different between channels within the same flowcell). For example, while the channels formed in the cell in FIG. 8 may be 100 μm deep, other embodiments can optionally comprise channels of greater depth (e.g., 500 μm) or lesser depth (e.g., 50 μm). Additional exemplary flowcell designs can comprise wider channels, such as channels 881 in FIG. 8G, which flow cell has two channels with 8 inlet and outlet ports (ports 882—8 inlet and 8 outlet) to maintain flow uniformity and a center wall, such as wall 883, for added structural support. Flowcells can also comprise offset channels, such as the 16 offset channels (channels 885 shown in FIG. 8H). It will be appreciated that the number of proximal and distal tubes in a manifold will typically vary in relation with the number of channels in the flow cell, e.g., 8 channels—8 proximal and 8 distal tubes, etc.

While the example in FIG. 8 shows a flowcell comprised of 3 layers, other embodiments can comprise 2 layers, e.g., a base layer having channels etched/ablated/formed within it and a top cover layer, or a base layer with a top layer which has channels formed within it, etc. Additionally, other embodiments can comprise flowcells having only one layer which comprises the flow channel etched/ablated/otherwise formed within it.

Manifolds

In the various embodiments herein and/or at various times during usage of the current invention to produce nucleic acid clusters, different manifolds are optionally used to properly guide samples and reagents into and through the flow cell and/or around the flow cell. Three major configurations or types of manifolds include: sample manifolds (see, e.g., FIG. 9); common solution or reagent manifolds (see, e.g., FIG. 11A); and wash connections (see, e.g., FIG. 13). The tubing aspect of the various manifolds herein can comprise, e.g., Teflon® while the body of the manifolds can comprise, e.g., polycyclicolefin or the like.

Figure 9:
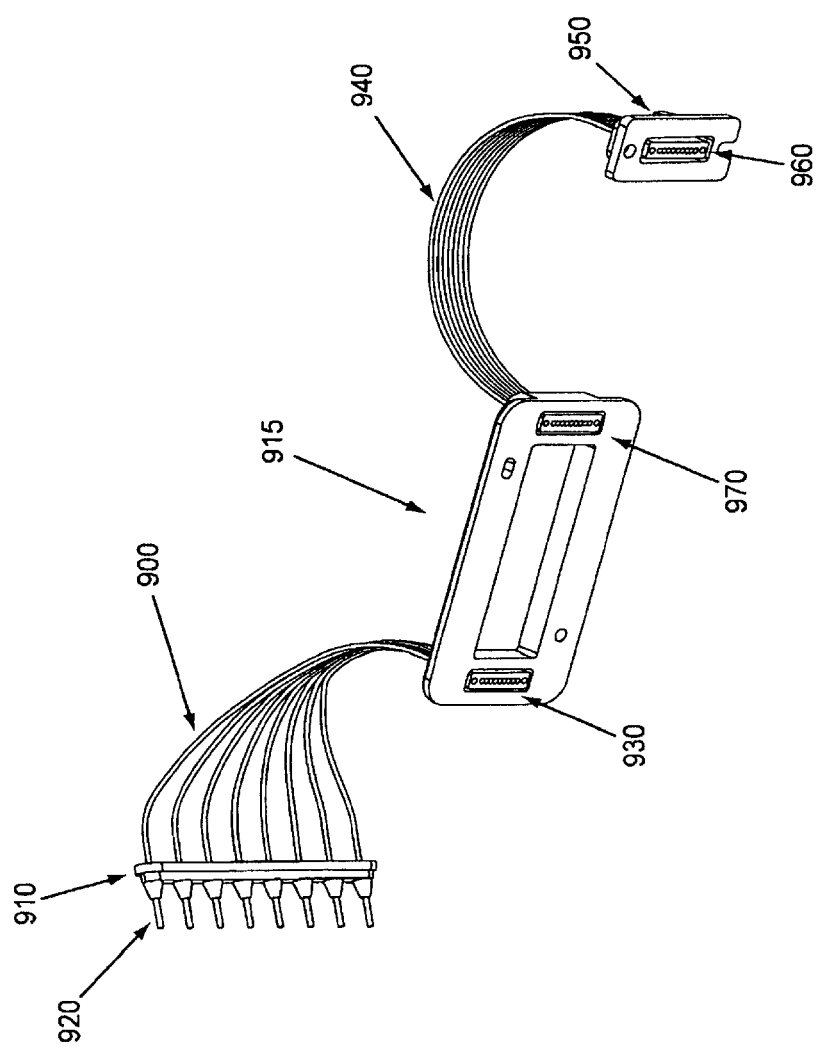
FIG. 9 displays an exemplary sample manifold of the invention.
Figure 10:
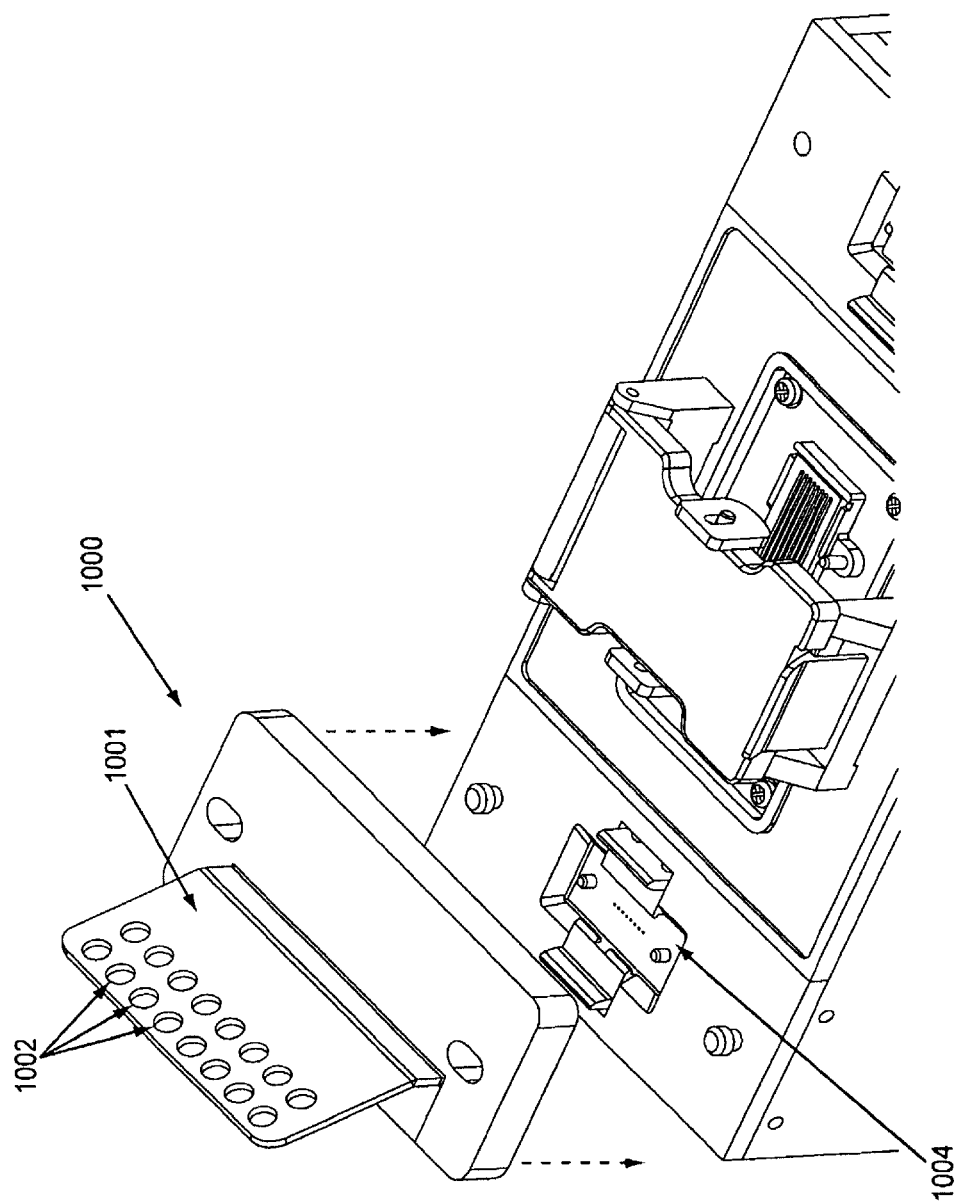
FIG. 10 displays an exemplary sample holder of the invention and placement of it in relation to a manifold attachment area.

FIG. 9 shows an exemplary embodiment of a sample manifold. Because the invention is used to amplify nucleic acids, even small amounts of nucleic acid contamination can be of concern. Therefore, when initial nucleic acid samples are loaded into the different channels of the flow cell (see above), they are loaded through a specific manifold used only for that purpose which is then discarded or removed after its use. This, thus, helps ensure that nucleic acid does not enter into areas of the device where it is not desired (e.g., a wrong sample in a wrong channel, nucleic acid contamination in one or more common reagent reservoir, etc.). In FIG. 9, tube ends 920 of proximal tubes 900 each enter into a different nucleic acid sample storage area (typically one proximal tube end per sample area). The tube ends can be arranged in a strip which in some embodiments can act to seal the sample reservoirs. Cf. FIG. 10. Thus, FIG. 9 shows sealing strip 910 which can hold the proximal tube ends into the different sample reservoirs while sealing them and helping prevent cross-contamination. Proximal tubes 900 fluidly connect the tube ends in the sample reservoirs with main body of the manifold 915. The proximal tubes have openings 930 on the underside of the main body of the manifold that match up with the different channels of the flow cell. Typically, each proximal tube opening will create one fluidic connection with one channel in the flow cell. Distal tubes 940 fluidly connect the opposing ends of the channels of the flow cell to a waste storage area. The openings 970 of the distal tubes that are in contact with the main body of the manifold match up with the individual channels of the flow cell. The ends 960 of the distal tubes away from the body of the manifold are held and orientated by distal manifold plug 950 and open into the waste disposal fluidics. See below.

FIG. 10 shows removable sample holder 1000 being placed upon manifold attachment area 1004. As can be appreciated, when the sample holder is placed on the manifold attachment area, there are no fluid connections from the openings in the manifold attachment area (which lead via fluidic connections to the reagent storage areas) and the ends of the proximal tubes of the manifold. Instead, the ends of the proximal tubes of the manifold enter into sample storage reservoirs (not shown) that are positioned in holes 1002 in plate 1001. See, FIG. 1 for position of the sample holder and sample storage reservoirs. It will be appreciated that the current invention can also comprise embodiments that comprise sample reservoirs that are differently configured. For example, in some embodiments, the nucleic acid sample reservoirs can be located outside of, but still in fluid connection with, the current device/system. In typical embodiments, however, no matter the location or configuration of the sample reservoir(s), because of contamination concerns, the sample manifold is optionally removed or discarded after the nucleic acid samples to be amplified are flowed into the flow cell after which a common solution or reagent manifold is optionally attached. See below.

Figure 11A:
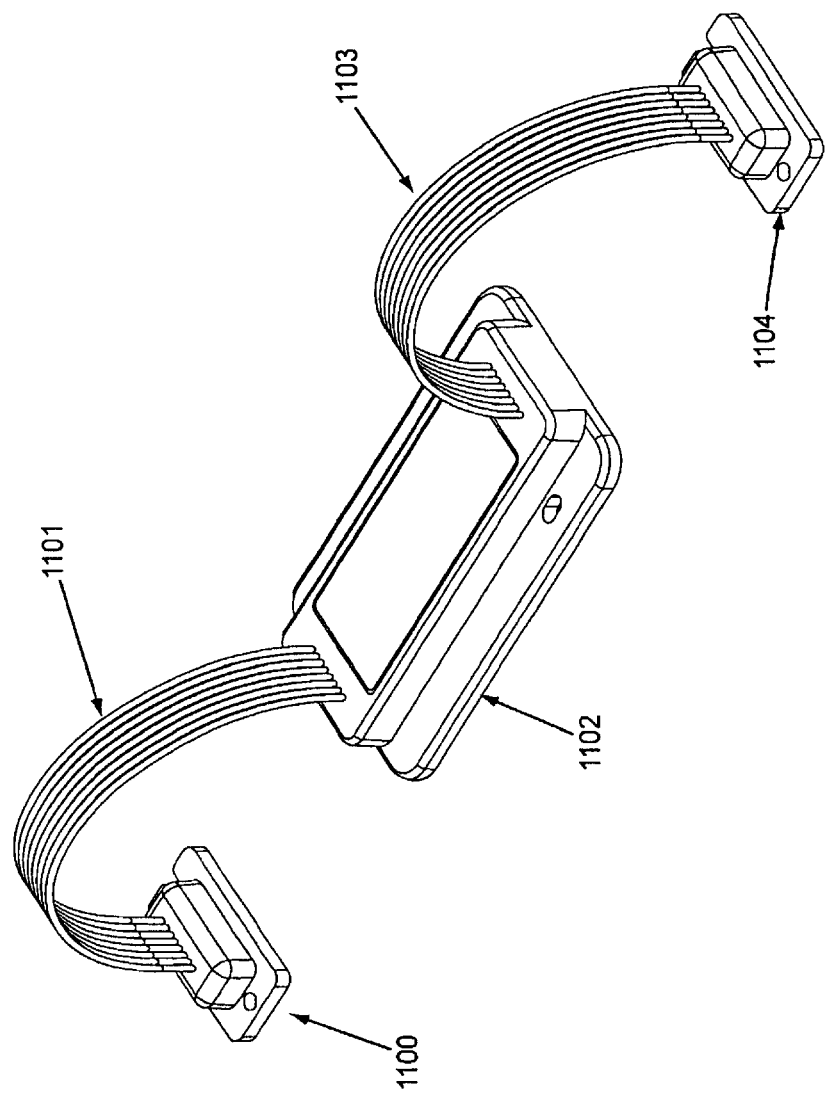
FIG. 11A displays an exemplary reagent manifold of the invention.
Figure 11B:
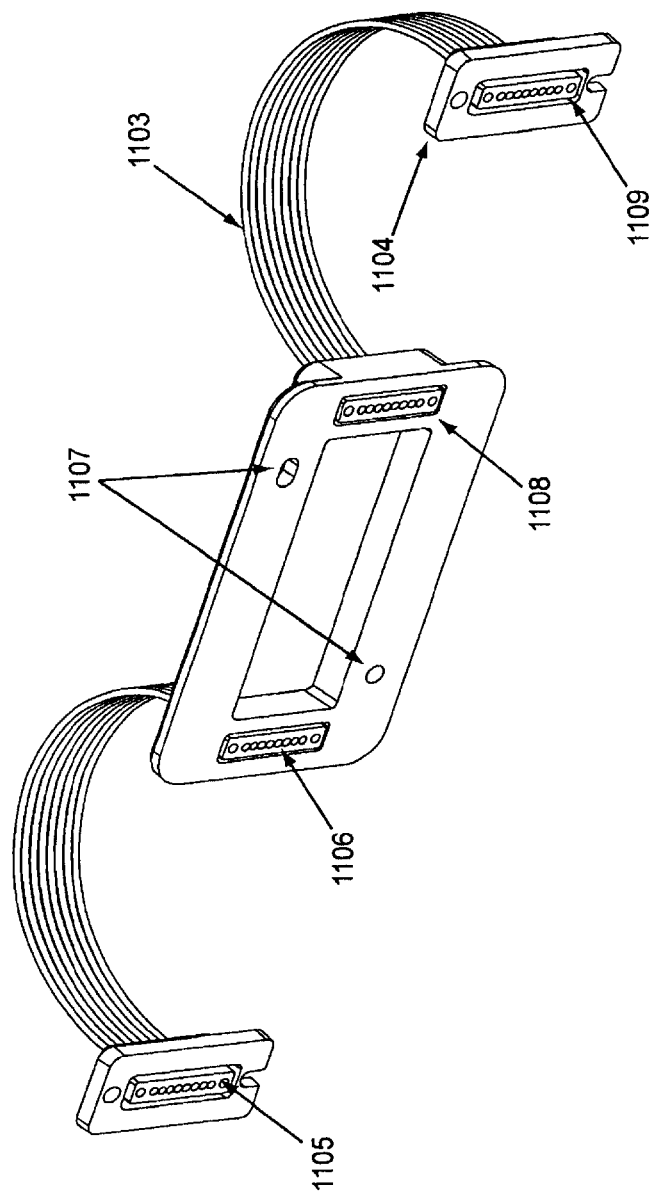
FIG. 11B is a bottom perspective view of the reagent manifold of FIG. 11A.

FIG. 11 shows a "common solution" or "reagent" manifold (top view in 11A and bottom view in 11B). In FIG. 11A, proximal manifold plug 1100 is connected to proximal tubes 1101, which in turn fluidly connect with manifold main body 1102. Distal tubes 1103 leave from the main body of the manifold and fluidly connect with distal manifold plug 1104. As will be appreciated, some manifold embodiments are symmetric, i.e., the proximal and distal ends have the same structure. However, such embodiments still have proximal and distal ends based on their placement in relation to the flow cell and other components of the device and are addressed as such for ease of description. As explained further below, reagent manifolds are used to flow common solutions or reagents through all of the channels of the flow cell. This is as opposed to sample manifolds that are used to flow specific nucleic acid samples into specific channels of the flow cell. FIG. 11B shows the under side of the reagent manifold with proximal tube ends 1105 allowing fluidic access into the proximal tubes, and openings 1106 allowing fluidic exit from the proximal tubes. The proximal tube ends are fluidly connected to the reagent reservoirs via a branched array of subports from a common port. See FIGS. 15 and 26 for examples. FIG. 11B also shows distal tube openings 1108 that allow fluidic access from the channels of the flow cell into distal tubes 1103. Distal tube ends 1109 are shown in the distal manifold plug 1104. Such ends are fluidly connected to the waste reservoir. Positioning grooves 1107 can also be seen. Such grooves can optionally match up with pins or posts on the flow cell placement area. See FIG. 8B.

FIG. 12 shows an exemplary reagent manifold configured in a device of the invention. The reagent manifold in FIG. 12 is similar to that shown in FIG. 11. Thus, proximal tubes 1200 allow fluid connection from the reagent reservoirs (via proximal manifold plug 1203) to main body 1201 of the manifold and the flow cell underneath it. Flow from the flow cell traverses through distal tubes 1202 through distal manifold plug 1205 and thence to the waste reservoir.

Figure 13:
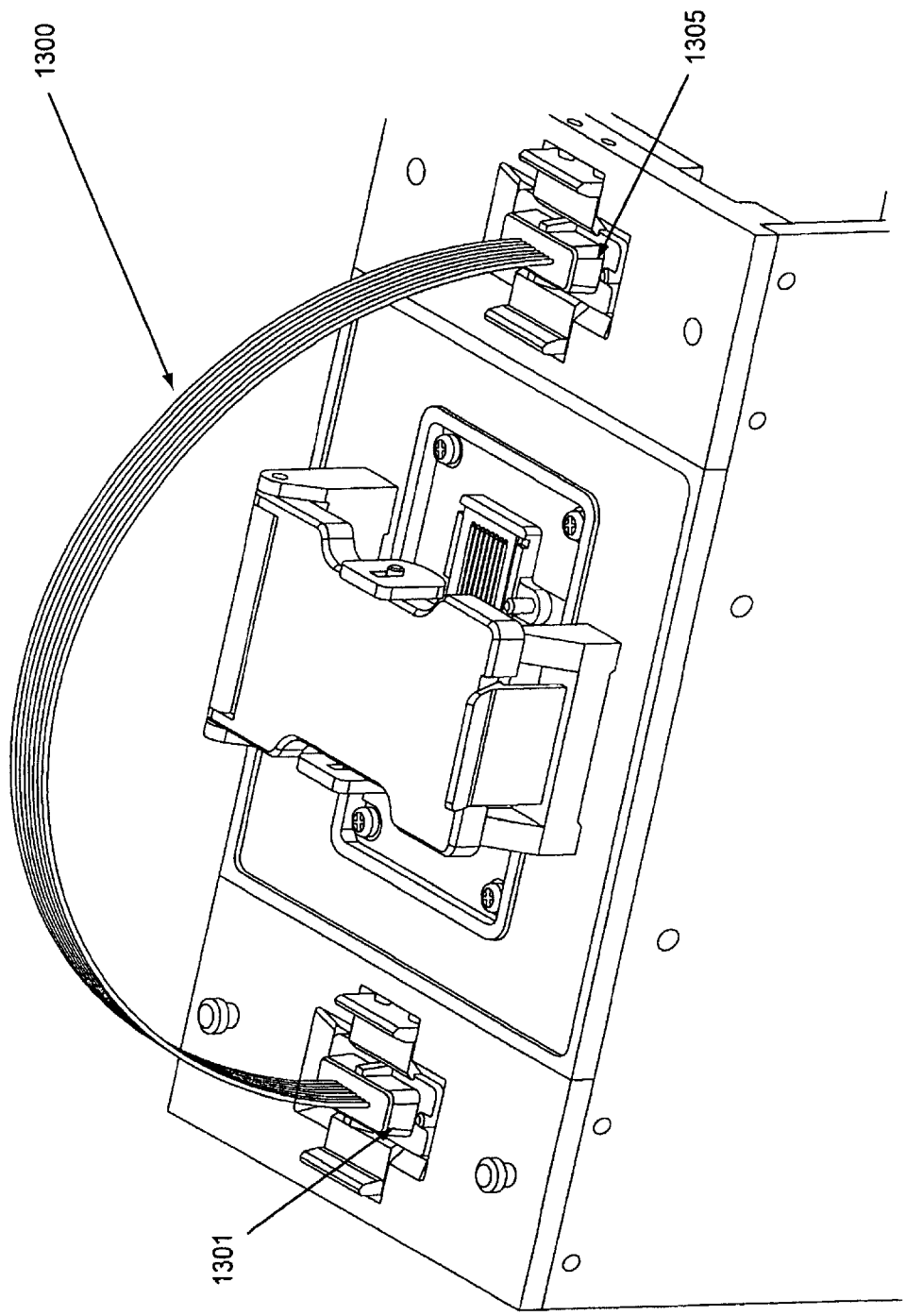
FIG. 13 displays an exemplary wash connection and its placement in relation to the manifold attachment areas.

In order to flush the various fluidic connections and conduits of the invention (e.g., between uses of the device), a wash connection such as that shown in FIG. 13 is optionally used. As can be seen from the figure, the wash connection configuration does not typically comprise a main manifold body component. Instead, flow of reagents (or optionally of water, or other solvents, to clean the fluidic connections of the device) traverses through wash tubes 1300. Similarly to the reagent manifolds described above, the wash connection also comprises plug ends 1301 (proximal) and 1305 (distal) that allow fluidic connection with the other fluidic components of the device. Thus, if a fluid flow is pulled or pushed towards the waste reservoir, a wash solution or the like is correspondingly drawn/pushed through the other fluidic paths of the device since they are fluidly connected.

Figure 14:
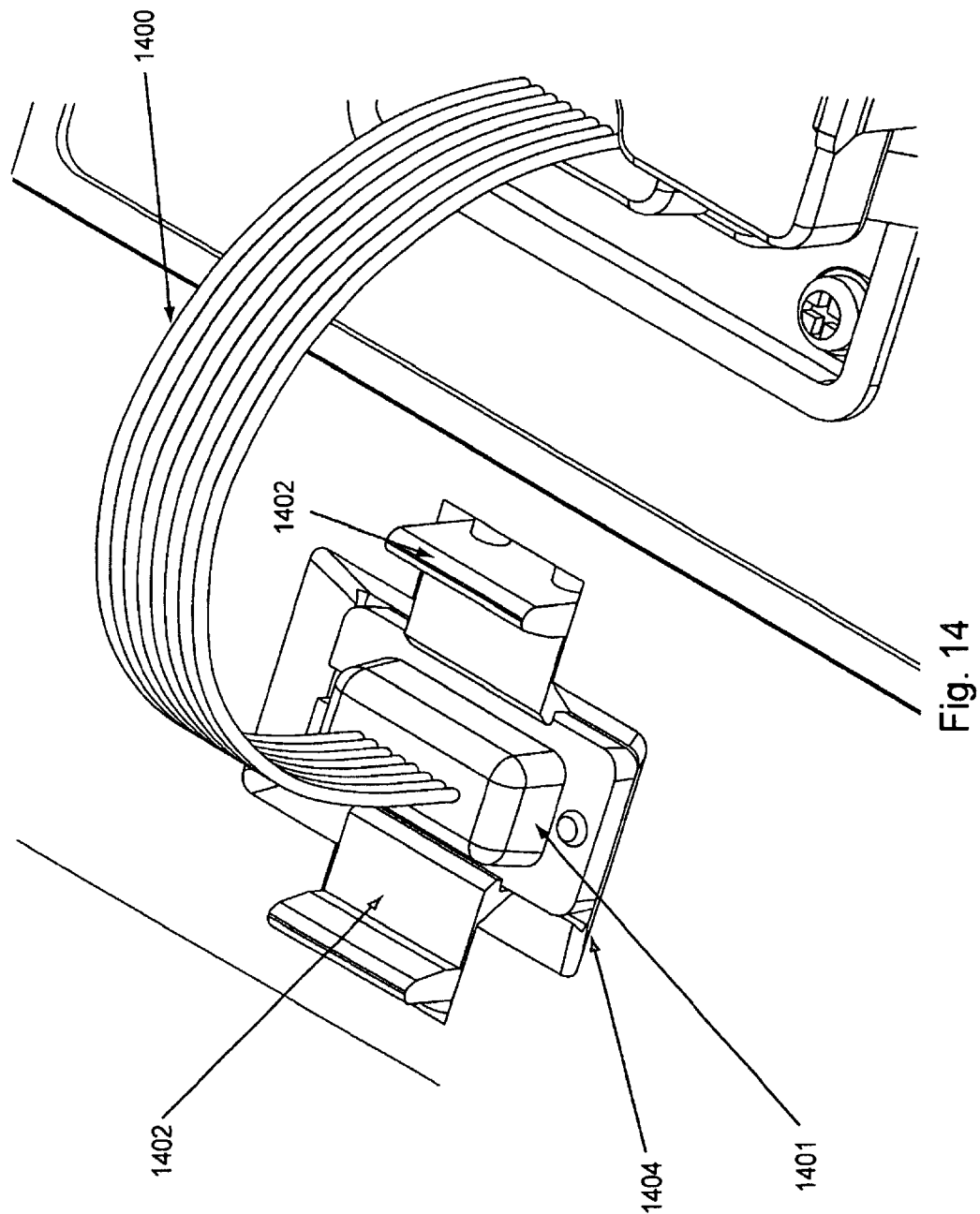
FIG. 14 displays an exemplary quick connection of a manifold plug and a manifold attachment area.

FIG. 14 illustrates securing of an exemplary connection between manifold plug 1401 and manifold attachment area 1404. Side clamps 1402 grasp the manifold plug and secure it to the manifold attachment area, thus, sealing the components together and creating fluidic connections that allow reagents, etc. to flow from the reagent storage areas into the manifold and flow cell. FIG. 14 presents the connection of proximal tubes and proximal manifold plug, but it will be appreciated that similar side clamps are also optionally used to secure distal tube connections as well. It will also be appreciated that the clamp can comprise different configurations in different embodiments. See, e.g., FIGS. 25A-G which show an alternative clamp embodiment used with various manifolds.

Figure 25A:
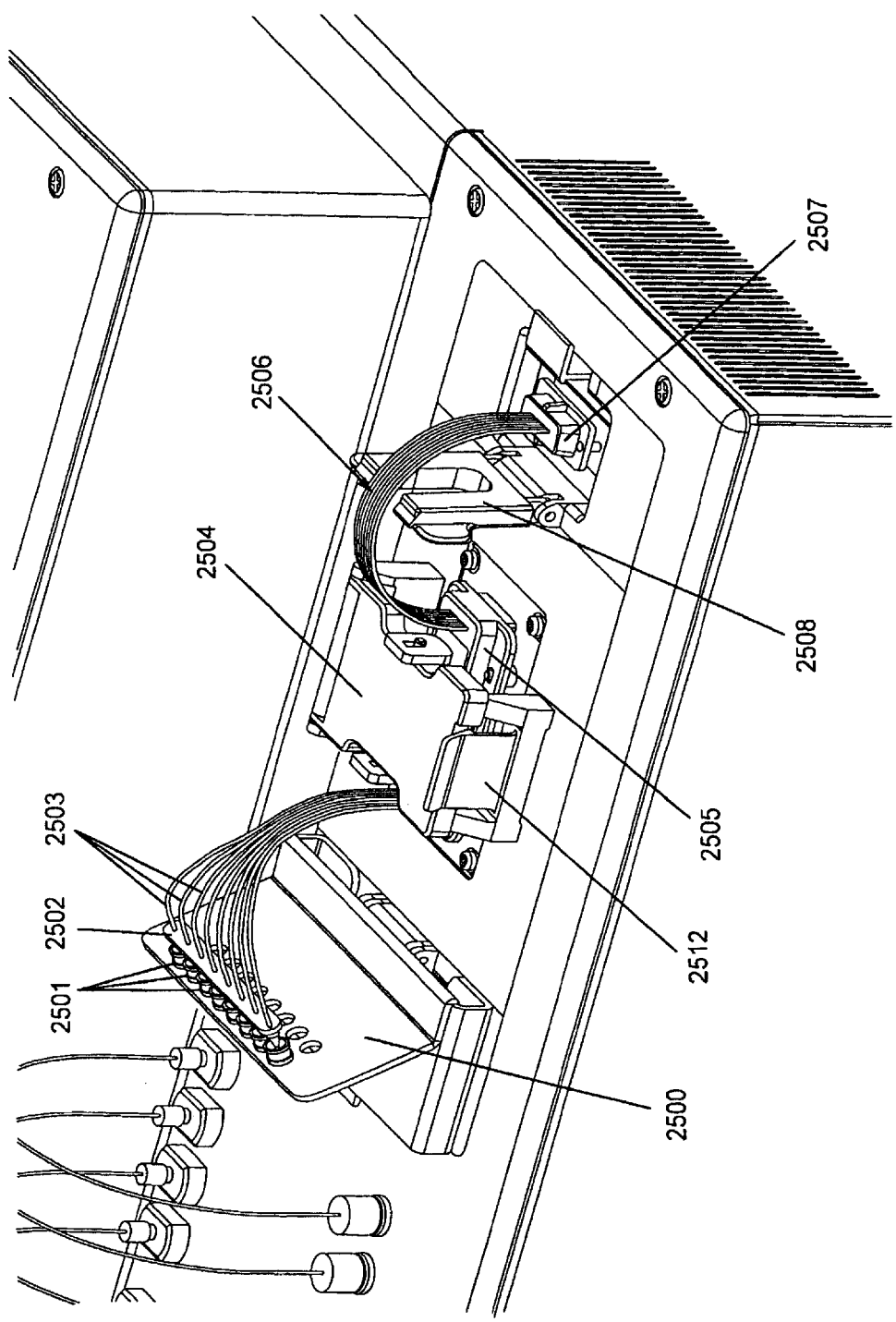
FIG. 25A illustrates an exemplary manifold and a side clamp in an open position.
Figure 25B:
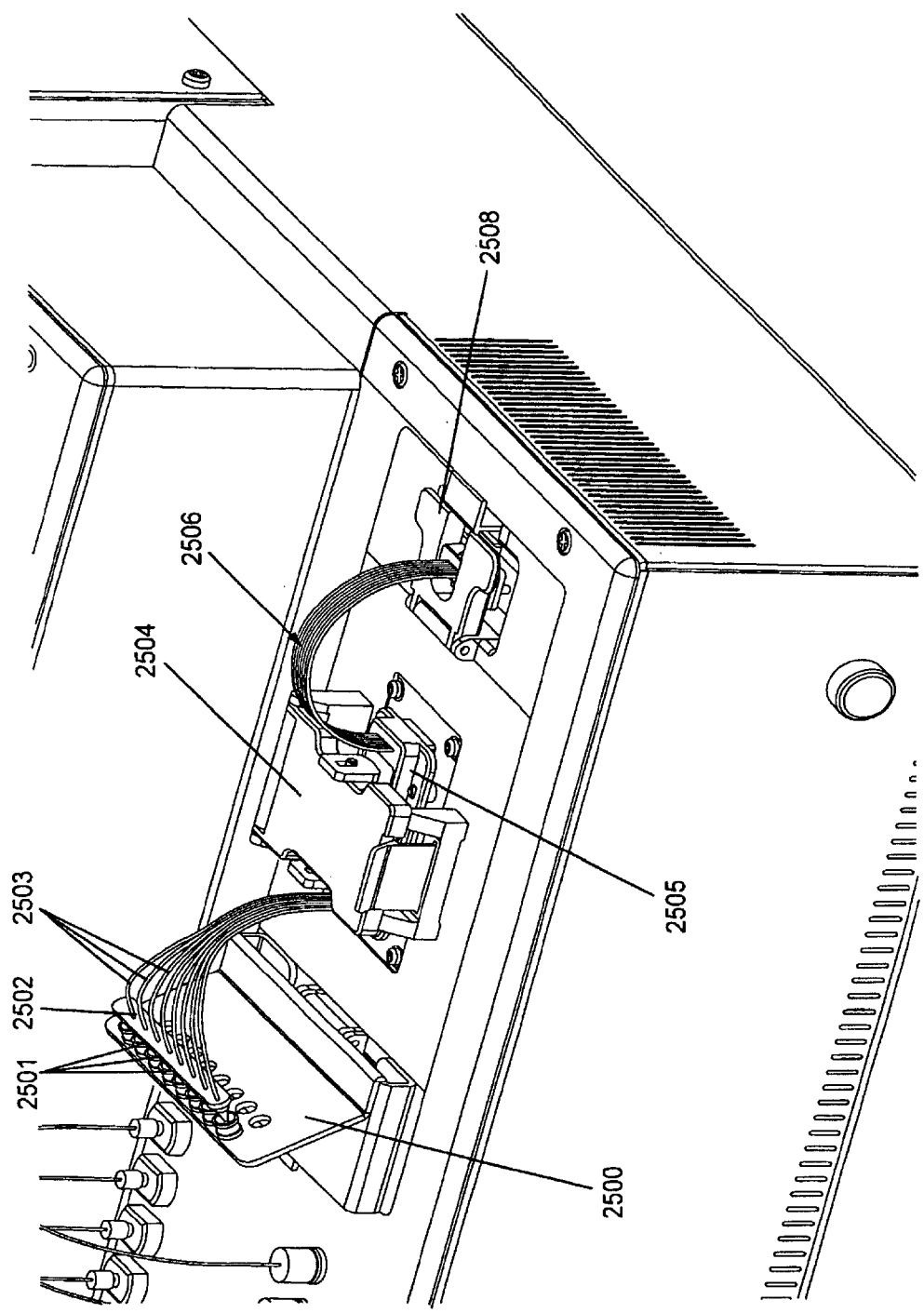
FIG. 25B illustrates the side clamp in the closed position.
Figure 25C:
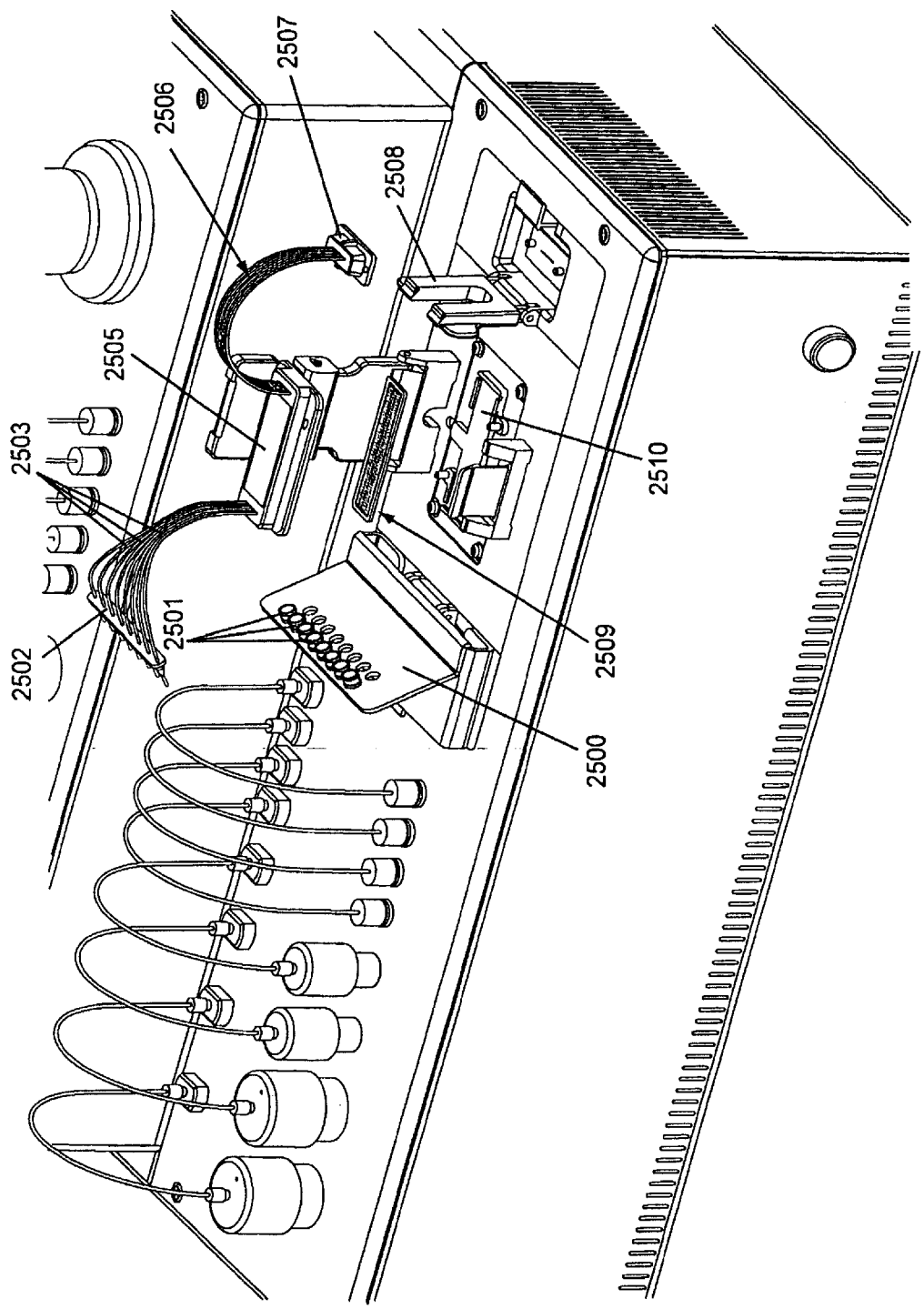
FIG. 25C illustrates the exemplary manifold separate from a flow cell holder.
Figure 25E:
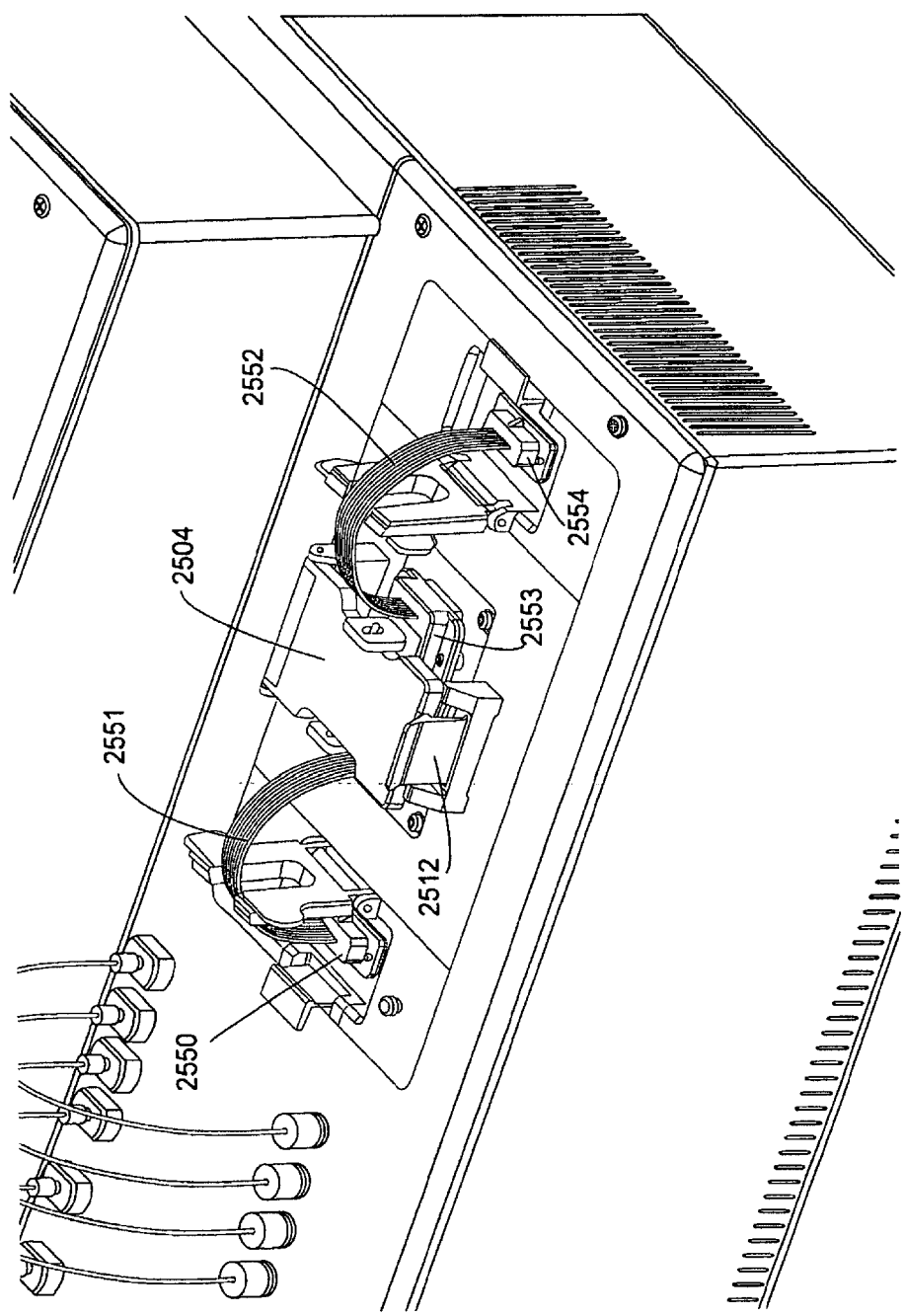
FIG. 25E illustrates an exemplary manifold, a flow cell holder in a closed position, and two side clamps in open positions.
Figure 25G:
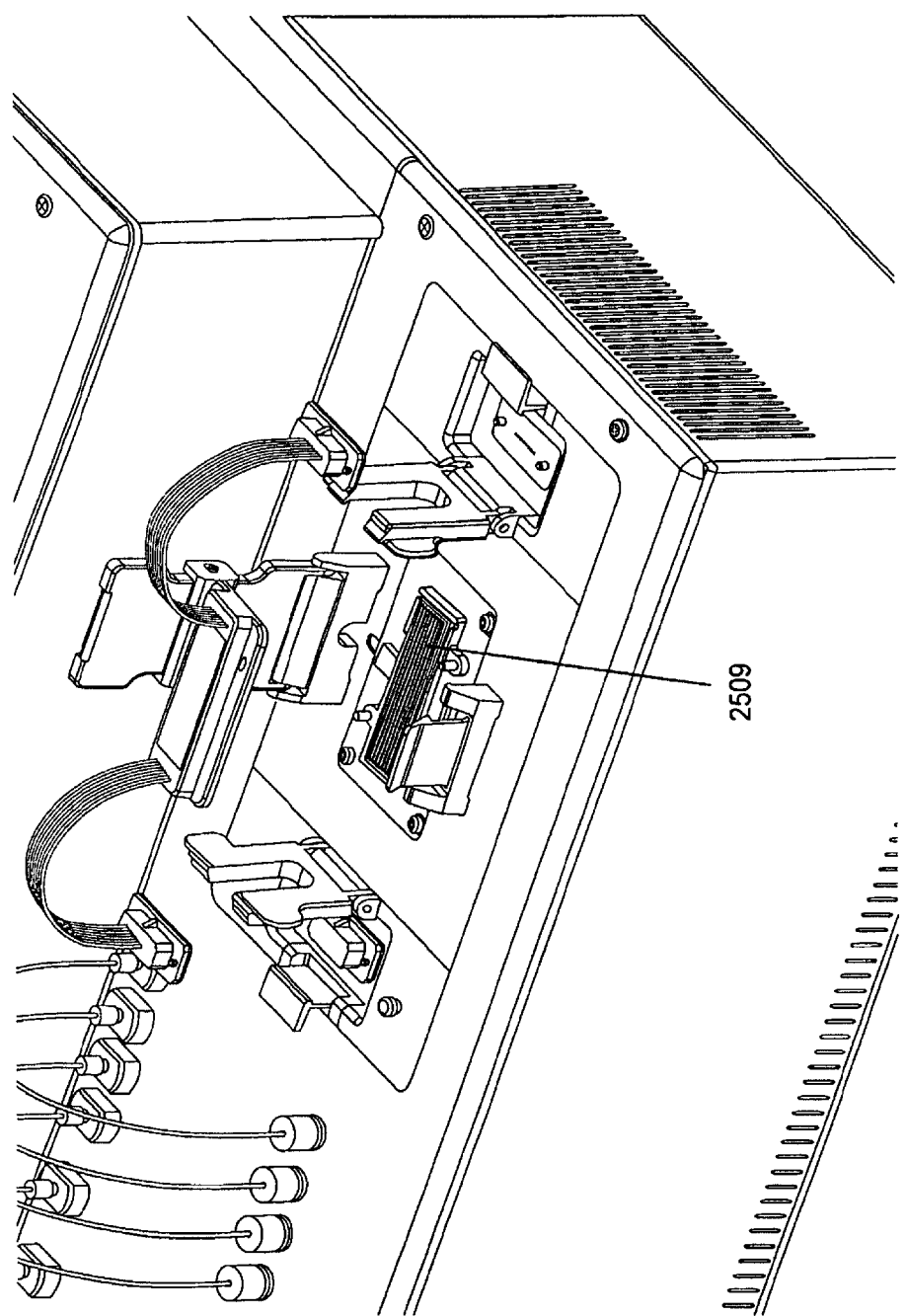
FIG. 25G illustrates the manifold and two side clamps in open positions with respect to the flow cell holder in an open position.

In FIGS. 25A-D is shown placement and orientation of a sample manifold having main body 2505, proximal tubes 2503, distal tubes 2506, sealing strip 2502, and distal manifold plug 2507. Sample vials 2501 hold DNA templates to amplify. The sample vials are held in sample holder 2500. Flow cell holder 2504 (clasped by clamp handle 2512) is shown holding the manifold body and flow cell 2509 (not visible in 25A, B, or D) down to flow cell placement area 2510 in FIGS. 25A and 25B, while it is shown "open" in FIG. 25D (allowing compression bar 2511 to be visible) and with the various components separated in FIG. 25C. Side clamp 2508 is shown securing the distal manifold plug in FIG. 25B and "open" in FIGS. 25A and 25C-D. Corresponding placement of an exemplary reagent manifold on the same device with the same flow cell is shown in FIGS. 25E-G. In FIGS. 25E-G is shown placement and orientation of manifold main body 2553, proximal tubes 2551, distal tubes 2552, proximal manifold plug 2550, and distal manifold plug 2554. Side clamps 2508 (both proximal and distal) are shown "open" in FIG. 25E and "closed" in FIG. 2SF.

Figure 15A:
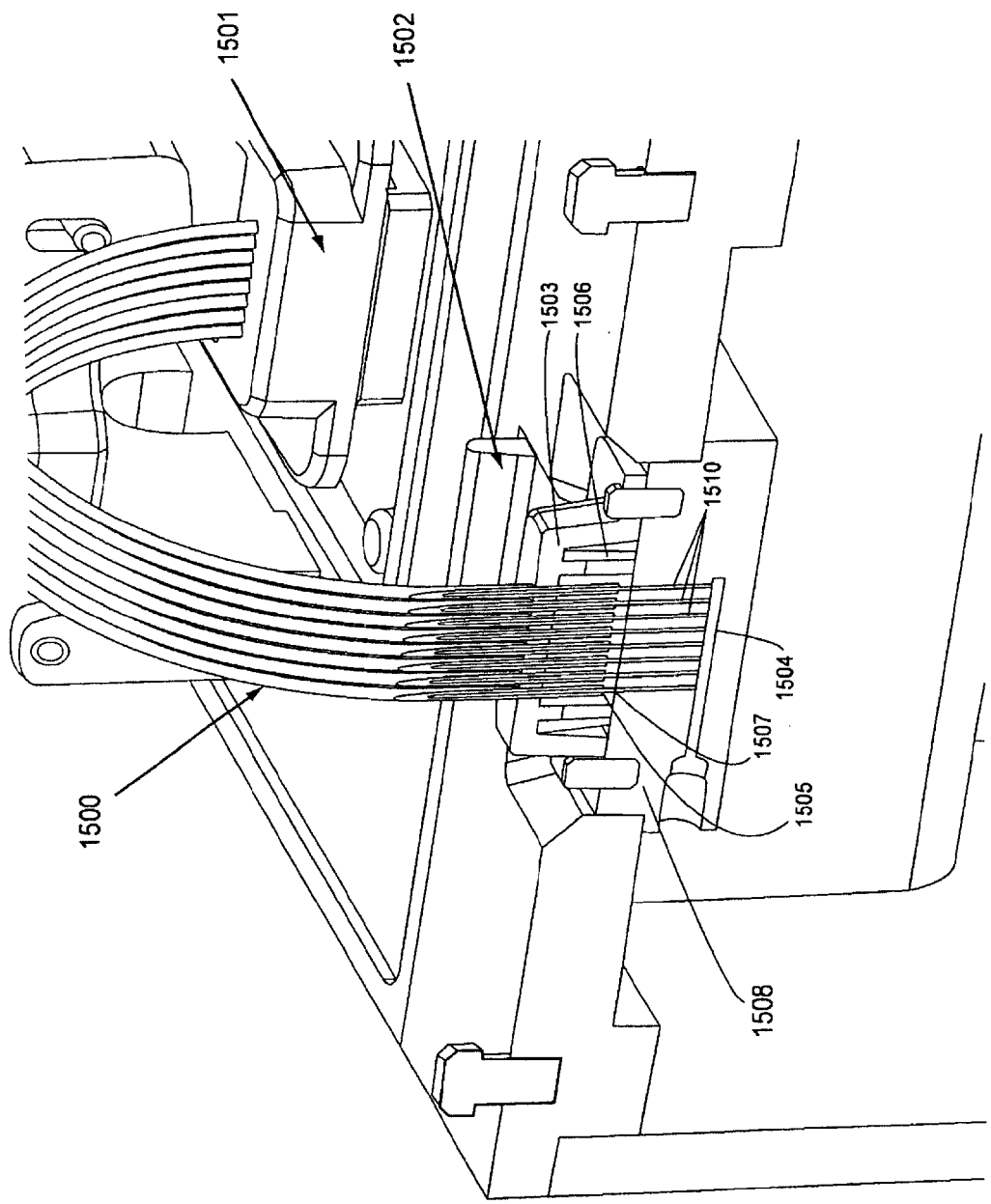
FIG. 15A displays a partial cut away view of the interaction of an exemplary manifold plug and a manifold attachment area.
Figure 15B:
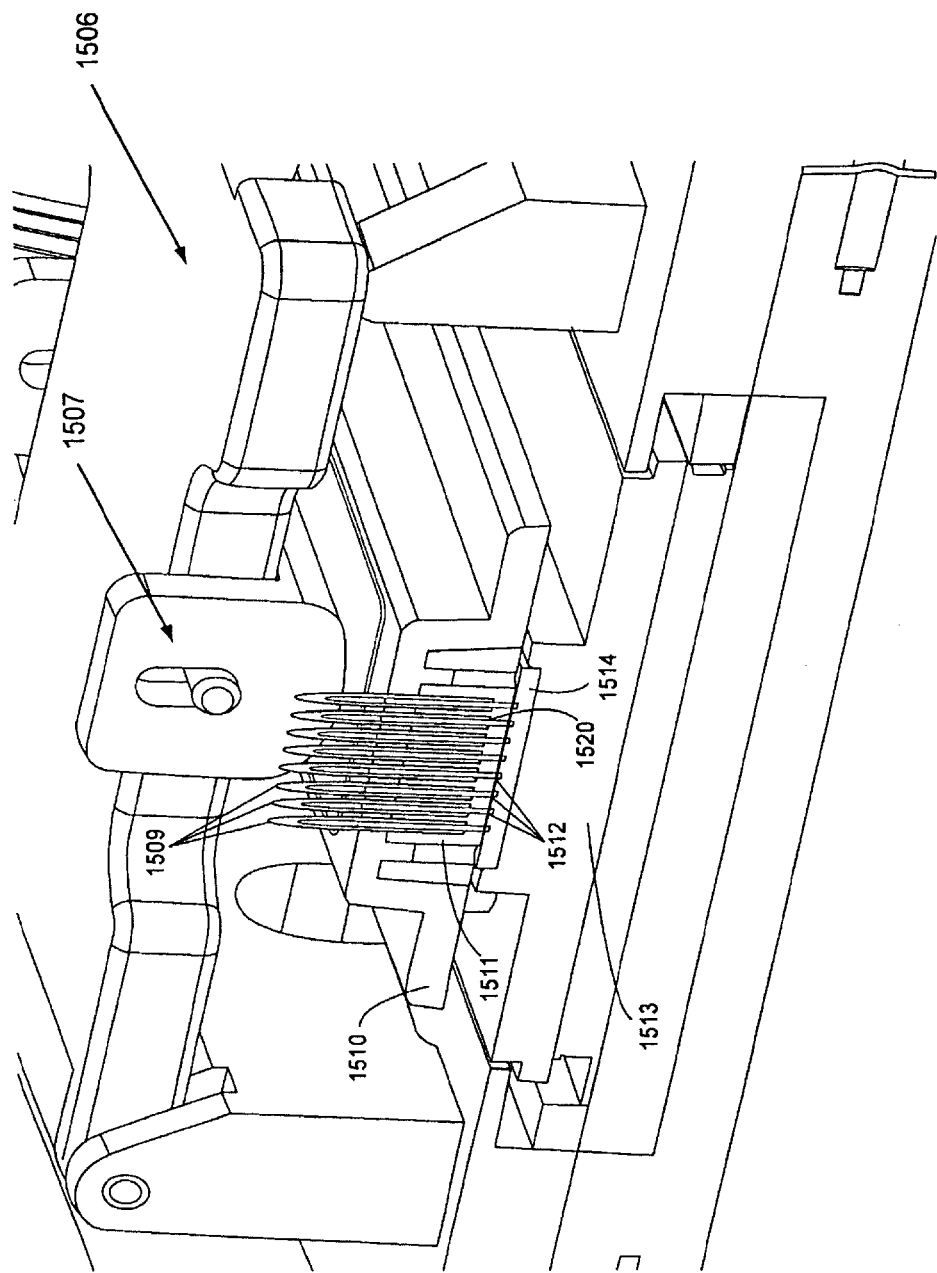
FIG. 15B displays a partial cut away view of the connection of proximal tubes to a manifold body and a flow cell.
Figure 26:
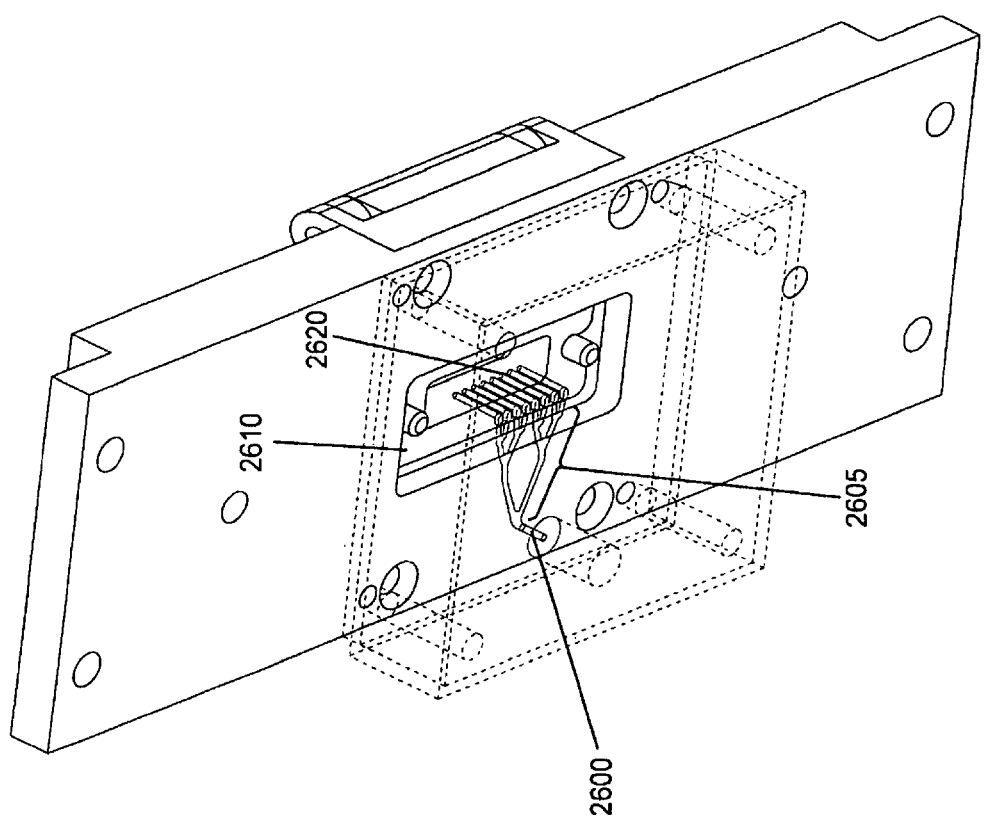
FIG. 26 shows an exemplary embodiment of a brachiated tube/port arrangement of the invention.

FIGS. 15A and 15B show close-up cut away views of the connection of a proximal manifold plug and its corresponding manifold attachment area (FIG. 15A) and connection of proximal tubes to the main body of a manifold and a flow cell (FIG. 15B). In FIG. 15A, proximal tubes 1500 are connected with proximal manifold plug 1503 (held secure by side clamp 1502). The proximal tubes meet and comprise blunt end junctions 1505 with inner layer 1506 of the manifold plug. The inner layer of the manifold plug in turn comprises blunt end junctions 1507 with the surface of proximal manifold attachment area 1508. Reagents from the various storage reservoirs traverse through common port 1504. The common port branches into subports 1510, each of which matches up with a different proximal tube. Cf. FIG. 26. The individual proximal tubes comprise a fluidic connection through such junctions to the reagent storage areas.

FIG. 15B shows a close up cut away view of the connection of proximal tubes and the main body of a manifold as well as the fluidic connection between the manifold body with an underlying flow cell as the manifold and flow cell are secured within a flow cell holder. As can be seen from the figure, proximal tubes 1509 (shown cut away) enter manifold main body outer layer 1510, and have blunt end junctions 1520 with manifold inner layer 1511. Openings in the inner manifold layer match up with channels in the underlying flow cell (flow cell 1514) at connections 1512. As shown in FIG. 15B, the manifold body and flow cell are held securely in place by flow cell holder 1506. Compression bar 1507, as explained above, exerts downward pressure on the manifold body, thus pressing the manifold and flow cell together creating more secure fluidic connections. The compression bar also presses the flow cell against flow cell placement area 1513 which, as explained below, helps create and maintain proper temperature conditions in the flow cell.

In some embodiments, the fluid flow from a common reagent tube into a manifold can go through a brachiated structure rather than the linear structure shown in FIG. 15A. For example, FIG. 26 shows a common reagent port (tube) entering a proximal manifold, having a multiple bifurcating (or tree) pattern. Thus, the reagents are more evenly distributed to each tube in the manifold, and thus are more evenly distributed to each channel in a flow cell. With extremely small volumes of fluid, the linear distribution pattern as shown in FIG. 15A can occasionally create situations wherein the final manifold tubes furthest from the main reagent tube will receive a smaller amount of reagent. Embodiments such as that shown in FIG. 26, ensure even with extremely small aliquots of reagents, that equal amounts are delivered to each manifold tube (and thus equal amounts are delivered to each flow cell channel). In FIG. 26, common reagent port (tube) 2600, shown from the underside, brachiates with multiple bifurcations 2605 into subports 2620. The subports enter into manifold plug 2610, with similar connections/junctions as explained for those in FIG. 15.

Temperature Control

Figure 16:
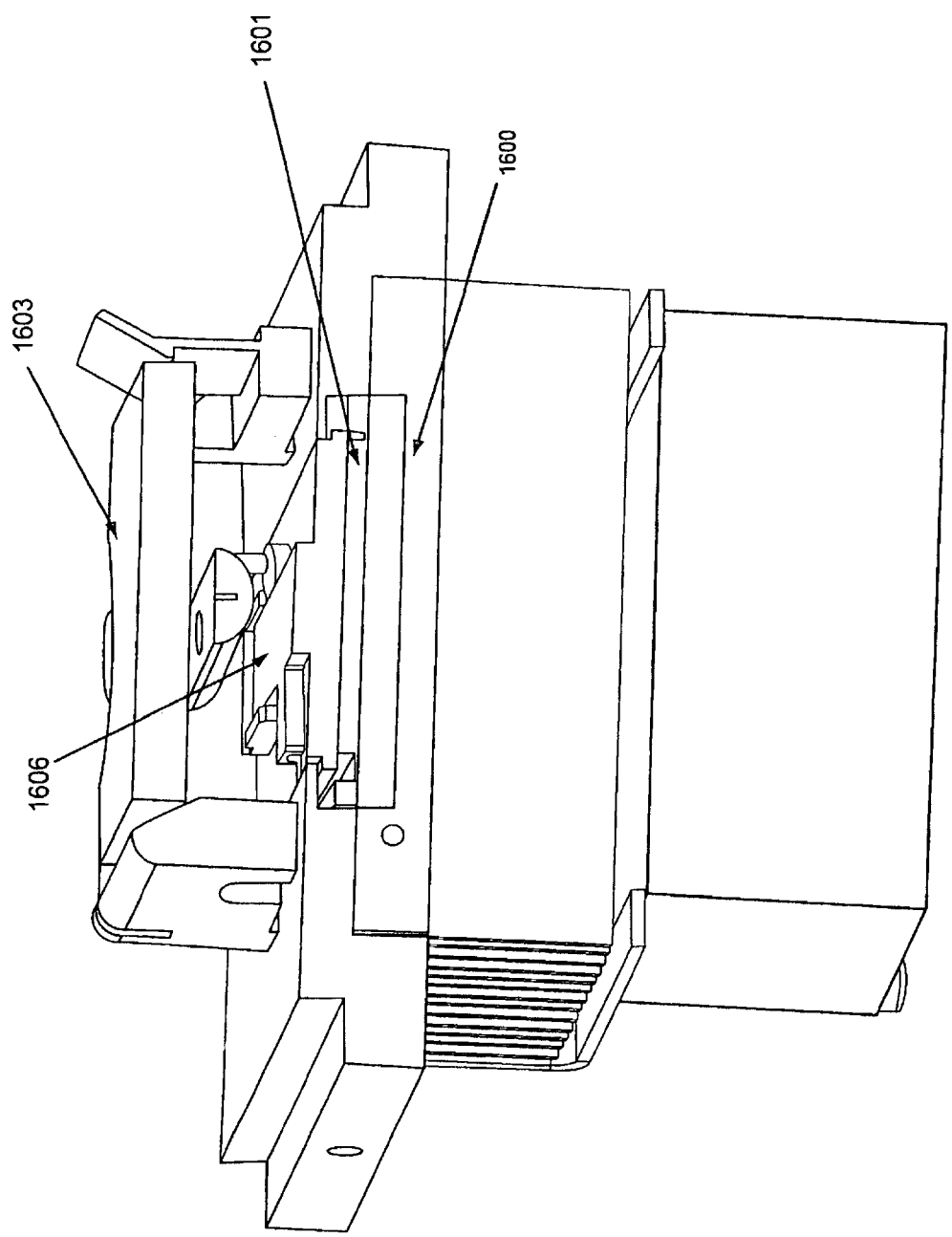
FIG. 16 displays an exemplary temperature regulating component of the invention in configuration with a flow cell holder.
Figure 17:
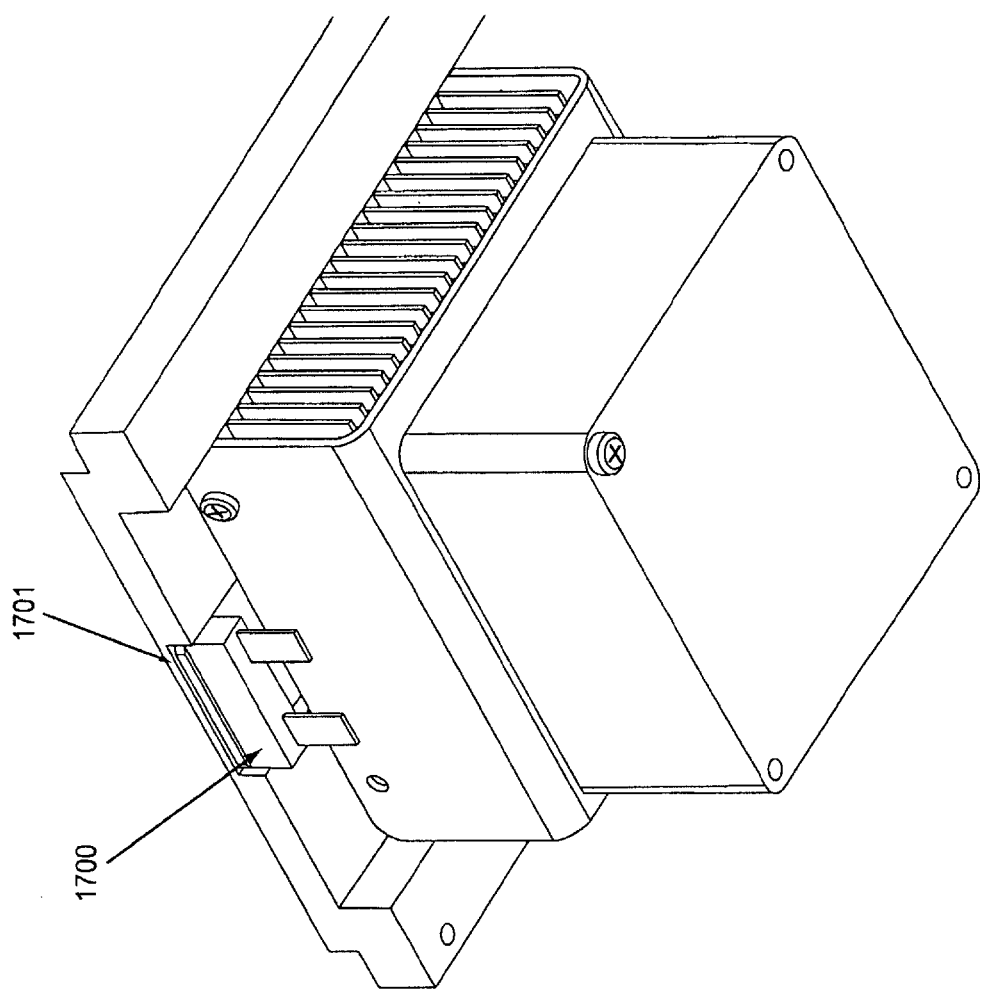
FIG. 17 displays a bottom view of an exemplary temperature regulating component of the invention.

The systems herein also comprise one or more temperature control components having heating capability, e.g., Peltier or other thermoelectric control heating devices, etc. Optionally, the various components herein (e.g., the flow cell and its contents) can be temperature regulated by a resistive heating element and/or through convection to create proper temperature conditions (e.g., isothermal reaction conditions). Such temperature regulation component can control the temperature of the flow cell (and the fluids within it) during the various reactions required in nucleic acid amplification to ensure isothermal reaction conditions. An exemplary temperature control system is shown in FIGS. 16 and 17. In various embodiments, the temperature control elements regulate the temperature of the flow cell and its contents to be stable (i.e., isothermal/substantially isothermal) at a point from about 20° C. to about 70° C. In particular embodiments, the temperature control component that creates isothermal conditions in the flow cell does not comprise an active cooling component. Instead, such temperature component relies on ambient cooling when needed (e.g., to maintain isothermal conditions).

Those of skill in the art will be familiar with Pettier and similar devices used for temperature control (which can optionally be used in the systems and devices herein). Again, it will be appreciated that while certain temperature regulation components are recited herein, such should not be construed as necessarily limiting. Thus, in certain embodiments components other than Peltier devices are optionally comprised within the present invention. In typical embodiments, notwithstanding the type of device, the temperature regulation component is optionally held (e.g., in terms of the set temperature level) by the computer component. See below.

In some embodiments, the temperature regulation components can also regulate the temperature of other components in addition to, or alternate to, the flow cell. For example, a temperature control component can regulate the temperature of at least part of the reagent storage areas, various fluidic conduits, the body or chassis of the device, etc. Additionally, in some embodiments, the temperature regulation component optionally can also be used to cool the sample chip or flow cell after the isothermal amplification process has been completed.

FIG. 16 shows exemplary placement of a temperature regulation component beneath the location where the flow cell and manifold are placed. The temperature control component in such location can ensure that the reaction conditions in the flow cell remain at the correct temperature at the appropriate times and do not substantially fluctuate. In FIG. 16, temperature regulation component 1600 (e.g., a thermoelectric controller such as an XLT 2389 Marlow TEC) is shown located beneath flow cell holder 1603 and flow cell placement area 1606. In various embodiments, the temperature control component can operate at any desired amplification temperature. Also shown in FIG. 16 is metal insert 1601 which can help improve thermal uniformity. Such metal insert can be copper, aluminum, or any other appropriate metal with the desired thermal characteristics.

FIG. 17 shows an alternate view of the configuration in FIG. 16. In FIG. 17, thermal fuse 1700 is shown mounted on a heated plate beneath flow cell placement area 1701.

Reagent and Waste Reservoirs

Proper storage and access of the various reagents herein is important in efficient amplification. As will be well known to those of skill in the art, in nucleic acid amplification some reagents typically can be stored and/or utilized at room temperature while other reagents (e.g., enzymes such as non thermophilic DNA polymerases, or nucleotide triphosphates) have a longer storage life if kept below room temperature (e.g., 4° C., etc.).

Figure 18A:
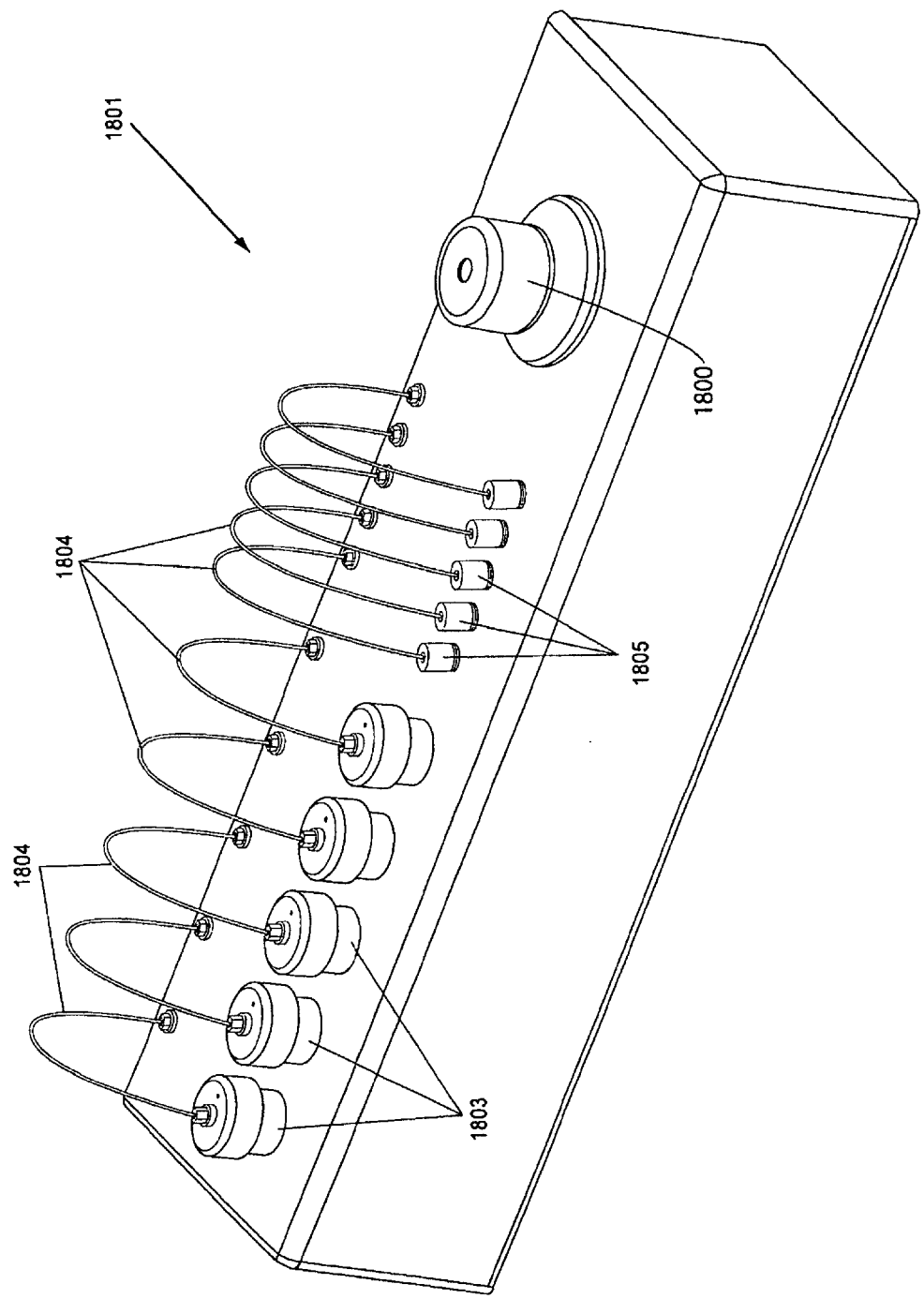
FIG. 18A displays exemplary ambient temperature reagent and waste reservoirs of the invention.
Figure 18B:
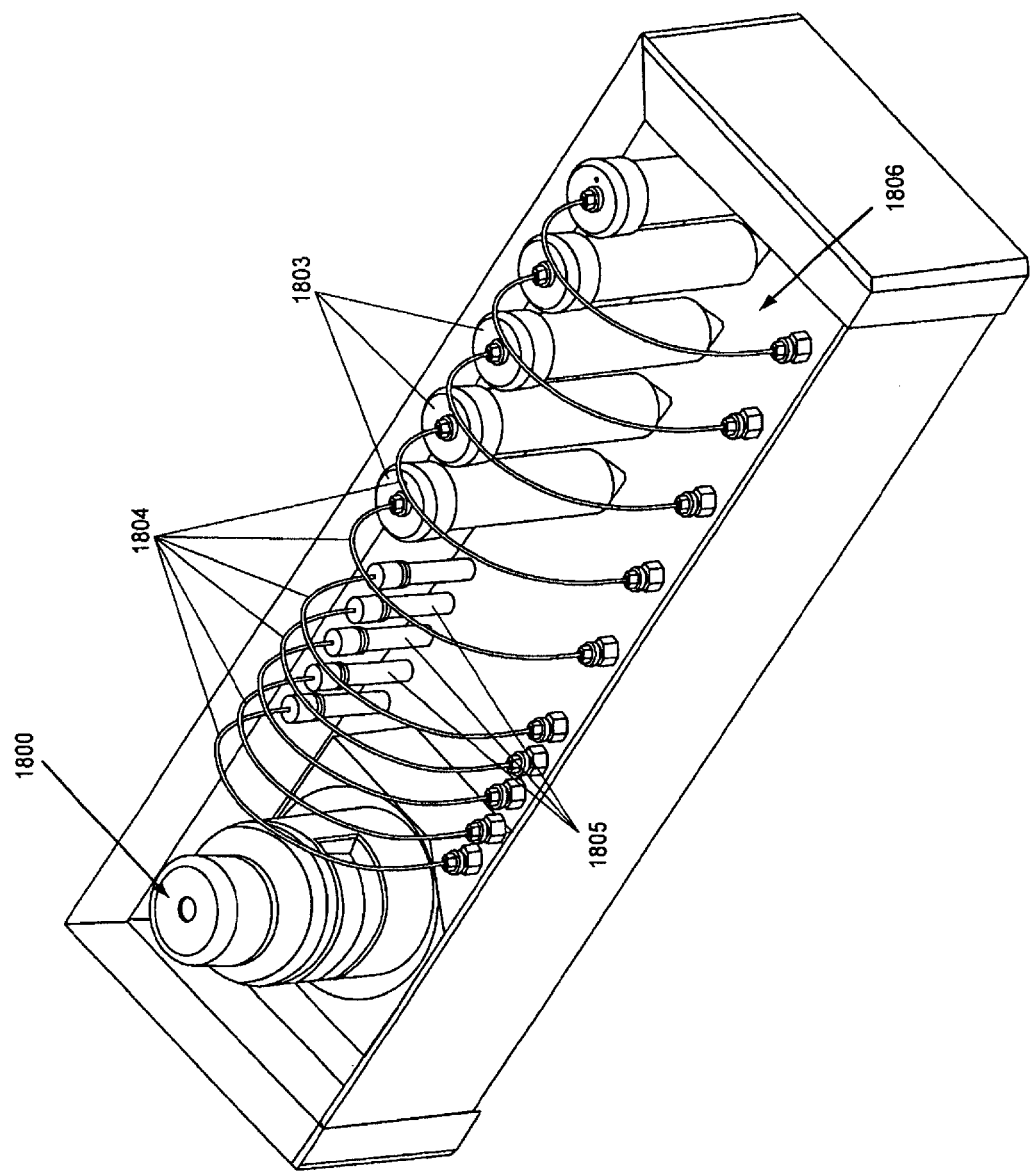
FIG. 18B is another view of the ambient temperature reagent and waste reservoirs of the invention.

FIGS. 18A and 18B show two views of ambient-temperature reagent and waste storage area 1801. As can be seen in FIG. 18A, reagent storage reservoirs 1803 and 1805 (which comprise different volumes in the shown embodiment) are placed within assembly area 1801. Cf. FIG. 1. The same reagent storage reservoirs can be seen in FIG. 18B which shows the interior of the assembly area and spill containment carrier 1806. In FIGS. 18A and B, the reagent storage reservoirs are fluidly connected to the other fluidic components of the invention through reagent tubes 1804. The reagent tubes can be constructed from such material as, e.g., polypropylene or polyethylene or the like. In typical embodiments, the reagent tubes comprise a sipping tube (e.g., comprised of PEEK) in order to draw the reagents from the reservoirs. In particular embodiments the reagent tubes pass through, and are attached to, the caps of the reagent reservoirs. Also shown in FIGS. 18A and B is waste reservoir 1800 (tube/fluidic connections to the waste reservoir are not shown in the figure). It will be appreciated that the reservoirs/vials/conicals or the like, in which the reagents are stored are optionally supplied by the end user. Also, in some embodiments, the reagents are optionally stored in containers outside of the main body or chassis of the device. Such containers are fluidly connected, however, with the flow cell, manifold, etc.

Figure 19:
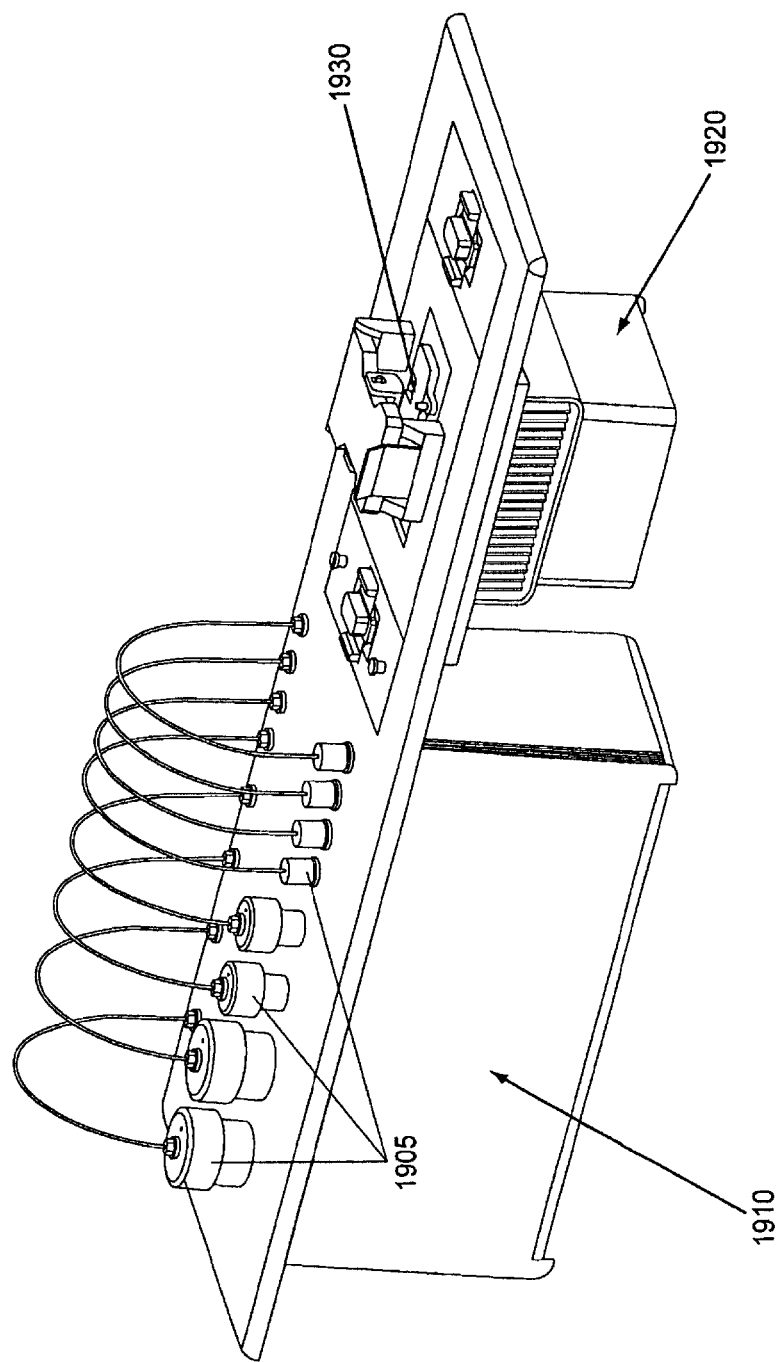
FIG. 19 displays an exemplary temperature controlled reagent storage reservoirs in configuration with a flow cell holder area.
Figure 20A:
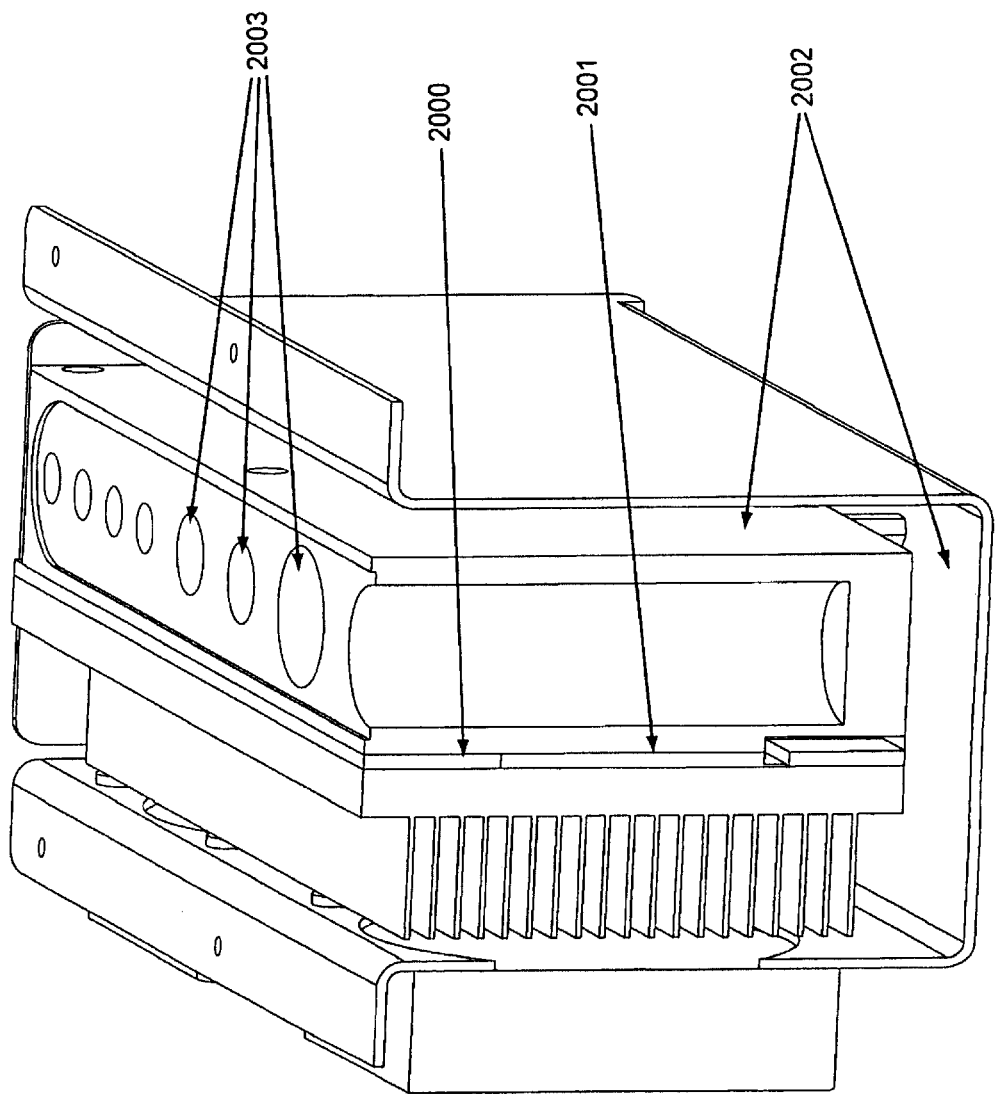
FIG. 20A displays an optional temperature controlled reagent storage reservoir area.
Figure 20B:
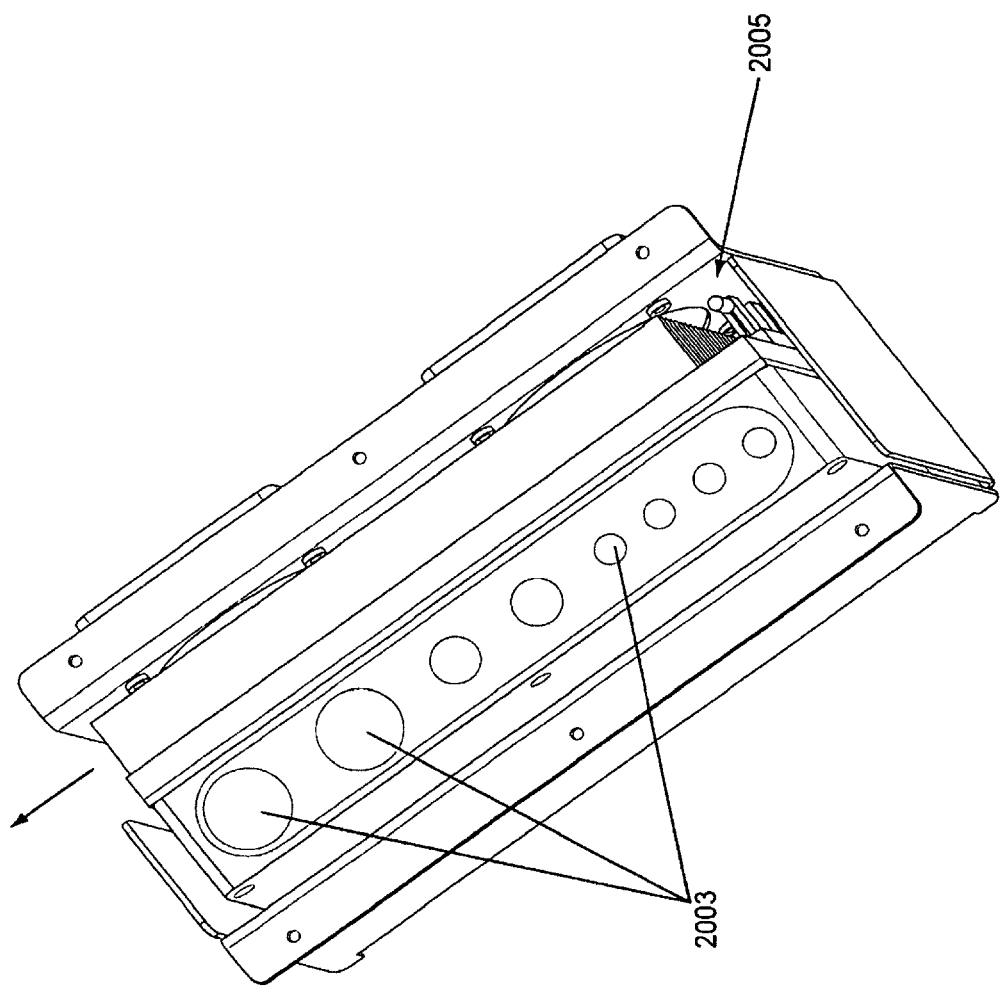
FIG. 20B shows a top view of the optional temperature controlled reagent storage reservoir area.

FIG. 19 shows an isolated reagent storage assembly that is temperature regulated (as opposed to the ambient temperature reagent area of FIG. 18) as well as the flow cell placement area, a temperature regulation component, etc. Cf. FIGS. 1 and 18. As described above, in typical nucleic acid amplification reactions (including the ones performed through use of the current invention), particular reagents can optionally be stored and/or used at below room temperature. Thus, FIG. 19 shows reagent storage areas 1905 which are optionally temperature regulated by temperature regulation component 1910 (e.g., a Peltier or other TEC). Also seen in FIG. 19, temperature regulation component 1920 (e.g., a Peltier or other TEC) regulates temperature in flow cell holding area 1930. FIG. 20A shows an exemplary arrangement configured to regulate the temperature of reagent reservoirs. In such embodiment the reagent reservoirs are placed within holding areas 2003 that are cooled with temperature regulator 2001 (e.g., a Marlow TEC or other similar thermoelectric controller or Peltier component) present in holder space 2000. The chilled reagent holding area does not typically directly abut the outside walls of the chassis, but rather is surrounded by insulation (e.g., foam, etc.) that is present in space 2002. FIG. 20B shows a top view of the set up of FIG. 20A highlighting thermal fuse 2005 on the heatsink for reagent storage and showing direction of airflow.

Pumps and Valves

In the various embodiments herein, the reagents, buffers, etc. used in the nucleic acid amplification are regulated and dispensed via a fluid flow subsystem or components. In general, the fluid flow components transport the appropriate reagents (e.g., enzymes, buffers, nucleotides, etc.) at the appropriate rate and optionally at the appropriate temperature, from reagent storage reservoirs (e.g., bottles, or other storage containers) into and through the manifold to the flow cell and from the flow cell to a waste receiving area.

The fluid flow aspect is typically computer controlled. The temperature of various reagents, buffers or the like within the fluid flow components is optionally computer controlled as well. For example, as described above, certain reservoirs are optionally held at cooled temperatures such as 4° C.+/−1° C. (e.g., for enzyme containing solutions), while other reagents are optionally held at ambient temperatures (e.g., buffers to be flowed through the flow cell wherein the particular amplification step is not required to be cooled to below-ambient temperature).

The fluid flow itself is optionally driven by any of a number of pump types, (e.g., positive/negative displacement, vacuum, peristaltic, etc.) such as an Encynova® 2-1 Pump or a Kloehn® V6 Model 8 Syringe Pump. Again, it will be appreciated that specific recitation of particular pumps, etc. herein should not be taken as necessarily limiting and that various embodiments can comprise different pumps and/or pump types than those listed herein. In typical embodiments, the pump(s) and valves herein are controlled by computer instructions (e.g., via a RS232 adapter, see below).

The fluid flow subsystem of the invention also can control the flow rate of the reagents involved. The flow rate is optionally adjustable for each flow path (e.g., some flow paths can proceed at higher flow rates than others; different channels can receive different reagent flows or different timings of reagent flows, etc.). The flow rate can be set in conjunction with the tube diameter for each flow path in order to have the proper volume of reagent, etc in the flow cell at a given time.

An exemplary pump of the invention (as shown a syringe pump) can be seen in FIGS. 3-7. It will be appreciated that the pump is shown without attached syringes, tubing or fluid connections. Again, however, illustration of a particular pump herein should not be taken as limiting. Other types and kinds of pumps are also optionally utilized as a component of the current invention. The exemplary pump shown is typically placed distal to the flow cell and manifold and optionally distal or proximal to the final waste reservoir. However, as will be appreciated, pumps can be used in either the "push" or "pull" mode, depending whether the pump is connected before or after the flow cell.

In some embodiments, the invention can also comprise one or more pumps proximal to the flow cell and manifold (e.g., between the flow cell/manifold and the multi-way valve). For example, some embodiments comprise a priming pump (e.g., a solenoid pump) that can prime the proximal fluidic components so that when the distal pump pulls fluid through the flow cell, a bolus of air is not produced that could be damaging or detrimental to the flow cell, cluster formation, etc.

In addition to the one or more pumps to draw/push fluids through the components of the invention, typical embodiments herein also comprise one or more valves to properly direct the fluids in the various lines. For example, the embodiments illustrated in the accompanying figures optionally comprise a multi-way valve, e.g., a 26 way valve, connected to the various reagent reservoirs which directs the correct fluid into the flow cell at the correct time. Such multi-way valves (e.g., such as those produced by VICI, Valco Instruments Company, Inc.) are well known to those of skill in the art. The timing and control of the valve, and hence the control of which reagents are sent to the flow cell and for how long and at what rate, are typically controlled by the computer component. Additional splitter valves are also optionally present in various embodiments herein.

Figure 21:
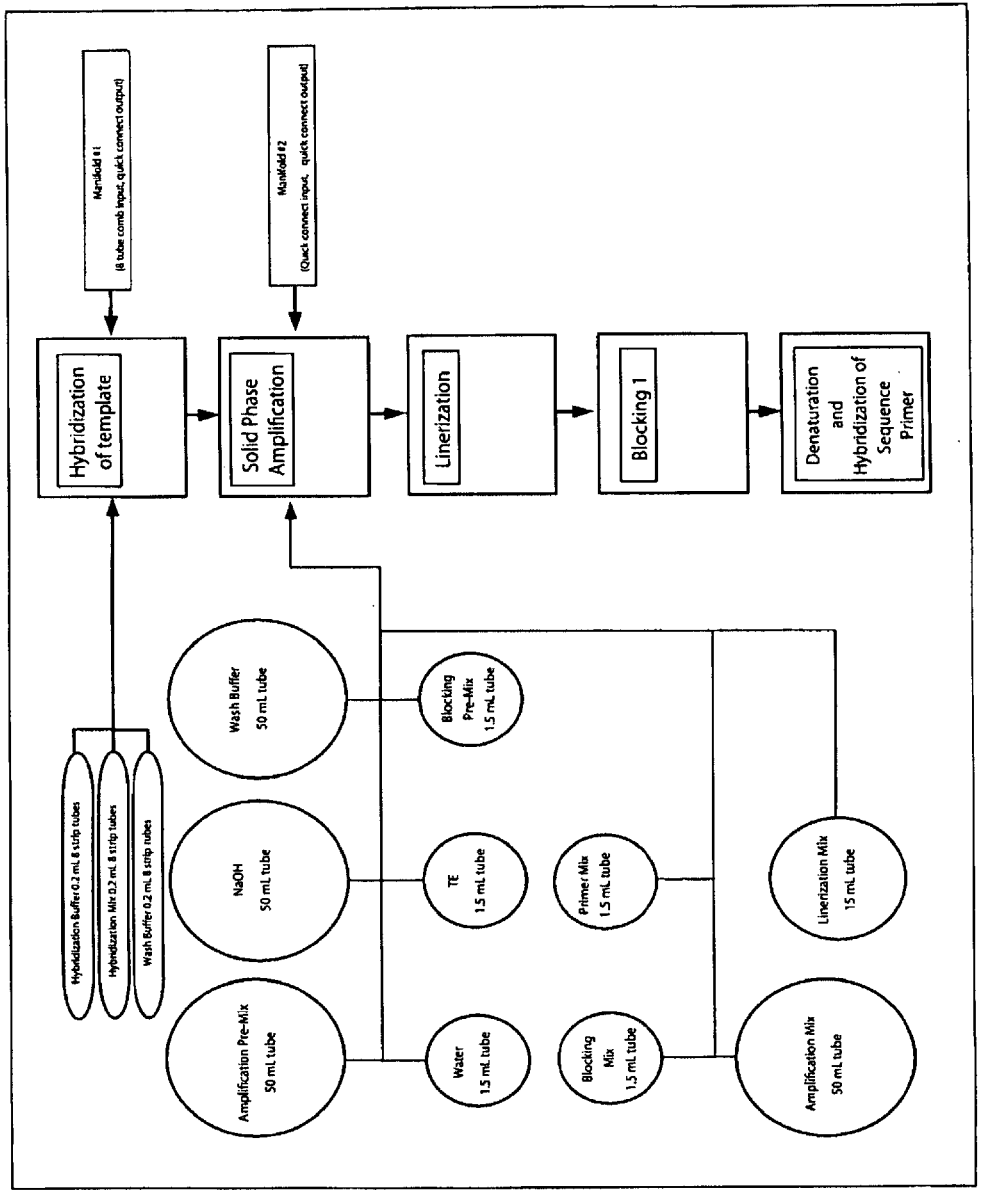
FIG. 21 shows a schematic diagram outlining general component areas of the invention and their relation to one another.
Figure 24A:
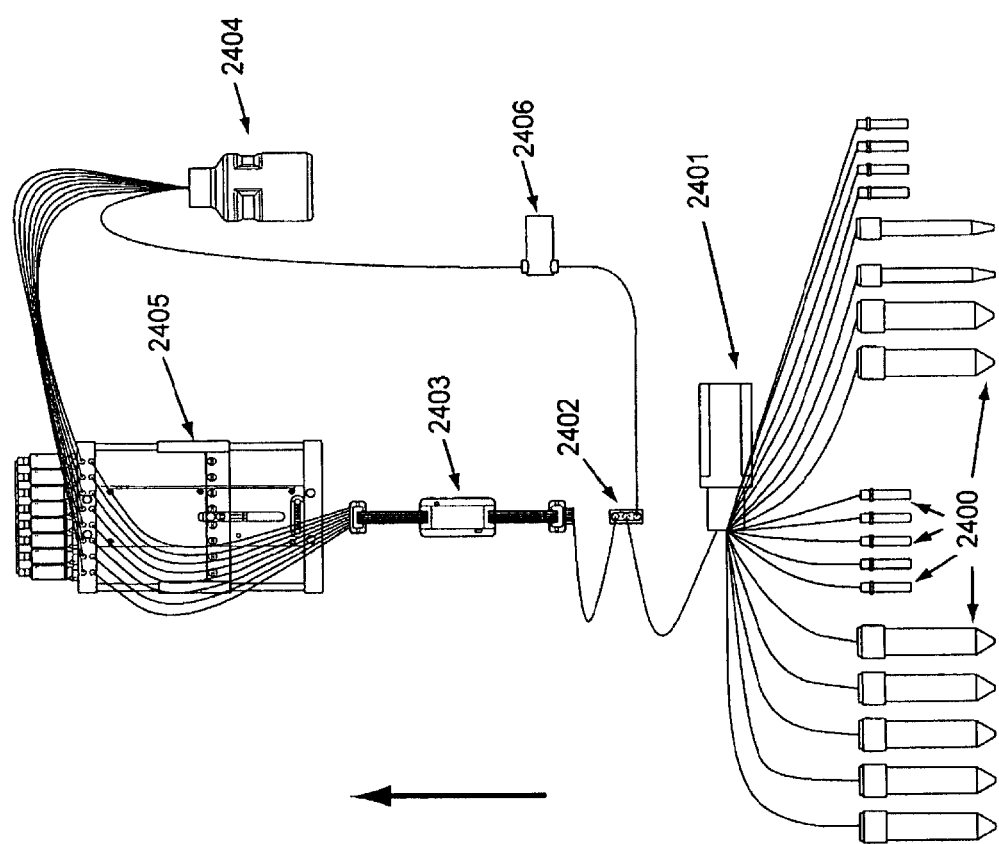
FIG. 24A is an exemplary schematic diagram showing a path fluid travels from the reagent storage areas into waste.
Figure 24B:
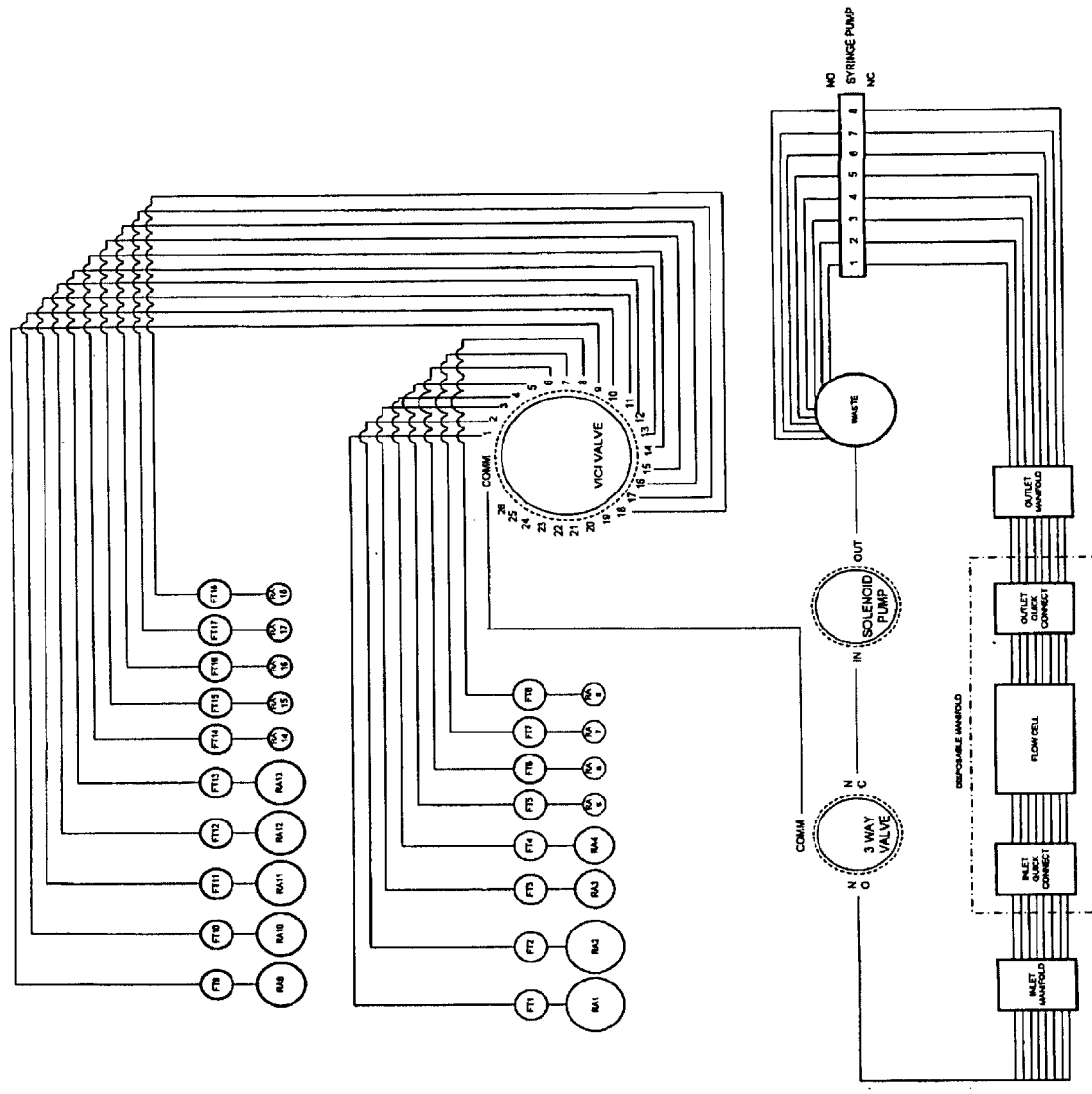
FIG. 24B is a schematic diagram of an exemplary fluidic arrangement.

FIG. 21 gives a schematic overview of typical components and steps involved with use of the current invention. Thus, FIG. 21 indicates during what steps (e.g., amplification) certain reagents are used, which manifolds are used, etc. FIG. 24A shows an exemplary schematic showing the typical path fluids travel from the reagent storage areas 2400, through multiport valve 2401, and three-way valve 2402, into manifold 2403, and eventually into waste 2404. Pump 2405 (as shown a syringe pump) is also shown, as well as by-pass pump 2406 which can be used to draw reagents from their reservoirs up to just before the manifold connection areas in order to prevent air boluses and dry lines. FIG. 24B shows a similar schematic diagram of an exemplary fluidic arrangement. In FIG. 24B, "comm" stands for common port, while "rt" stands for reagent bottle (reservoir) and "ft" stands for fee through.

It will be appreciated that the pumps which direct the fluid flow within the systems/devices of the invention can be "push" or "pull" pumps. In other words, in some embodiments, certain pumps can be located distal to the flow cell (i.e., between the flow cell and the waste reservoir or after the waste reservoir) while in other embodiments, certain pumps can be located proximal to the flow cell (i.e., between the flow cell and the reagent storage areas). Pumps located distal to the flow cell act to "pull" fluids through the flow cell, while proximal pumps "push" fluids through the flow cell and/or "pull" fluids up to a point before the flow cell.

Power Supply and Computer

As noted above, the various components of the present system are coupled to an appropriately programmed processor or computer that functions to instruct the operation of these instruments in accordance with preprogrammed or user input instructions, receive data and information from these instruments, and interpret, manipulate and report this information to the user. As such, the computer is typically appropriately coupled to these instruments/components (e.g., including an analog to digital or digital to analog converter as needed).

The computer optionally includes appropriate software for receiving user instructions, either in the form of user input into set parameter fields, e.g., in a GUI, or in the form of preprogrammed instructions, e.g., preprogrammed for a variety of different specific operations. The software then converts these instructions to appropriate language for instructing the correct operation to carry out the desired operation (e.g., of fluid direction and transport, etc.).

For example, the computer can optionally control pumping (both in terms of timing and volume) of the various buffers, reagents, etc. used to amplify nucleic acid clusters in the flow cells herein. The fluid flow component optionally directs the movement of the appropriate buffers, nucleotides, enzymes, etc., into and through the flow cell.

The computer also optionally receives the data from the one or more sensors/detectors included within the system, and interprets the data, either provides it in a user understood format, or uses that data to initiate further controller instructions, in accordance with the programming, e.g., such as in monitoring and control of flow rates, temperatures, and the like.

In the present invention, the computer typically includes software for the monitoring and control of materials in the flow cells. The computer also typically provides instructions, e.g., to the heating component and reagent flow components, etc. In various embodiment, the computer component of the invention can be completely pre-set, wherein the user can choose between protocols that are preloaded into the computer. Alternatively, the computer can be partially pre-set, wherein the user can select some or all parameters of the protocols. Examples of choosable parameters can include, e.g., temperature of the flow cell (such as during the isothermal cluster creation step) as well as the temperature ramp rate; flow rate, flow volume, and order of flow from the various reagent reservoirs including priming set ups; and number of isothermal amplification cycles. The pre-set and partially pre-set protocols can include, e.g., a servicing protocol to run wash buffers, etc. through the device; an amplification only protocol which starts with hybridization of template molecules onto the flow cell followed by isothermal amplification; a linearization-blocking-primer hybridization protocol wherein double stranded DNA clusters (after amplification) are chemically linearized and their 3' OH ends are blocked followed by hybridization of a sequencing primer onto the single stranded DNA in preparation for sequencing; an amplification-linearization-blocking protocol wherein template molecules are hybridized onto the flow cell followed by isothermal amplification, linearization, and blocking in preparation for sequencing; a linearization-blocking protocol; a primer hybridization only protocol; and a "full process" protocol including template hybridization, amplification, linearization, blocking and primer hybridization. See below.

Any controller or computer optionally includes a monitor which is often a cathode ray tube ("CRT") display, a flat panel display (e.g., active matrix liquid crystal display, liquid crystal display), or the like. Information produced from the current systems, e.g., temperature regulation of the flow cell, is optionally displayed in electronic form on the monitor. Additionally, such data can be outputted in printed form. The data, whether in printed form or electronic form (e.g., as displayed on a monitor), can be in various or multiple formats, e.g., curves, histograms, numeric series, tables, graphs and the like.

Computer circuitry is often placed in a box which includes, e.g., numerous integrated circuit chips, such as a microprocessor, memory, interface circuits. The box also optionally includes a hard disk drive, a floppy disk drive, a high capacity removable drive such as a writeable CD-ROM, and other common peripheral elements. Inputting devices such as a keyboard or mouse optionally provide for input from a user and for user selection of sequences to be compared or otherwise manipulated in the relevant computer system. In various embodiments, the computer is separate from the other components of the device illustrated herein. Thus, the computer is optionally electronically connected to the current device, e.g., through one or more USB connection or the like. See FIG. 4 showing a RS232 USB to serial adapter (e.g., a Perle USB to Serial Adapter) which communicates with the thermal regulators, pump(s), etc., and which is connected via USB to an external computer.

Power can be supplied to the current invention, e.g., through one or more power source. Such power sources are optionally housed within the chassis, see FIG. 5, etc., or can be external. Various embodiments can comprise single or multiple power sources (e.g., different power sources for different components within the device). Those of skill in the art will appreciate that the power sources can be of variable strength depending upon, e.g., the particular configurations of the device, the number of reagent reservoirs, the type of temperature controllers, etc.

Amplification Kits

The present invention also provides kits for conducting nucleic acid amplification/cluster formation. In particular, such kits typically include e.g., devices/systems as described herein, as well as optionally modules and workstations for performing the nucleic acid amplifications. A kit optionally contains additional components for the assembly and/or operation of a multimodule workstation including, but not restricted to robotic elements (e.g., a track robot, a robotic armature, or the like), fluid handling devices, and additional computers (including e.g., input devices, monitors, c.p.u., and the like).

The devices/systems described herein are optionally packaged to include reagents for performing the device's functions. For example, the kits can optionally include any of the devices described, along with assay components, flow cells, buffers, reagents, enzymes, sample materials, control material, immiscible fluids, etc., for performing the amplifications of the invention. In the case of prepackaged reagents, the kits optionally include pre-measured or pre-dosed reagents that are ready to use in the current devices without measurement, e.g., pre-measured fluid aliquots, or pre-weighed or pre-measured solid reagents that can be easily reconstituted by the end-user of the kit.

Such kits also typically include appropriate instructions for using the reagents, and in cases where reagents are not predisposed in the devices themselves, with appropriate instructions for introducing the reagents into the reservoirs of the device. In the latter case, these kits optionally include special ancillary devices for introducing materials into the reagent reservoirs, e.g., appropriately configured syringes/pumps, or the like.

Optionally, the reagents are provided in a stabilized form (whether or not they need to be reconstituted), so as to prevent degradation or other loss during prolonged storage, e.g., from leakage. A number of stabilizing processes are widely used for reagents that are to be stored, such as the inclusion of chemical stabilizers (e.g., enzymatic inhibitors, microbicides/bacteriostats), the physical stabilization of the material, such as through immobilization on a solid support, entrapment in a matrix (e.g., a bead, a gel, etc.), lyophilization, or the like.

In some embodiments, a kit of the invention can comprise reagents such as cluster buffer, amplification additive, dNTP mix, Taq DNA polymerase, 10× blocking buffer, cobalt chloride, ddNTP mix (blocking), TdT, sodium hydroxide, TB, and sequencing primer (all optionally stored/kept at −20° C. or −4° C.), as well as water, hybridization buffer, wash buffer, 2M sodium hydroxide, sodium periodate, and ethanolamine or propanolamine (all optionally stored/kept at ambient temperature). The composition of individual buffers are detailed in the illustration/protocol sections below. The amount or volume of such reagents can comprise enough for 1 nucleic acid amplification reaction or for multiple reactions. The reagents are optionally ready to be used or optionally one or more of them need to be properly aliquoted, reconstituted, etc. prior to use. In other embodiments, kits herein do not comprise reagents, buffers, etc., whether pre-packaged or not.

The elements of the kits of the present invention are typically packaged together in a single package or set of related packages. The package optionally includes instructions (e.g., written or recorded instructions) for carrying out one or more amplification reaction in accordance with the description herein. Such instructions can optionally comprise DVDs, CDs, pamphlets, books/booklets, inserts, posters, etc. The kit can also comprise references to a website or URL where instructions can be accessed. Kits also optionally include packaging materials or containers for holding the device, system or reagent elements.

The kits can also optionally include reservoirs (e.g., vials, etc.) for the various reagents and for the nucleic acid samples. The kits also can include flow cells (optionally pre-treated to be ready for hybridization, etc.); multiple manifolds, etc.

Illustration of Flow Cell Preparation, Cluster Creation, and Preparation of Clusters for Sequencing The following illustrations/examples of protocols, etc. describe exemplary expositions of various embodiments of the invention as described herein. Preparation and sequencing of clusters are also described in copending applications WO/06064199 and WO/07010251, whose protocols are included herein by reference in their entirety.

While specific details are given herein concerning preparation of reaction surfaces for flow cells, etc., in many embodiments (e.g., systems/devices of the invention comprising flow cells, especially those in kits, etc.), appropriate flow cells already prepared to receive nucleic acid targets are included or are available prepared separately. Thus, in many embodiments, the end-user of the device or kit does not necessarily need to surface treat the flow cells, etc.

Preparation of Flow Cells for DNA Hybridization

Prior to creation of nucleic acid cluster arrays through use of the invention, appropriate surface areas (e.g., surfaces within channels in flow cells) are typically prepared onto which the clusters are to be created. While exemplary preparation set-ups for flow cell surfaces are described herein, it will be appreciated that other surface preparations are also possible. In other words, in some embodiments the systems and devices of the invention can be utilized with surfaces prepared in ways other than those presented herein.

Acrylamide Coating of Flow Cells

The solid supports used are typically 8-channel glass flow cells such as those provided by Silex Microsystems (Sweden). However, again, the experimental conditions and procedures are readily applicable to other solid supports as explained throughout. See Systems and Devices for Sequence by Synthesis Analysis," U.S. Ser. No. 60/788,248, filed Mar. 31, 2006 and International Application PCT/US2007/007991, filed Mar. 30, 2007.

In the current illustrations, the flow cells can be washed as follows: neat Decon for 60 min, milliQ $H_2O$ for 10 min, NaOH 1N for 15 min, milliQ $H_2O$ for 10 min, HCl 0.1N for 15 min, milliQ 1-120 for 10 min.

Polymer Solution Preparation

A polymerization solution is prepared to be applied to the flow cell surface. For 10 ml of 2% polymerization mix are combined: 10 ml of 2% solution of acrylamide in milliQ $H_2O$; 412.5 µl of a 100 mg/ml N-(5-bromoacetamidylpentyl) acrylamide (BRAPA) solution in DMF (42 mg in 420 µl DMF); 11.5 µl of TEMED; and, 100 µl of a 50 mg/ml solution of potassium persulfate in milliQ $H_2O$ (20 mg in 400 µl H2O).

The 10 ml solution of acrylamide is first degassed with argon for 15 min. The solutions of BRAPA, TEMED and potassium persulfate are successively added to the acrylamide solution. The mixture is then quickly vortexed and immediately flowed into the channels of the flow cell. Polymerization is then carried out for 1 h 30 at RT. Afterwards the channels are washed with milliQ $H_2O$ for 30 min and filled with 10 mM potassium phosphate buffer for storage until required.

Synthesis of N-(5-bromoacetamidyipentyl) acrylamide (BRAPA)

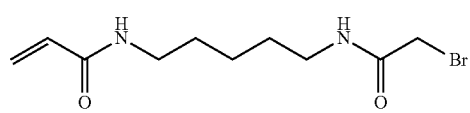
(1)

N-Boc-1,5-diaminopentane toluene sulfonic acid is obtainable from, e.g., Novabiochem (EMD Biosciences/Merck Biosciences, Darmstadt, Germany). The bromoacetyl chloride and acryloyl chloride can be obtained from, e.g., Fluka (Sigma-Aldrich Chemie, Buchs, Switzerland). All other reagents can be obtained from, e.g., Aldrich products (St. Louis, Mo.).

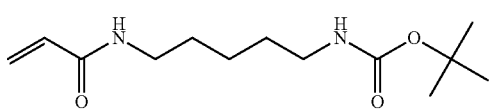
(2)

To a stirred suspension of N-Boc-1,5-diaminopentane toluene sulfonic acid (5.2 g, 13.88 mmol) and triethylamine (4.83 ml, 2.5 eq) in THF (120 ml) at 0° C. is added acryloyl chloride (1.13 ml, 1 eq) through a pressure equalized dropping funnel over a one hour period. The reaction mixture is then stirred at room temperature and the progress of the reaction checked by TLC (petroleum ether:ethyl acetate 1:1). After two hours, the salts formed during the reaction are filtered off and the filtrate evaporated to dryness. The residue is purified by flash chromatography (neat petroleum ether followed by a gradient of is acetate up to 60%) to yield 2.56 g (9.98 mmol, 71%) of product 2 as a beige solid. 1H NMR (400 MHz, d6-DMSO): 1.20-1.22 (m, 2H, CH2), 1.29-1.43 (m, 13H, tBu, 2×CH2), 2.86 (q, 2H, J=6.8 Hz and 12.9 Hz, CH2), 3.07 (q, 2H, J=6.8 Hz and 12.9 Hz, CH2), 5.53 (dd, 1H, J=2.3 Hz and 10.1 Hz, CH), 6.05 (dd, 1H, J=2.3 Hz and 17.2 Hz, CH), 6.20 (dd, 1H, J=10.1 Hz and 17.2 Hz, CH), 6.77 (t, 1H, J=5.3 Hz, NH), 8.04 (bs, 1H, NH). Mass (electrospray+) calculated for C13H24N2O3 256, finds 279 (256+Na+).

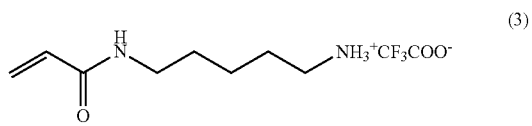
(3)

Product 2 (2.56 g, 10 mmol) is dissolved in trifluoroacetic acid:dichloromethane (1:9, 100 ml) and stirred at room temperature. The progress of the reaction is monitored by TLC (dichloromethane:methanol 9:1). On completion, the reaction mixture is evaporated to dryness, the residue co-evaporated three times with toluene and then purified by flash chromatography (neat dichloromethane followed by a gradient of methanol up to 20%). Product 3 is obtained as a white powder (2.43 g, 9 mmol, 90%). 1H NMR (400 MHz, D2O): 1.29-1.40 (m, 2H, CH2), 1.52 (quint., 2H, J=7.1 Hz, CH2), 1.61 (quint., 2H, J=7.7 Hz, CH2), 2.92 (t, 2H, J=7.6 Hz, CH2), 3.21 (t, 2H, J=6.8 Hz, CH2), 5.68 (dd, 1H, J=1.5 Hz and 10.1 Hz, CH), 6.10 (dd, 1H, J=1.5 Hz and 17.2 Hz, CH), 6.20 (dd, 1H, J=10.1 Hz and 17.2 Hz, CH). Mass (electrospray+) calculated for C8H16N20 156, finds 179 (156+Na+).

To a suspension of product 3 (6.12 g, 22.64 mmol) and triethylamine (6.94 ml, 2.2 eq) in THF (120 ml) is added bromoacetyl chloride (2.07 ml, 1.1 eq), through a pressure equalized dropping funnel, over a one hour period and at −60° C. (cardice and isopropanol bath in a dewar). The reaction mixture is then stirred at room temperature overnight and the completion of the reaction checked by TLC (dichloromethane:methanol 9:1) the following day. The salts formed during the reaction are filtered off and the reaction mixture evaporated to dryness. The residue is purified by chromatography (neat dichioromethane followed by a gradient of methanol up to 5%). 3.2 g (11.55 mmol, 51%) of the product 1 (BRAPA) are obtained as a white powder. A further recrystallization performed in petroleum ether:ethyl acetate gives 3 g of the product 1.1H NMR (400 MHz, d6-DMSO): 1.21-1.30 (m, 2H, CH2), 1.34-1.48 (m, 4H, 2×CH2), 3.02-3.12 (m, 4H, 2×CH2), 3.81 (s, 2H, CH2), 5.56 (d, IH, J=9.85 Hz, CU), 6.07 (d, 1H, J=16.9 Hz, CH), 6.20 (dd, 1H, J=10.1 Hz and 16.9 Hz, CH), 8.07 (bs, 1H, NH), 8.27 (bs, 1H, NH). Mass (electrospray+) calculated for C1OH17BrN2O2 276 or 278, finds 279 (278+H+), 299 (276+Na+).

Grafting Primers onto Surface of SFA Coated Flow Cell

Once the flow cell is appropriately coated, as explained above, primers can be optionally grafted onto the surface for the target nucleic acids to interact with. Thus, an acrylamide coated flow cell is placed onto a modified thermocyler with an attached peristaltic pump (e.g., a modified MJ-Research thermocyler attached to a peristaltic pump). Grafting mix optionally consisting of 0.5 µM of a forward primer and 0.5 µM of a reverse primer in 10 mM phosphate buffer (pH 7.0) is pumped into the channels of the chip at a flow rate of 60 µl/mm for 75 s at 20° C. The thermocyler is then heated up to 51.6° C., and the flow cell is incubated at this temperature for 1 hour. During this time, the grafting mix undergoes 18 cycles of pumping. Grafting mix is pumped in at 15 µl/mm for 20 s, then the solution is pumped back and forth (5 s forward at 15 µl/min, then 5 s backward at 15 µl/mm) for 180 s. After 18 cycles of pumping, the chip is washed by pumping in 5×SSC at 15 µl/min for 300 s at 51.6° C. The thermocyler is then cooled to 20° C.

The primers can be, as typical, 5'-phosphorothioate oligonucleotides incorporating any specific sequences or modifications required for cleavage. Primers' sequences and suppliers can vary according to the experiment they are to be used for, and can be complementary to the 5'-ends of the template duplex. For example, the DNA sequence used can be a single monotemplate sequence of 363 bases, with ends complimentary to the grafted primers. The full sequence of an exemplary template duplex is shown in FIG. 23. The duplex DNA is denatured using sodium hydroxide treatment followed by snap dilution as described.

The amplified clusters can contain a diol linkage in one of the grafted primers. Diol linkages can be introduced by including a suitable linkage into one of the primers used for solid-phase amplification.

Suitable primers including any desired template-specific sequence can be manufactured by standard automated DNA synthesis techniques using components available from commercial suppliers (e.g. Fidelity Systems Inc., ATD).

A cleavable diol-containing primer would typically have the following structure:

5'-phosphorothioate-arm26-diol22A-sequence-3'OH

Wherein "sequence" represents a sequence of nucleotides capable of hybridizing to the template to be amplified.

The structures of the arm26 and diol22A components (from Fidelity Systems Inc, MD, USA) are as follows:

simultaneously to seed the surface of a single flow cell, thus leading to a heterogeneous cluster population wherein each cluster consists of many identical copies of the original template molecule for that cluster.

Creation of nucleic acid clusters by the current invention involves flowing a series of solutions through a flow cell, while controlling reaction times and flow rates. The temperature of the flow cell and the flow rate are carefully controlled using pumps (e.g., syringe pump, peristaltic pumps) and temperature control components (e.g., thermoelectric controllers such as heating blocks), all of which are computer controlled. However, in some embodiments the current invention is not fully automated and an operator can still be required to change the solutions between the various steps and/or change manifolds, etc.

The process of nucleic acid cluster formation by the instrumentation of the invention typically consists of a number of sequential steps designed to seed and grow the clusters. Additional steps can be performed by the current instrumentation to prepare the nucleic acid of the clusters for sequencing, e.g., via SBS sequencing. Typical steps performed with the instru-

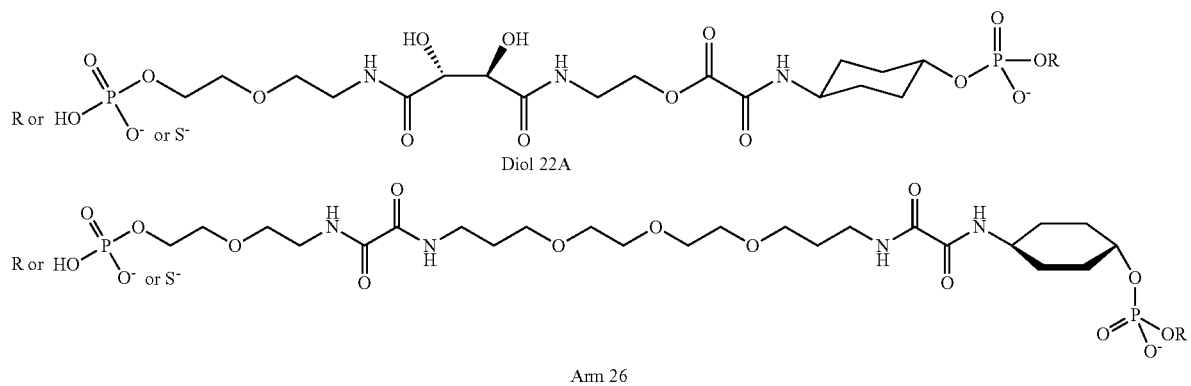

Diol 22A

Arm 26

Products containing such diol linkages can be cleaved using periodate and propanolamine as described, and the resulting single stranded polynucleotides hybridized as described.

The grafted primers can contain a sequence of T bases at the 5'-end to act as a spacer group to aid linearization and hybridization. Sequences of two exemplary primers that can be grafted to the flow cell are:

PS-TTTTTTTTTT-ARM 26-Diol 22A-AATGATACGGCGACCACCGA and

PS-TTTTTTTTTTCAAGCAGAAGACGGCATACGA.

Set-Up and Usage of Isothermal Amplification Hardware

The following are illustrations and examples of general techniques and protocols for nucleic acid cluster formation showing exemplary use of the systems/devices of the invention. It will be appreciated that such descriptions and examples are not necessarily limiting upon the current invention unless specifically stated to be so.

In use of the current instrumentation one or more single DNA fragments (i.e., template DNA) is typically attached to a surface such as the surface of a specially coated flow cell, e.g., as illustrated above (see above) and amplified to form a surface bound colony (or cluster). It will be appreciated that hundreds of millions of different DNA fragments can be used mentation herein include: "template hybridization" wherein the surface of a flow cell is seeded with sample DNA fragments and "amplification," wherein multiple copies of DNA are made from the original templates to form the clusters.

Other steps optionally performed by the present instrumentation can include: "linearization" to convert dsDNA of the clusters to ssDNA suitable for sequencing; "blocking" which prevents non-specific sites from being sequenced; "denaturation" to convert dsDNA to ssDNA; and "hybridization of sequencing primer" for initiation of DNA sequencing.

As an overview, in use of the current instrumentation, a flow cell is placed in the appropriate location on the instrumentation (e.g., as described above) in fluid communication with a sample manifold. The various DNA samples to be amplified are drawn out of the sample reservoirs into the different channels of the flow cell. The sample manifold is then removed and replaced with a common/reagent manifold that is in fluid communication with the various reagent reservoirs and the flow cell. The DNA is then amplified by having the appropriate reagents flowed through the flow cell in the proper sequence and at the proper rate under isothermal conditions. The fluid flow is controlled by the pump(s) and control valve(s) under direction of the computer.

As explained above, various configurations of the current instrumentation comprise a number of areas and/or components. In typical embodiments, the flow cell (usually, but not exclusively) comprising eight channels and typically pretreated to make the channels conducive to cluster formation, is placed over, and in thermal communication with, the temperature control block (e.g., Peltier, TEC).

In typical embodiments, the flow cells are handled to ensure and/or ameliorate any chance of DNA contamination, e.g., the flow cell is handled using either plastic tweezers or clean gloves. Additionally, the flow cells are handled so that the channels are not drained of any storage solution. The flow cells are placed over the temperature control component (which ensures isothermal conditions at the desired temperature). In some embodiments, the flow cells optionally comprise markings or other indications which let the user know the proper orientation/placement of the flow cell.

A manifold, which includes input and output tubes for each channel, is then placed over the flow cell and held in place by a clamp. In particular embodiments, the input (proximal) tubes going into the manifold can be, e.g., 10.5 cm long (short end) while the output tubes can be, e.g., 20 cm (long end). Of course, it will be appreciated that such lengths should not necessarily be taken as limiting. While, in some embodiments, one end of the manifold comprises shorter tubing in order to aid in orientation, in typical embodiments, both proximal and distal tubes are of the same length, e.g., 13 cm long. As detailed above, in particular embodiments, sample manifolds can comprise comb piece or sealing strip 910, on the proximal tubes to facilitate the introduction of the DNA samples from an 8-tube sample reservoir, while the distal tube ends into quick fit connector 950. See FIG. 9. In some embodiments, a reagent manifold has both proximal and distal tubes terminating into quick fit connectors 1100 and 1104 as in FIG. 11A.

As with the flow cells, in typical use of the current invention the manifolds are handled so as to prevent unwanted DNA contamination, e.g., gloves are worn when handling the manifolds, etc.

The samples used in cluster formation are drawn into the flow cell from an eight-tube strip reservoir or sample reservoir. The eight-tube sample reservoir can be held on a rack close to the flow cell so that the inlet tubes can be dipped into the eight-tube samples. Again, use of eight samples, eight flow cell channels, etc. should not necessarily be taken as limiting. Other embodiments can comprise flow cells having, e.g., six channels. In such embodiments, there would thus preferably be six tubes from six samples, etc.

As described above, the samples are then drawn into their appropriate flow cell channel from the individual sample reservoirs. A pump, e.g., an 8-way peristaltic or syringe pump such as, but not limited to Kloehn® V6 Model 8 Syringe Pump, can be used to load the samples into the channels of the flow cell. The pump can be connected to the distal flow cell outlet tubes and run forwards (i.e., pulling fluids). After the samples are loaded into the channels, the waste solutions are collected at the pump outlets and disposed of in the waste reservoir. As discussed above, however, various embodiments can comprise pump arrangements wherein at least one pump pushes fluid through the flow cell rather than pulling it through the flow cell and/or pulls fluid up to but not through the flow cell.

Also as explained above, the reactions within the flow cells are kept under temperature control (e.g., isothermal or substantially isothermal conditions during cluster formation) by the temperature controller which can comprise, e.g., a metal block such as copper or aluminum for heat diffusion, as well as one or more heaters (e.g., Peltier or other TEC). In particular embodiments, the temperature control components do not comprise an active cooling component used during the isothermal amplification.

The various components of the current instrumentation are typically controlled by computer. The script program used is described in more detail below.

After the DNA cluster formations are completed (or, optionally, when the DNA clusters are completed and the DNA within the clusters is denatured, etc. in preparation for sequencing), the manifold and the flow cell are removed from the body of the device. The flow cell is then optionally rinsed with water or storage buffer, etc.

Before the solutions are run through the instrumentation herein, clean water or buffer is optionally run through the tubing, manifold, and flow cell prior to nucleic acid amplification as described above for the "wash connection."

The tables and description provided in the illustrations/protocols herein indicate exemplary solutions required, exemplary volumes per channel to be dispensed, and exemplary times to the next solution change, etc. The volumes specified in the sample protocols/illustrations are in excess of what is optionally pumped to avoid air being drawn into the flow cell during the process. Again it is to be emphasized that the examples given herein are for illustrative purposes only and should not necessarily be taken as limiting.

Table 1 presents a brief overview of the five optional steps performed by the instrumentation herein.

TABLE 1

The cluster creation protocol can be divided into the following steps:

| Step | Time for Each Step | Solution Change | Reagent Name | Time for Each Reagent |
|---|---|---|---|---|
| 1 Template Hybridization and Initial Extension | 38 min | 1 | Hybridization Buffer | 2 min |
| | | 2 | Template Mix | 25 min |
| | | 3 | Wash Buffer | 5 min |
| | | 4 | Amplification Pre-mix* | 3 min |
| | | | | 20 s |
| | | 5 | Initial Extension Mix with Taq Polymerase* | 3 min |
| 2 Isothermal Amplification | 2 h 10 min (35 cycles) | 6 | Formamide | 56 s |
| | | 7 | Amplification Pre-mix* | 56 s |
| | | 8 | Amplification Mix with Bst Polymerase* | 72 s |
| Safe Stopping Point | | | | |
| 3 Linearization | 25 min | 9 | Cleaving Solution* | 20 min |
| | | 10 | Water | 5 min |
| 4 Blocking | 43 min | 11 | 1X Blocking Buffer* | 5 min |
| | | 12 | Blocking Mix* | 33 min |
| | | 13 | Wash Buffer | 5 min |
| Safe Stopping Point | | | | |
| 5 Denaturation and Hybridization of Sequencing Primer | 35 min | 14 | NaOH | 5 min |
| | | 15 | TE | 5 min |
| | | 16 | Sequencing Primer Mix* | 20 min |
| | | 17 | Wash Buffer | 5 min |
| Ready for sequencing. Do not store flow cell. | | | | |
| Total Time | ≈4 h 30 min | | *These solution are made fresh, e.g., using Kit reagents | |

As will be appreciated, in various embodiments, the cluster formation, etc. can be stopped or paused during the protocols. For example, amplification (step 2) can be run and the flow cell cooled to room temperature at the end of the amplification. Alternatively, the procedure can be stopped at the end of step 2 or step 4 and continued later.

In many embodiments, after creation of the nucleic acid clusters and preparation of the nucleic acid of the clusters for sequencing, at the end of step 5, the flow cell is transferred directly to a sequencing instrument.

Template DNA Hybridization and First Extension

In particular embodiments, template hybridization and first extension are combined in the same procedure and are run sequentially with no interruption between the two steps.

The flow cell as presented herein typically, but not exclusively, comprises eight parallel channels. Therefore up to eight different DNA samples can be processed simultaneously (i.e., one per channel). When processing a sample for the first time a concentration range is optionally performed in order to optimize the concentration. If the DNA concentration is too low, the clusters can be too few and the throughput too low. However, if the DNA concentration is too high, the clusters can be too dense and can overlap, complicating the data analysis. Preferably, the concentration of DNA is in the range of 0.2-2 pM thus resulting in a desired cluster density, e.g., of about 10K/tile. If the DNA sample is stored at very low concentration (≥1 nM), it is preferably stored in TE/0.1% tween at −20° C. to improve its long-term stability.

During template hybridization and first extension, a number of solutions/buffers are typically employed, e.g., a solution comprising the DNA samples, a hybridization buffer (5×SSC/0.1% tween), a wash buffer (0.3×SSC/0.1% tween), a 2M sodium hydroxide solution, a cluster buffer (200 mM Tris, 100 mM Ammonium Sulfate, 20 mM Magnesium sulfate, 1% Triton, 13% DMSO, pH 8.8); an amplification additive (5 M betaine), DNA polymerase, and 10 mM dNTP mix.

To prepare the hybridization mixes, a 0.2 ml strip sample tube and the hybridization buffer are pre-chilled. Using 1.7 ml Eppendorf tube(s), the DNA template(s) are then diluted to mM in buffer EB (Qiagen). 1 µL of 2M NaOH is added to 19 µL of template, vortexed briefly and incubated for 5 minutes at room temperature to denature the DNA template into single strands. The denatured DNA is diluted to working concentration (0.2-2 pM) in pre-chilled hybridization buffer (e.g. for 1 mL of 1 pM Hybridization mix, 1 µL of denatured DNA is diluted into 1 mL of pre-chilled hybridization buffer). The volume required depends on the number of channels used at least 120 µL of hybridization mix per channel is optionally used. Thus, 1 mL of hybridization mix is enough for 8 channels. The samples are vortexed briefly, spun down and aliquoted into the pre-chilled 0.2 ml strip tubes (with no bubbles in the bottom of the tubes) and used immediately.

To prepare the Amplification pre-mix (of volume enough for the first extension and 35 cycles of isothermal amplification), 35 mL of $H_2O$ (milliQ), 7 mL of Cluster buffer (200 mM Tris, 100 mM Ammonium Sulfate, 20 mM Magnesium sulfate, 1% Triton, 13% DMSO, pH 8.8), and 28 mL of Amplification additive (5 M betaine solution) are mixed to achieve a final volume of 70 mL.

To prepare the first extension Taq mix, 780 µL of Amplification pre-mix, 16 µL of 10 mM dNTPs, and 4 µL of Taq DNA polymerase are mixed together for a final volume of 800 µl.

A typical amplification process is detailed in the following table (Table 2), detailing the flow volumes per channel, controlled automatically by the computer component of the invention:

TABLE 2

| Step | Description | T (° C.) | Time (sec) | Flow rate (µl/min) | Pumped V (µl) |
|---|---|---|---|---|---|
| 1 | Pump Hybridization pre-mix | 20 | 120 | 603 | 120 |
| 2 | Pump Hybridization mix | 96 | 300 | 15 | 75 |
| 3 | Remove bubbles | 96 | 6 | 100 | 10 |
| 4 | Stop flow and hold T | 96 | 30 | static | 0 |
| 5 | Slow cooling | 96-40 | 1120 | static | 0 |
| 6 | Pump wash buffer | 40 | 300 | 15 | 75 |
| 7 | Pump amplification pre-mix | 40 | 280 | 15 | 70 |
| 8 | Pump amplification mix | 40 | 95 | 60 | 95 |
| 9 | First Extension | 74 | 90 | static | 0 |
| 10 | cool to room temperature | 20 | 0 | static | 0 |

Isothermal Amplification (38° C.) Using Sodium Hydroxide as Denaturant

In some embodiments, the DNA can be isothermally amplified into clusters at 38° C. using NaOH as a denaturant. As explained below, however, other typical embodiments comprise isothermal DNA amplification under different conditions.

Reagents used for isothermal amplification by the instrumentation herein can comprise: 0.1M NaOH; 0.3×SSC with 0.1% Tween 20; Amplification pre-mix (see above); 10 mM dNTP mix; and Bst DNA polymerase 8,000 U/ml (NEB part no M0275L). To prepare isothermal Bst mix (of enough volume for 35 cycles), 35 mL of amplification pre-mix, 0.7 mL of 10 mM dNTPs, and 0.35 mL of Bst DNA polymerase are mixed for a final volume of 36.05 mL. (NEB—New England Biolabs, Ipswich, Mass.).

The tubing lines of the instrumentation are typically primed prior to isothermal amplification. For example 0.1 M NaOH is run through the tubing followed by a wash of $H_2O$ and then 0.3×SSC/0.1% Tween. Also, as described above, the specific reagents are primed within their respective tubes. In other words, the reagents are drawn up into the tubes to avoid air boluses in the lines.

The isothermal amplification (including both temperature control and reagent control) is overseen by the computer component. Tables 3 and 4 give outlines of exemplary script controls. After the isothermal amplification occurs the nucleic acid of the clusters is ready to be linearized (see below).

TABLE 3

| Solution | Solutions required | Volumes per channel | Time required for each step |
|---|---|---|---|
| 6 | 0.1M NaOH | 75 | 75 s |
| 7 | 0.3 × SSC/0.1% Tween | 120 | 120 s |
| 8 | Amplification pre-mix | 75 | 75 s |
| 9 | Bst mix | 95 | 95 s + 180 s incubation |

35 cycles of above, followed by final 0.3 × SSC/0.1% Tween wash for 120 s

TABLE 4

| Step | Description | T (° C.) | Time (sec) | Flow rate (µl/min) | Pumped V (µl) |
|---|---|---|---|---|---|
| (1) | Pump 0.1M NaOH | 38 | 75 | 60 | 75 |
| This | Pump 0.3 × SSC/0.1% Tween | 38 | 120 | 60 | 120 |
| sequence | Pump Amplification pre-mix | 38 | 75 | 60 | 75 |
| 35 | Pump Bst mix | 38 | 95 | 60 | 95 |
| times | Stop flow and hold T | 38 | 180 | static | 0 |
| 2 | Pump 0.3 × SSC/0.1% Tween | 38 | 120 | 60 | 120 |

Isothermal Amplification at 60° C. Using Formamide as Denaturant

In another exemplary embodiment, the DNA can be isothermally amplified into clusters at 60° C. using formamide as a denaturant. The isothermal amplification (including both temperature control and reagent control) is overseen by the computer component. Table 5 gives outlines of exemplary script controls. After the isothermal amplification, and optional washing step, occur, the nucleic acid of the clusters is ready to be linearized (see below).

TABLE 5

| Step | Description | T (° C.) | Time (sec) | Flow rate (μL/min) | Pumped V (μl) |
|---|---|---|---|---|---|
| (1) | Pump Formamide | 60 | 56 | 30 | 28 |
| This sequence 35 times | Pump Amplification pre-mix | 60 | 56 | 30 | 28 |
|  | Pump Bst mix | 60 | 72 | 30 | 36 |
| 2 | Pump wash buffer | 60 | 280 | 30 | 140 |
| 3 | Pump Storage Buffer | 20 | 380 | 15 | 95 |

Wash buffer = 0.3 × SSC/0.1% Tween
Amplification pre mix = 2M betaine, 20 mM Tris, 10 mM Anirnonium Sulfate, 2 mM Magnesium sulfate, 0.1% Triton, 1.3% DMSO, pH 8.8
Bst mix = 2M betaine, 20 mM Tris, 10 mM Ammonium Sulfate, 2 mM Magnesium sulfate, 0.1% Triton, 1.3% DMSO, pH 8.8 plus 200 μM dNTPs and 80 units/mL of Bst polymerase (NEB Product ref M0275L)
Storage Buffer = 5X SSC.

Linearization

After the DNA is isothermally amplified into clusters, the DNA strands are optionally linearized in preparation for sequencing, etc. To prepare the linearization mix 1429 μL of water, 64 mg of sodium periodate, 1500 μL of formamide, 60 μL of 1M Tris pH8, and 6011.4 μL of 3-aminopropanol are mixed for a final volume of 3 mL. The periodate is first mixed with the water while the Tris is mixed with the formamide. The two solutions are then mixed together and the 3-aminopropanol is added to that mixture.

To linearize the nucleic acid within the clusters formed within the flow cell channels, the computer component of the instrumentation flows the appropriate linearization buffer through the flow cell, e.g., as shown in the exemplary embodiments illustrated in Table 6.

TABLE 6

| Step | Description | T (° C.) | Time (sec) | Flow rate (μL/min) | Pumped V (μl) |
|---|---|---|---|---|---|
| 1 | Pump Linearization mix | 20 | 1200 | 15 | 300 |
| 2 | Pump water | 20 | 380 | 15 | 95 |

Blocking

To prepare the blocking pre-mix, 1360 μL of water, 170 μL of 10× blocking buffer (NEB buffer 4; product number B7004S, New England Biolabs, Ipswich, Mass.), and, 170 μL of cobalt chloride (25 mM) are mixed for a final volume of 1700 μL. To prepare the blocking mix 1065.13 μL of blocking pre-mix, 21.12 μL of 125 μM ddNTP mix, and 13.75 μL of TdT terminal transferase (NEB; part no M0252S) are mixed for a final volume of 1100 μL.

To block the nucleic acid within the clusters formed in the flow cell channels, the computer component of the instrumentation flows the appropriate blocking buffer through the flow cell, e.g., as shown in the exemplary embodiments illustrated in Table 7.

TABLE 7

| Step | Description | T (° C.) | Time (sec) | Flow rate (μL/min) | Pumped V (μl) |
|---|---|---|---|---|---|
| 1 | Pump Blocking pre-mix | 20 | 200 | 15 | 50 |
| 2 | Pump Blocking mix | 38 | 300 | 15 | 75 |
| 3 | 9 Cycles: pump blocking mix and wait | 38 | 9× (20 + 180) | 15/static | 45 |
| 4 | Pump wash buffer | 20 | 300 | 15 | 75 |

Denaturation and Hybridization of Sequencing Primer

Once the DNA in the clusters is linearized and blocked it is optionally denatured and sequencing probes hybridized to it. To prepare the primer mix, 895.5 μL of hybridization buffer and 4.5 μl of sequencing primer (100 μM) are mixed to a final volume of 900 μL. An exemplary sequence of a sequencing primer used can be:

5'ACACTCTTTCCCTACACGACGCTCTTCCGATC

To denature the nucleic acid within the clusters and to hybridize the sequencing primer, the computer component of the instrumentation flows the appropriate primer mix through the flow cell, e.g., as shown in the exemplary embodiments illustrated in Table 8.

TABLE 8

| Step | Solutions required | Temp (° C.) | Time (Sec) | Flow per channel (μL/min) | Pumped Vol |
|---|---|---|---|---|---|
| 1 | NaOH | 20 | 380 | 15 | 95 |
| 2 | TE | 20 | 380 | 15 | 95 |
| 3 | Primer mix | 60 | 380 | 15 | 95 |
| 4 | Hold at 60 C. | 60 | 900 | 0 | 0 |
| 5 | Wash buffer | 40 | 380 | 15 | 95 |
| 6 | Storage Buffer | 20 | 380 | 15 | 95 |

After denaturation and hybridization of the sequencing primer, the flow cell is ready for sequencing. Therefore, the flow cell is removed from the instrumentation of the current invention and moved to sequencing instrumentation as described in "Systems and Devices for Sequence by Synthesis Analysis," U.S. Ser. No. 60/788,248, filed Mar. 31, 2006 and International Application PCT/US2007/007991, filed Mar. 30, 2007.

DNA Sequencing Cycles

Sequencing of the clusters from the above illustrative protocol can be carried out using modified nucleotides prepared as described in International Patent application WO 2004/018493, and labeled with four different commercially available fluorophores (Molecular Probes Inc., Invitrogen, Carlsbad, Calif.).

A mutant 9° N polymerase enzyme (an exo-variant including the triple mutation L408Y/Y4O9A/P4IOV and C223S) is used for the nucleotide incorporation steps.

Incorporation mix, Incorporation buffer (50 mM Tris-HCl pH 8.0, 6 mM MgSO4, 1 mM EDTA, 0.05% (v/v) Tween-20, 50 mM NaCl) plus 110 nM YAV exo-C223S, and 1 μM each of the four labeled modified nucleotides, is applied to the clustered templates, and heated to 45° C.

Templates are maintained at 45° C. for 30 min, cooled to 20° C. and washed with Incorporation buffer, then with 5×SSC/0.05% Tween 20. Templates are then exposed to Imaging buffer (100 mM Tris pH7.0, 30 mM NaCl, 0.05% Tween 20, 50 mM sodium ascorbate, freshly dissolved). Templates are scanned in 4 colors at room temperature. Templates are then exposed to sequencing cycles of Cleavage and Incorporation as follows: Cleavage—Prime with Cleavage buffer (0.1M Tris pH 7.4, 0.1M NaCl and 0.05% Tween 20); Heat to 60° C.; Treat the clusters with Cleavage mix (100 mM TCEP in Cleavage buffer); Wait for a total of 15 min in addition to pumping fresh buffer every 4 min; Cool to 20° C.; Wash with Enzymology buffer; Wash with 5×SSC/0.05% Tween 20; Prime with Imaging buffer, and Scan in 4 colors at RT; Incorporation—Prime with Incorporation buffer Heat to 60° C.; Treat with Incorporation mix; wait for a total of 15 min in addition to pumping fresh Incorporation mix every 4 min; Cool to 20° C.; Wash with Incorporation buffer; Wash with 5×SSC/0.05% Tween 20; Prime with imaging buffer; and Scan in 4 colors at RT. The process of Incorporation and Cleavage is repeated for as many cycles as required.

Incorporated nucleotides are detected using a Total Internal Reflection based fluorescent CCD imaging apparatus described in "Systems and Devices for Sequence by Synthesis Analysis," U.S. Ser. No. 60/788,248, filed Mar. 31, 2006 and International Application PCT/US2007/007991, filed Mar. 30, 2007.

Figure 22:
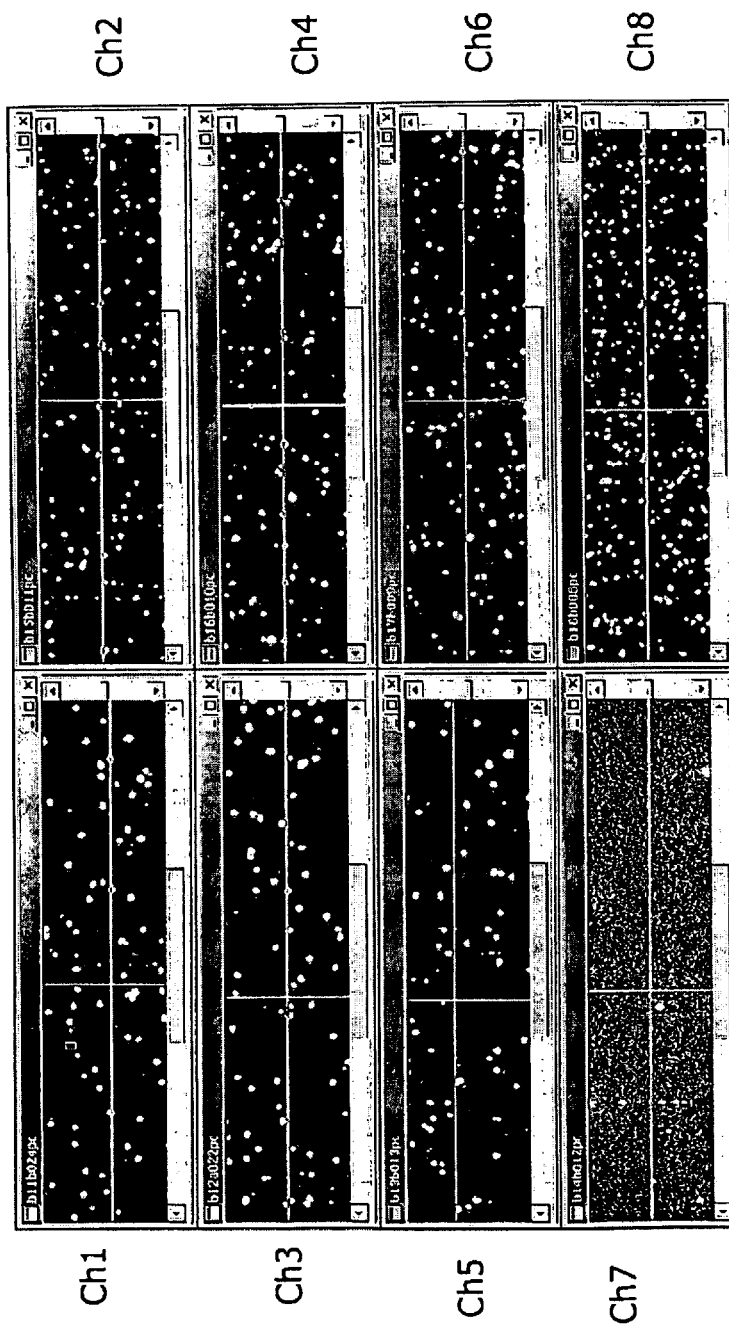
FIG. 22 displays exemplary nucleic acid cluster arrays isothermally created through use of the current invention.

A representative tile from a first cycle of nucleotide incorporation for each channel in a flow cell is shown in FIG. 22. This figure clearly shows the presence of clusters in each channel except channel 7, which had no template solution present in the hybridization mix. The clusters in FIG. 22 were grown through 35 cycles of isothermal amplification at 37 C and were taken through cycles of sequencing. The images from each cycle were analyzed to pick the brightest color for each cluster, and the image intensity analysis was used to call the base for each cluster at each cycle. Images from each cycle were co-localized to obtain the sequence corresponding to each cluster.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above may be used in various combinations. All publications, patents, patent applications, or other documents cited in this application are incorporated by reference in their entirety for all purposes to the same extent as if each individual publication, patent, patent application, or other document were individually indicated to be incorporated by reference for all purposes.

What is claimed is:

1. An assembly for creating nucleic acid cluster arrays, the assembly comprising:

a flow cell having a bottom side and a top side that face in opposite directions, the flow cell including an inlet hole and an outlet hole along the top side and a flow channel that fluidicly couples the inlet and outlet holes, the flow channel being defined by a surface that includes a plurality of oligonucleotides immobilized thereto for nucleic acid cluster generation; and a disposable manifold that is separable from the flow cell, the manifold including a main body configured to be mounted onto the flow cell, the main body comprising an outer side and an under side that face in opposite directions, the under side including an input port and an output port that align with the inlet hole and the outlet hole of the flow cell, respectively, when the under side is mounted onto the top side of the flow cell during the nucleic acid cluster generation, the manifold also including an input tube and an output tube that are coupled to the main body and in flow communication with the input and output ports, respectively, wherein fluid flows from the input tube, through the flow channel, and through the outlet tube during the nucleic acid cluster generation.

2. The assembly of claim 1, wherein the flow cell has a uniform thickness measured between the top side and the bottom side.

3. The assembly of claim 1, wherein the flow cell includes at least four of the flow channels, the flow channels having essentially equal lengths.

4. The assembly of claim 1, wherein the input tube and the output tube are coupled to the outer side of the main body, the input tube and the output tube being separated from each other along the outer side by a distance that is essentially equal to a length of the flow channel.

5. The assembly of claim 1, wherein the flow cell includes a plurality of the flow channels, wherein the number of input tubes and the number of output tubes is equal to the number of flow channels.

6. The assembly of claim 5, wherein each of the output tubes includes a tube end, the tube ends being coupled to a common manifold plug that is configured to removably couple to a system.

7. The assembly of claim 1, wherein the input tube and the output tube have respective tube ends that are configured to removably couple to respective ports of a system.

8. The assembly of claim 7, wherein at least one of the tube ends is coupled to a manifold plug that is configured to removably couple to the system.

9. The assembly of claim 1, wherein the main body includes first and second positioning holes that open to the under side and are configured to receive alignment posts of a system, the flow cell being located between the positioning holes when the main body is mounted onto the flow cell.

10. The assembly of claim 1, wherein the flow cell has an elongated structure such that a length of the flow cell is greater than a width of the flow cell.

11. The assembly of claim 1, wherein the plurality of oligonucleotides comprise primer oligonucleotides being located at an approximately uniform density over an area of the surface of the flow channel with one or more single stranded polynucleotide molecules being immobilized individually at intervals within the primer oligonucleotides.

12. A system for creating nucleic acid cluster arrays, the system comprising:

a system body having a placement area configured to receive a flow cell;

a temperature control device configured to regulate a temperature of the flow cell, the temperature control device including, or being in thermal communication with, the placement area;

a fluid flow system including at least one pump, the fluid flow system configured to direct fluid through the flow cell during nucleic acid cluster generation;

a computer control component functionally connected to the temperature control device and the fluid flow system, the computer control component configured to control the temperature control device and the fluid flow system to conduct the nucleic acid cluster generation; and a flow cell holder that is configured to move between open and closed positions, the flow cell holder permitting access to the placement area when in the open position for placing the flow cell on the placement area and placing a manifold onto the flow cell, the flow cell holder configured to press the manifold against the flow cell when in the closed position so that the manifold presses the flow cell toward the flow cell placement area.

13. The system of claim 12, wherein the flow cell holder includes a clamp that is coupled to the system body, the system further comprising a handle coupled to the system body, the clamp extending over the placement area when the flow cell holder is in the closed position, the handle coupling to the clamp to hold the clamp against the manifold.

14. The system of claim 12, wherein the system body includes a manifold attachment area include a plurality of ports, the ports being spaced apart from the placement area.

15. The system of claim 14, wherein the manifold attachment area is a first manifold attachment area, the system body including a second manifold attachment area having a plurality of ports that are spaced apart from the placement area and the first manifold attachment area.

16. The system of claim 12, wherein the flow cell holder includes a compression bar, the compression bar configured to exert a force toward the placement area when the flow cell holder is in the closed position.

17. The system of claim 12, wherein the temperature control device is a thermoelectric controller (TEC).

18. The system of claim 12, wherein the system body includes alignment posts that are positioned on opposite sides of the flow cell when the flow cell is positioned within the placement area.

19. The system of claim 12, wherein the placement area includes an edge that is sized and shaped to surround and hold the flow cell.

20. The system of claim 12, wherein the computer control component controls the temperature control device and the fluid flow system to generate the nucleic acid clusters through isothermal amplification.

21. The system of claim 12, further comprising the manifold and the flow cell.

* * * * *

SEQUENCE LISTING

```
<160> NUMBER OF SEQ ID NOS: 3

<210> SEQ ID NO 1
<211> LENGTH: 31
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: (11)..(11)
<223> OTHER INFORMATION: ARM 26 Diol 22A Linker

<400> SEQUENCE: 1
tttttttttt naatgatacg gcgaccaccg a                              31

<210> SEQ ID NO 2
<211> LENGTH: 31
<212> TYPE: DNA
<213> ORGANISM: Artificial Sequence
<220> FEATURE:
<223> OTHER INFORMATION: synthetic primer

<400> SEQUENCE: 2
tttttttttt caagcagaag acggcatacg a                              31

<210> SEQ ID NO 3
<211> LENGTH: 32
<212> TYPE: DNA
<213> ORGANISM: Artificial Sequence
<220> FEATURE:
<223> OTHER INFORMATION: Synthetic primer

<400> SEQUENCE: 3
acactctttc cctacacgac gctcttccga tc                             32
```